(12) United States Patent
Ito et al.

(10) Patent No.: US 7,683,225 B2
(45) Date of Patent: Mar. 23, 2010

(54) FLUORENE-BASED DERIVATIVE AND ORGANIC ELECTROLUMINESCENCE DEVICE EMPLOYING THE SAME

(75) Inventors: Mitsunori Ito, Chiba (JP); Hiroshi Yamamoto, Chiba (JP); Satoshi Hachiya, Chiba (JP); Hisayuki Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/282,640

(22) Filed: Nov. 21, 2005

(65) Prior Publication Data

US 2006/0159956 A1    Jul. 20, 2006

Related U.S. Application Data

(63) Continuation of application No. PCT/JP2005/009024, filed on May 18, 2005.

(30) Foreign Application Priority Data

Jun. 16, 2004    (JP) .............................. 2004-178679

(51) Int. Cl.
*C07C 13/62* (2006.01)
*H01L 51/54* (2006.01)

(52) U.S. Cl. .................... 585/22; 428/690; 428/917; 313/504; 313/506; 257/102; 257/103

(58) Field of Classification Search ................ 428/690, 428/917; 313/504, 506; 257/40
See application file for complete search history.

(56) References Cited

U.S. PATENT DOCUMENTS

| 3,008,897 | A | 11/1961 | Burk, Jr. et al. ......... 208/251 H |
| 6,203,933 | B1 | 3/2001 | Nakaya et al. .............. 428/690 |
| 6,281,627 | B1 | 8/2001 | Arai et al. ................... 313/506 |
| 6,514,633 | B1 | 2/2003 | Nii .............................. 428/690 |
| 2003/0087126 | A1 | 5/2003 | Ishida et al. ................ 428/690 |
| 2003/0091859 | A1 | 5/2003 | Cho et al. ................... 428/690 |
| 2004/0253389 | A1 | 12/2004 | Suzuki et al. ................ 428/1.1 |
| 2005/0233165 | A1 | 10/2005 | Ido et al. .................... 428/690 |
| 2006/0110623 | A1* | 5/2006 | Funahashi et al. ........... 428/690 |
| 2006/0134456 | A1 | 6/2006 | Ikeda et al. ................. 428/690 |

FOREIGN PATENT DOCUMENTS

| EP | 1 533 289 | 5/2005 |
| JP | 03-200889 | 9/1991 |
| JP | 07-138561 | 5/1995 |
| JP | 08-012600 | 1/1996 |
| JP | 08-239655 | 9/1996 |
| JP | 08-311442 | 11/1996 |
| JP | 2000-229893 | 8/2000 |
| JP | 2001-081451 | 3/2001 |
| JP | 2001-118682 | 4/2001 |
| JP | 2001-160489 | 6/2001 |
| JP | 2001-207167 | 7/2001 |
| JP | 2002-063988 | 2/2002 |
| JP | 2002-154993 | 5/2002 |
| JP | 2003-64003 | 3/2003 |
| JP | 2003-086357 | 3/2003 |
| JP | 2003-128651 | 5/2003 |
| JP | 2004-43349 | 2/2004 |
| JP | 2004-075567 | 3/2004 |
| JP | 2004-83481 | 3/2004 |
| WO | WO03/080559 | 10/2003 |
| WO | WO2004/013073 | 2/2004 |
| WO | WO2004/020373 | 3/2004 |
| WO | WO2004/020388 | 3/2004 |
| WO | WO2004/020548 | 3/2004 |

OTHER PUBLICATIONS

XP-002481014 Abstract of JP2004224766, Aug. 12, 2004.
Organic electroluminescent diodes, C.W. Tang and S.A. VanSlyke, Research Laboratories, Corporate Research Group, Eastman Kodak Company, Rochester, New York 14650, p. 913-915.
Highly efficient phosphorescent emission from organic electroluminescent devices, M.A. Baldo, D.F. O'Brien, Y. You, A. Shoustikov, S. Sibley, M.E. Thompson & S.R. Forrest, Letters to Nature, Nature, vol. 395, Sep. 10, 1998, p. 151-154.
Light-emitting diodes based on conjugated polymers, J.H. Burroughes, D.D.C. Bradley, A.R. Brown, R.N. Marks, K. Mackay, R.H. Friend, P.L. Burns & A.B. Holmes, Letters to Nature, Nature, vol. 347, Oct. 11, 1990, p. 539-541.

* cited by examiner

*Primary Examiner*—D. Lawrence Tarazano
*Assistant Examiner*—Camie S Thompson
(74) *Attorney, Agent, or Firm*—Oblon, Spivak, McClelland, Maier & Neustadt, L.L.P.

(57) ABSTRACT

A fluorene-based derivative having a specific structure and an organic electroluminescence device in which an organic thin film layer comprising a single layer or plural layers including at least a light emitting layer is sandwiched between a cathode and an anode, wherein at least one layer of the organic thin film layers described above comprises the above fluorene-based derivative having a specific structure in the form of a single component or a mixed component. The organic electroluminescence device has a high luminous efficiency, and the fluorene-based derivative materializes the same.

16 Claims, No Drawings

FLUORENE-BASED DERIVATIVE AND ORGANIC ELECTROLUMINESCENCE DEVICE EMPLOYING THE SAME

TECHNICAL FIELD

The present invention relates to an organic electroluminescence device and a fluorene-based derivative, more specifically to an organic electroluminescence device having a high luminous efficiency and a fluorene-based derivative which materializes the same.

BACKGROUND ART

An organic electroluminescence device (hereinafter "electroluminescence" shall be abbreviated as EL) is a spontaneous light emitting device making use of the principle that a fluorescent substance emits light by recombination energy of holes injected from an anode and electrons injected from a cathode by applying an electric field. Since a low voltage-driven organic EL device of a laminate type was reported by C. W. Tang of Eastman Kodak Company (C. W. Tang and S. A. Vanslyke, Applied Physics Letters, Vol. 51, p. 913, 1987), researches on organic EL devices comprising organic materials as structural materials have actively been carried out. Tang et al. use tris(8-hydroxyquinolinol)aluminum for the light emitting layer and a triphenyldiamine derivative for the hole transporting layer. The advantages of a laminate structure include that an efficiency of injecting holes into a light emitting layer can be elevated, that a forming efficiency of excitons formed by blocking electrons injected from a cathode to recombine them can be raised and that excitons formed in the light emitting layer can be shut up. As shown in the above example, a two layer type comprising a hole transporting (injecting) layer and an electron transporting and light emitting layer and a three layer type comprising a hole transporting (injecting) layer, a light emitting layer and an electron transporting (injecting) layer are well known as the device structures of the organic EL device. In such laminate type structural devices, device structures and forming methods are studied in order to enhance a recombination efficiency of holes and electrons injected.

Known as light emitting materials are chelate complexes such as a tris(8-quinolinolate)aluminum complex, coumarine derivatives, tetraphenylbutadiene derivatives, bisstyrylarylene derivatives and oxadiazole derivatives. It is reported that luminescence of a blue color to a red color in a visible region is obtained from them, and it is expected that a color display device is materialized (for example, patent documents 1 to 3).

In recent years, it is investigated in many cases to use energy of a triplet state for EL luminescence by using a phosphorescent compound as a light emitting material. It is reported by the group of Princeton University that an organic luminescence device using an iridium complex as a light emitting material shows a high luminous efficiency (non-patent document 1). Further, an organic luminescence device using a conjugated polymer in addition to the organic luminescence device using the low molecular material described above is reported by the group of Princeton University (non-patent document 2). In this report, luminescence is confirmed in a single layer by making a film from polyphenylenevinylene in a coating system.

As described above, organic EL devices are notably progressing in recent years, and since characteristics thereof are a high luminance at a low applied voltage, a diversification in a luminous wavelength, a high speed response and possibility of preparing a thin and light-weight luminescence device, it is indicated that they can be applied to broad uses.

As organic EL devices are notably progressing, performances required to the light emitting materials are growing high, and fluorene compounds having specific structures are disclosed as a material providing luminescence of a high luminance at low voltage and having an excellent durability in a patent document 4 (Canon Inc.) and a patent document 5 (Mitsui Chemicals Inc.).

However, the light output of a higher luminance and the higher conversion efficiency are required in order to enhance the practical performances. Also, a lot of problems are still involved in terms of durability against a change with the passage of time caused by use over a long period of time and deterioration caused by ambient gas including oxygen and humidity. Further, considering application thereof to full color displays, luminance of blue, green and red colors each having a good color purity are required, but these problems are not still sufficiently solved.

Patent document 1: Japanese Patent Application Laid-Open No. Hei 8-239655
Patent document 2: Japanese Patent Application Laid-Open No. Hei 7-138561
Patent document 3: Japanese Patent Application Laid-Open No. Hei 3-200889.
Patent document 4: Japanese Patent Application Laid-Open No. 83481/2004
Patent document 5: Japanese Patent Application Laid-Open No. 43349/2004
Non-patent document 1: Nature, 395, 151 (1998)
Non-patent document 2: Nature, 347, 539 (1990)

DISCLOSURE OF THE INVENTION

The present invention has been made in order to overcome the problems described above, and an object thereof is to provide an organic EL device having a high luminous efficiency and a fluorene-based derivative which materializes the same.

Intensive researches repeated by the present inventors in order to achieve the object described above have resulted in finding that the object described above can be achieved by using a fluorene-based derivative represented by the following Formula (1) as a light emitting material for an organic EL device, and thus they have come to complete the present invention.

That is, the present invention provides a fluorene-based derivative expressed by the following Formula (1):

  (1)

wherein k and n each are an integer of 0 to 10 and satisfy k+n>1;

m is an integer of 1 to 10;

X and Y each independently represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms; and X and Y may be the same with or different from each other;

A and C each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group or alkylene group having 1 to 50 carbon atoms or a substituted or unsubstituted alkenyl group or alkenylene group having 1 to 50 carbon atoms; A and C may be the same with or different from each other; however, when X or Y is a single bond, A or C represents a substituted or unsubstituted condensed polycyclic aromatic group having two rings or a substituted or unsubstituted condensed polycyclic heterocyclic group having two rings;

B is a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms;

FL is a fluorene-based derivative group represented by any of the following Formulas (2) to (5) and (11) to (12) or a group comprising the combination of these fluorene-based derivative groups, and when m is 2 or more, a plurality of (FL—B) may be the same with or different from each other;

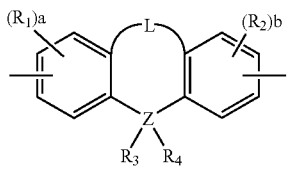
(2)

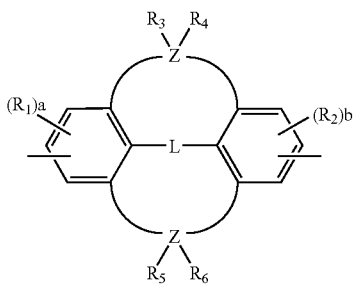
(3)

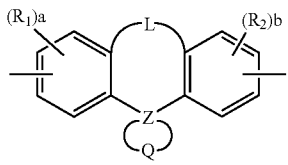
(4)

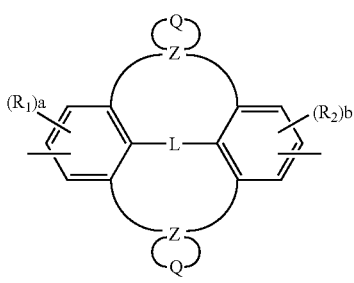
(5)

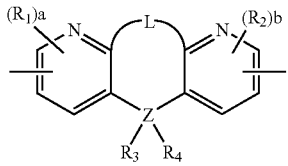
(11)

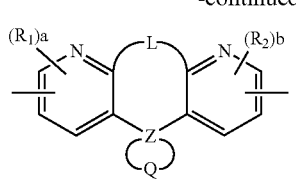
(12)

In Formulas (2) to (5) and (11) to (12), L represents a single bond, $-(CR'R'')_c-$, $-(SiR'R'')_c-$, $-O-$, $-CO-$ or $-NR'-$ (R' and R'' each independently represents a hydrogen atom, a substituted or unsubstituted aromatic group having 6 to 50 nuclear carbon atoms, a substituted or unsubstituted aromatic heterocyclic group having 5 to 50 nuclear atoms or a substituted or unsubstituted alkyl group having 1 to 50 carbon atoms; e is an integer of 1 to 10; and R' and R'' may be the same with or different from each other);

Z is a carbon atom, a silicon atom or a germanium atom;

Q is a cyclic structure-forming group, and a cyclic structure formed by Z—Q may further be condensed with a substituted or unsubstituted cycloalkyl group having 1 to 50 carbon atoms, a substituted or unsubstituted aromatic group having 6 to 50 nuclear carbon atoms or a substituted or unsubstituted aromatic heterocyclic group having 5 to 50 nuclear atoms;

$R_1$ to $R_6$ each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 2 to 50 carbon atoms, a carboxyl group, a halogen atom, a cyano group, a nitro group or a hydroxyl group; when plural $R_1$ to $R_6$ are present, they may be the same with or different from each other, and adjacent groups out of $R_1$ to $R_6$ may bond each other to form a ring structure;

a and b each are an integer of 0 to 4.

Further, the present invention provides an organic EL device in which an organic thin film layer comprising a single layer or plural layers including at least a light emitting layer is sandwiched between a cathode and an anode, wherein at least one layer of the organic thin film layers described above comprises the fluorene-based derivative represented by Formula (1) described above in the form of a single component or a mixed component.

The organic EL device of the present invention and the organic EL device prepared by using the fluorene-based derivative of the present invention have a high luminous efficiency.

BEST MODE FOR CARRYING OUT THE INVENTION

The fluorene-based derivative of the present invention is represented by the following Formula (1):

$$(A-X)_k-(FL-B)_m-(Y-C)_n \quad (1)$$

In Formula (1), k and n each are an integer of 0 to 10 (preferably 0 to 5) and satisfy k+n≧1, and m is an integer of 1 to 10 (preferably 1 to 5).

In Formula (1), X and Y each independently represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms, and X and Y may be the same with or different from each other.

The examples of the aromatic group represented by X and Y described above include phenylene, 1-naphthylene, 2-naphthylene, 1-anthrylene, 2-anthrylene, 9-anthrylene, 1-phenanthrylene, 2-phenanthrylene, 3-phenanthrylene, 4-phenanthrylene, 9-phenanthrylene, 1-naphthacenylene, 2-naphthacenylene, 9-naphthacenylene, 1-pyrenylene, 2-pyrenylene, 4-pyrenylene, 2-biphenyldiyl, 3-biphenyldiyl, 4-biphenyldiyl, p-terphenyl-4-diyl, p-terphenyl-3-diyl, p-terphenyl-2-diyl, m-terphenyl-4-diyl, m-terphenyl-3-diyl, m-terphenyl-2-diyl, o-tolylene, m-tolylene, p-tolylene, p-t-butylphenylene, p-(2-phenylpropyl)phenylene, 3-methyl-2-naphthylene, 4-methyl-1-naphthylene, 4-methyl-1-anthrylene, 4'-methylbiphenyldiylene and 4"-t-butyl-p-terphenyl-4-diylene.

The examples of the alkylene group represented by X and Y described above include methylene, ethylene, propylene, isopropylene, n-butylene, s-butylene, isobutylene, dimethylmethylene, n-pentylene, n-hexylene, n-heptylene, n-octylene, chloromethylene, 1-chloroethylene, 2-chloroethylene, 2-chloroisobutylene, 1,2-dichloroethylene, 1,3-dichloroisopropylene, 1,2,3-trichloropropylene, bromomethylene, 1-bromoethylene, 2-bromoethylene, 2-bromoisobutylene, 1,2-dibromoethylene, 1,3-dibromoisopropylene, 1,2,3-tribromopropylene, iodomethylene, 1-iodoethylene, 2-iodoethylene, 2-iodoisobutylene, 1,2-diiodoethylene, 1,3-diiodoisopropylene, 1,2,3-triiodopropylene, cyclopropylene, cyclobutylene, cyclopentylene, cyclohexylene, 4-methylcyclohexylene, adamantane-1,1-diyl and adamantane-1,3-diyl.

The alkenylene group represented by X and Y described above includes, for example, vinylene, allylene, 1-butenylene, 2-butenylene, 3-butenylene, 1,3-butanedienylene, 1-methylvinylene, styrylene, 2,2-diphenylvinylene, 1,2-diphenylvinylene, 1-methylallylene, 1,1-dimethylallylene, 2-methylallylene, 1-phenylallylene, 2-phenylallylene, 3-phenylallylene, 3,3-diphenylallylene, 1,2-dimethylallylene, 1-phenyl-1-butenylene and 3-phenyl-1-butenylene.

In Formula (1), A and C each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group or alkylene group having 1 to 50 carbon atoms or a substituted or unsubstituted alkenyl group or alkenylene group having 1 to 50 carbon atoms; A and C may be the same with or different from each other; however, when X or Y is a single bond, A or C represents a substituted or unsubstituted condensed polycyclic aromatic group having two rings or a substituted or unsubstituted condensed polycyclic heterocyclic group having two rings.

The examples of the aromatic group represented by A and C described above include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl.

The examples of the aromatic heterocyclic group represented by A and C described above include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and divalent groups thereof.

The examples of the alkyl group represented by A and C described above include methyl, ethyl, propyl, isopropyl, n-butyl, s-butyl, isobutyl, dimethylmethyl, n-pentyl, n-hexyl, n-heptyl, n-octyl, chloromethyl, 1-chloroethyl, 2-chloroethyl, 2-chloroisobutyl, 1,2-dichloroethyl, 1,3-dichloroisopropyl, 1,2,3-trichloropropyl, bromomethyl, 1-bromoethyl, 2-bromoethyl, 2-bromoisobutyl, 1,2-dibromoethyl, 1,3-dibromoisopropyl, 1,2,3-tribromopropyl, iodomethyl, 1-iodoethyle, 2-iodoethyl, 2-iodoisobutyl, 1,2-diiodoethyl, 1,3-diiodoisopropyl, 1,2,3-triiodopropyl, cyclopropyl, cyclobutyl, cyclopentyl, cyclohexyl, 4-methylcyclohexyl, adamantane-1,1-diyl and adamantane-1,3-diyl. Also, the alkylene group includes divalent groups thereof.

The alkenyl group represented by A and C described above includes, for example, vinyl, allyl, 1-butenyl, 2-butenyl, 3-butenyl, 1,3-butanedienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl and 3-phenyl-1-butenyl. Also, the alkenylene group includes divalent groups thereof.

The condensed polycyclic aromatic group represented by A and C described above includes those having a condensed ring structure out of the aromatic groups described above.

The condensed polycyclic heterocyclic group represented by A and C described above includes those having a condensed ring structure out of the aromatic heterocyclic groups described above.

In Formula (1), (A—X) and/or (Y—C) preferably is a structure represented by any of the following Formulas (6) to (10):

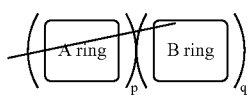 (6)

Formula (6) illustrates a condensed ring group consisting of an A ring and a B ring; the A ring is a substituted or unsubstituted aromatic group having 6 to 50 nuclear carbon atoms or a substituted or unsubstituted aromatic heterocyclic group having 5 to 50 nuclear atoms; the B ring is a substituted or unsubstituted cycloalkyl group having 1 to 50 carbon atoms, a substituted or unsubstituted aromatic group having 6 to 50 nuclear carbon atoms or a substituted or unsubstituted aromatic heterocyclic group having 5 to 50 nuclear atoms; and p and q each are an integer of 0 to 10 and satisfy p+q≧2.

The examples of the aromatic group in the A ring described above include the same examples as given in A and C described above.

The examples of the aromatic heterocyclic group in the A ring described above include the same examples as given in A and C described above.

The examples of the cycloalkyl group in the B ring described above include cyclopropyl, cyclobutyl, cyclopentyl, cyclohexyl and 4-methylcyclohexyl.

The examples of the aromatic group in the B ring described above include the same examples as given in A and C described above.

The examples of the heterocyclic group in the B ring described above include residues of ethylene oxide, ethylene sulfide, trimethylene oxide, trimethylene sulfide, tetrahydrofuran, tetrahydropyrane, tetrahydrothiophene, pyrrolidine, pyrazolidine, imidazolidine, isoxazolidine, isothiazolidine, piperidine, piperazine, morpholine, thiomorpholine, quinuclidine, etc., those being as saturated heterocyclic groups in addition to the same examples as the aromatic heterocyclic groups given in A and C described above.

—Ar$_1$—CH=CH—Ar$_2$ (7)

In Formula (7), Ar$_1$ is a substituted or unsubstituted alkylene group having 1 to 50 carbon atoms, a substituted or unsubstituted aromatic group having 6 to 50 nuclear carbon atoms or a substituted or unsubstituted aromatic heterocyclic group having 5 to 50 nuclear atoms; Ar$_2$ is a substituted or unsubstituted aromatic group having 6 to 50 nuclear carbon atoms or a substituted or unsubstituted aromatic heterocyclic group having 5 to 50 nuclear atoms.

The specific examples of the above respective groups include the same examples as given in A and C described above and given in X and Y described above.

—R$_3$—Ar$_3$ (8)

In Formula (8), R$_3$ is a substituted or unsubstituted alkylene group having 1 to 50 carbon atoms, and Ar$_3$ is a substituted or unsubstituted aromatic group having 6 to 50 nuclear carbon atoms or a substituted or unsubstituted aromatic heterocyclic group having 5 to 50 nuclear atoms.

The specific examples of the above respective groups include the same examples as given in A and C described above and given in X and Y described above.

—Ar$_4$—FA$_1$ (9)

In Formula (9), Ar$_4$ is a substituted or unsubstituted aromatic group having 6 to 50 nuclear carbon atoms or a substituted or unsubstituted aromatic heterocyclic group having 5 to 50 nuclear atoms, and FA$_1$ is a substituted or unsubstituted condensed aromatic group having 8 to 50 nuclear carbon atoms or a substituted or unsubstituted condensed aromatic heterocyclic group having 8 to 50 nuclear atoms.

The aromatic groups and the aromatic heterocyclic group represented by Ar$_4$ described above include the same examples as given in X and Y described above.

The condensed aromatic groups and the condensed aromatic heterocyclic group represented by FA$_1$ described above include those having a condensed ring structure out of the aromatic groups and the aromatic heterocyclic groups each represented by A and C described above.

—FA$_2$—FA$_3$ (10)

In Formula (10), FA$_2$ is a substituted condensed aromatic group having 8 to 50 nuclear carbon atoms or a substituted condensed aromatic heterocyclic group having 8 to 50 nuclear atoms, and FA$_3$ is a substituted or unsubstituted condensed aromatic group having 8 to 50 nuclear carbon atoms or a substituted or unsubstituted condensed aromatic heterocyclic group having 8 to 50 nuclear atoms.

The condensed aromatic groups and the condensed aromatic heterocyclic group each represented by FA$_2$ described above include those having a condensed ring structure out of the aromatic groups and the aromatic heterocyclic groups each represented by A and C described above.

The condensed aromatic groups and the condensed aromatic heterocyclic group each represented by FA$_3$ described above include those having a condensed ring structure out of the aromatic groups and the aromatic heterocyclic groups each represented by A and C described above.

The structures represented by Formulas (6) to (10) are preferably the following specific examples or residues thereof:

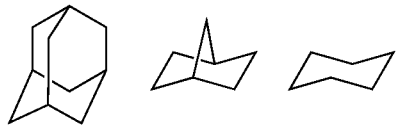

-continued
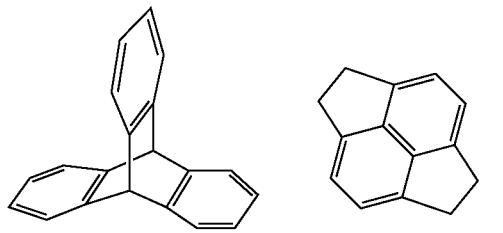
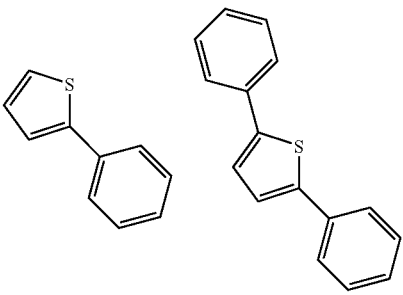
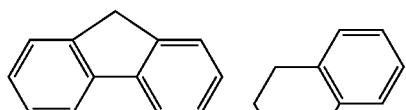
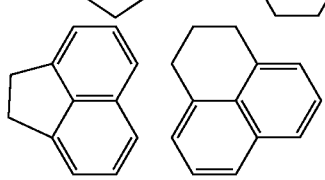
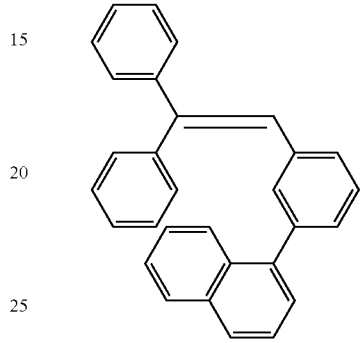
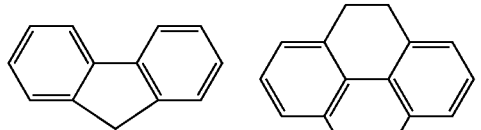
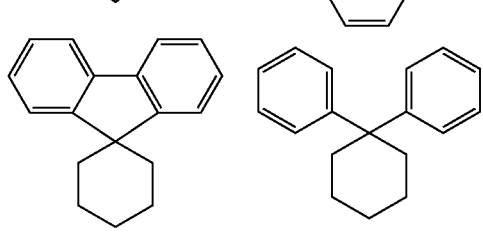
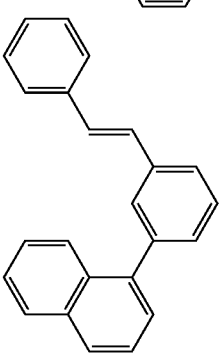
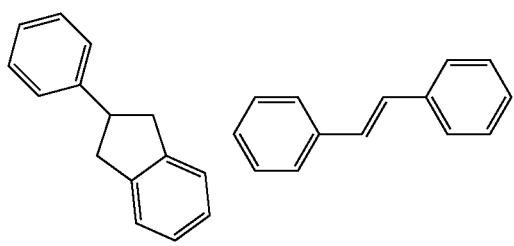
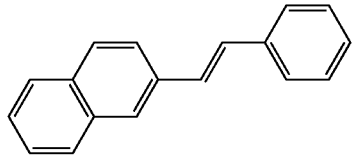
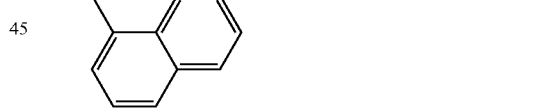
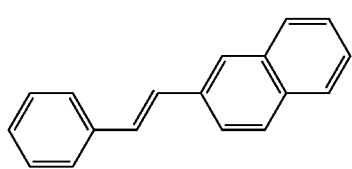
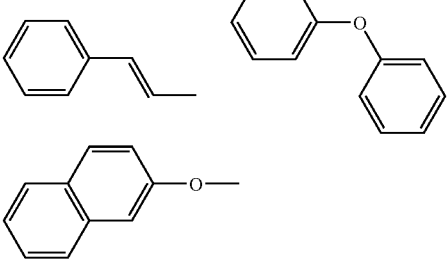

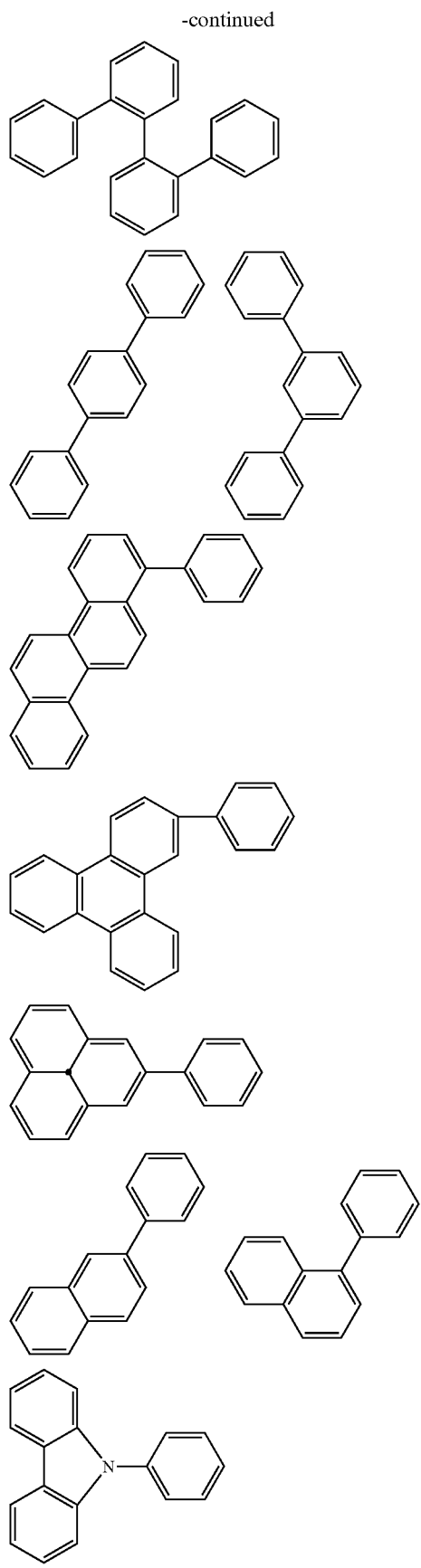
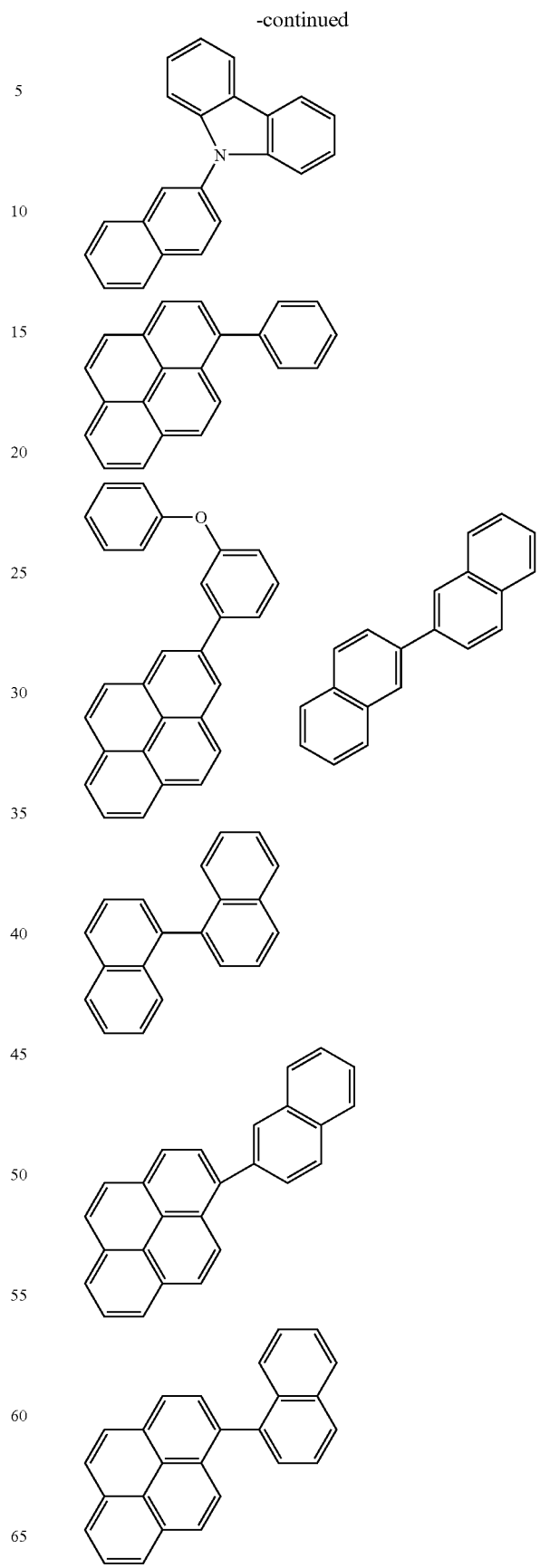

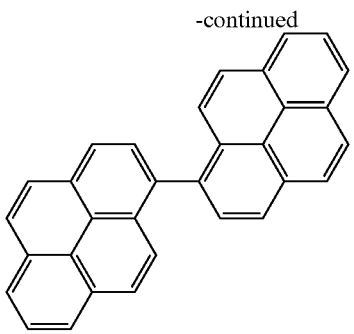

In Formula (1), FL is a fluorene-based derivative group represented by any of the following Formulas (2) to (5) and (11) to (12) or a group comprising the combination of these fluorene-based derivative groups, and when m is 2 or more, a plurality of (FL—B) may be the same with or different from each other;

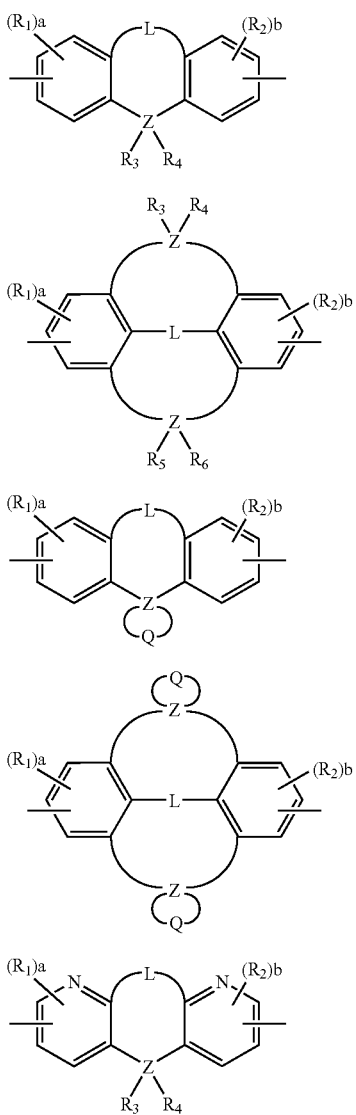

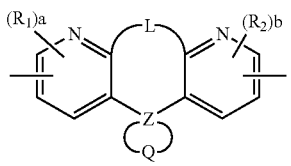

In Formulas (2) to (5) and (11) to (12), L represents a single bond, —(CR'R")$_c$—, —(SiR'R")$_c$—, —O—, —CO— or —NR'— (R' and R" each independently represents a hydrogen atom, a substituted or unsubstituted aromatic group having 6 to 50 nuclear carbon atoms, a substituted or unsubstituted aromatic heterocyclic group having 5 to 50 nuclear atoms or a substituted or unsubstituted alkyl group having 1 to 50 carbon atoms; c is an integer of 1 to 10; and R' and R" may be the same with or different from each other).

The specific examples of R' and R" include the same examples give in A and C described above.

In Formulas (2) to (5) and (11) to (12), Z represents a carbon atom, a silicon atom or a germanium atom.

In Formulas (2) to (5) and (11) to (12), Q represents a cyclic structure-forming group, and a cyclic structure formed by Z—Q may further be condensed with a substituted or unsubstituted cycloalkyl group having 1 to 50 carbon atoms, a substituted or unsubstituted aromatic group having 6 to 50 nuclear carbon atoms or a substituted or unsubstituted aromatic heterocyclic group having 5 to 50 nuclear atoms. The specific examples of the above respective groups include the same examples as described above.

In Formulas (2) to (5) and (11) to (12), a and b each are an integer of 0 to 4, preferably 0 to 2.

In Formulas (2) to (5) and (11) to (12), $R_1$ to $R_6$ each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 2 to 50 carbon atoms, a carboxyl group, a halogen atom, a cyano group, a nitro group or a hydroxyl group. When plural $R_1$ to $R_6$ are present, they may be the same with or different from each other, and the adjacent groups out of $R_1$ to $R_6$ may bond each other to form a ring structure.

The examples of the substituted or unsubstituted aromatic group having 6 to 50 nuclear carbon atoms represented by $R_1$ to $R_6$ include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl.

The examples of the substituted or unsubstituted aromatic heterocyclic group having 5 to 50 nuclear atoms represented by $R_1$ to $R_6$ include 1-pyrrolyl, 2-pyrrolyl, 3-pyrrolyl, pyrazinyl, pyrimidyl, pyridazyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

The examples of the substituted or unsubstituted alkyl group having 1 to 50 carbon atoms represented by $R_1$ to $R_6$ include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcyclohexyl, 1-adamantyl, 2-adamantyl, 1-norbornyl and 2-norbornyl.

The substituted or unsubstituted alkoxy group having 1 to 50 carbon atoms represented by $R_1$ to $R_6$ is a group represented by —$OY_1$, and the examples of $Y_1$ include the same examples as the alkyl groups described above.

The examples of the substituted or unsubstituted aralkyl group having 1 to 50 carbon atoms represented by $R_1$ to $R_6$ include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

The substituted or unsubstituted aryloxy group having 5 to 50 nuclear carbon atoms represented by $R_1$ to $R_6$ is represented by —$OY_2$, and the examples of $Y_2$ include the same examples as the aryl groups described above.

The substituted or unsubstituted arylthio group having 5 to 50 carbon atoms represented by $R_1$ to $R_6$ is a group represented by —$SY_3$, and the examples of $Y_3$ include the same examples as the aryl groups described above.

The substituted or unsubstituted alkoxycarbonyl group represented by $R_1$ to $R_6$ is a group represented by —$COOZ_1$, and the examples of $Z_1$ include the same examples as the alkyl groups described above.

The groups represented by Formulas (2) to (5) are preferably the specific examples having the following structures.

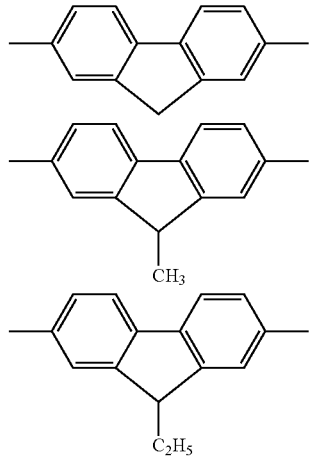

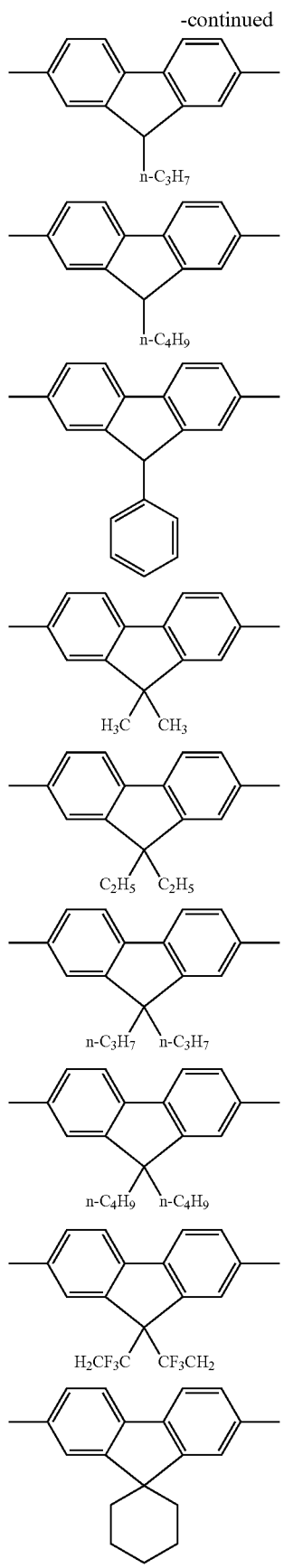
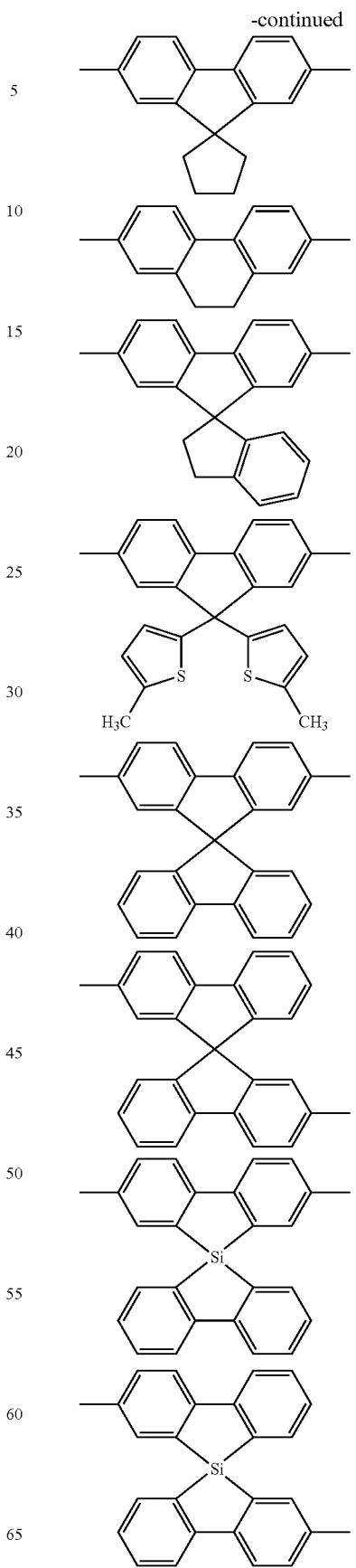

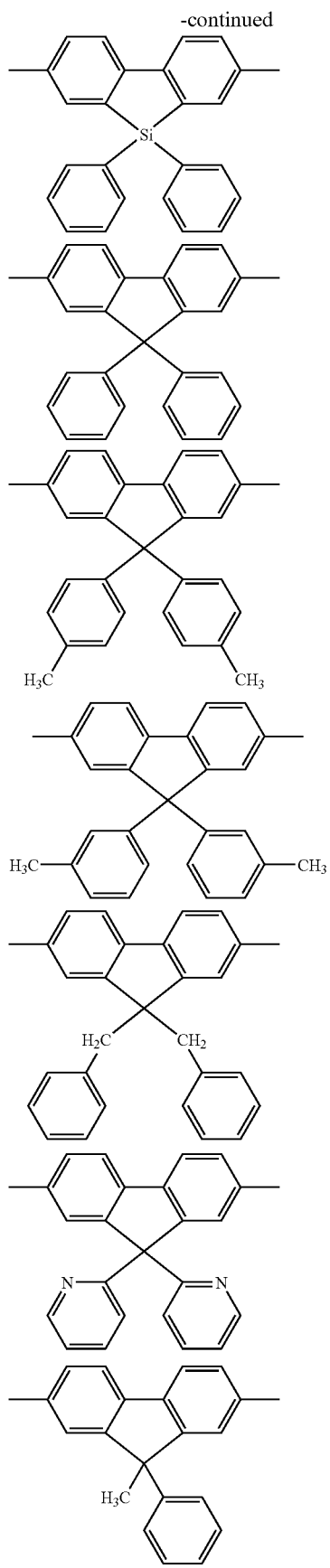
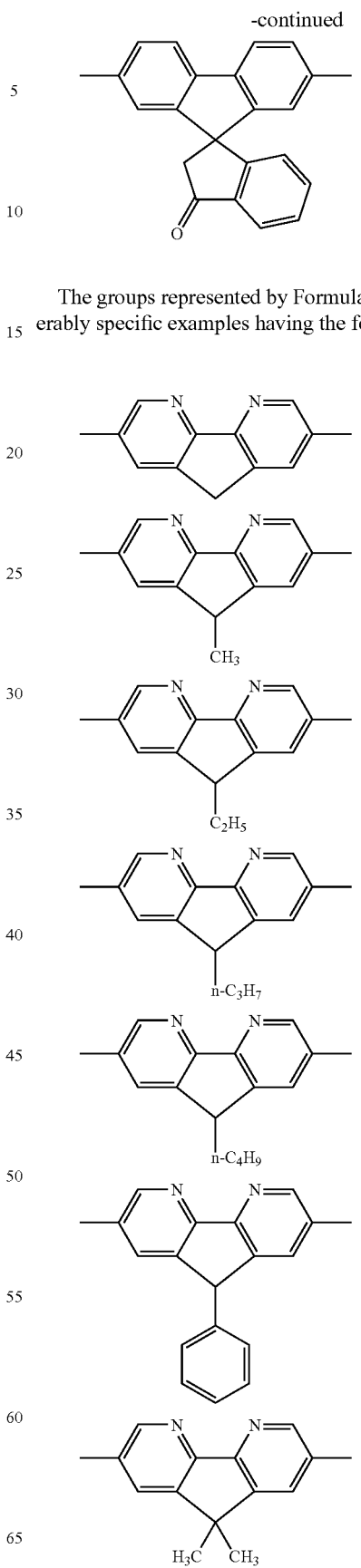
The groups represented by Formulas (11) to (12) are preferably specific examples having the following structures.

-continued
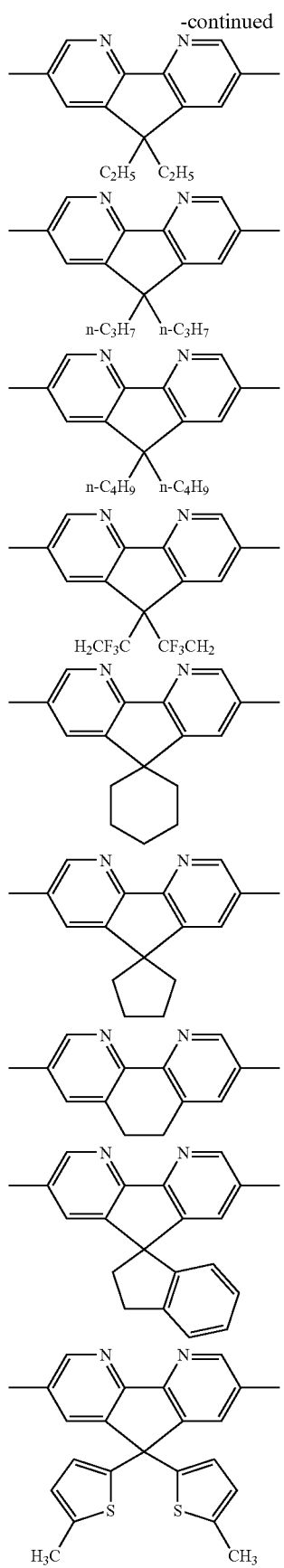
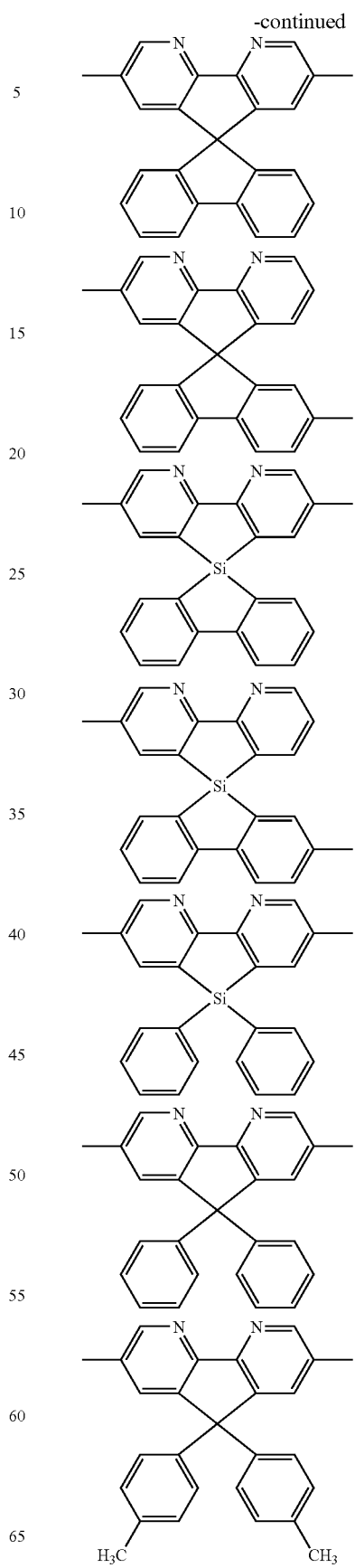

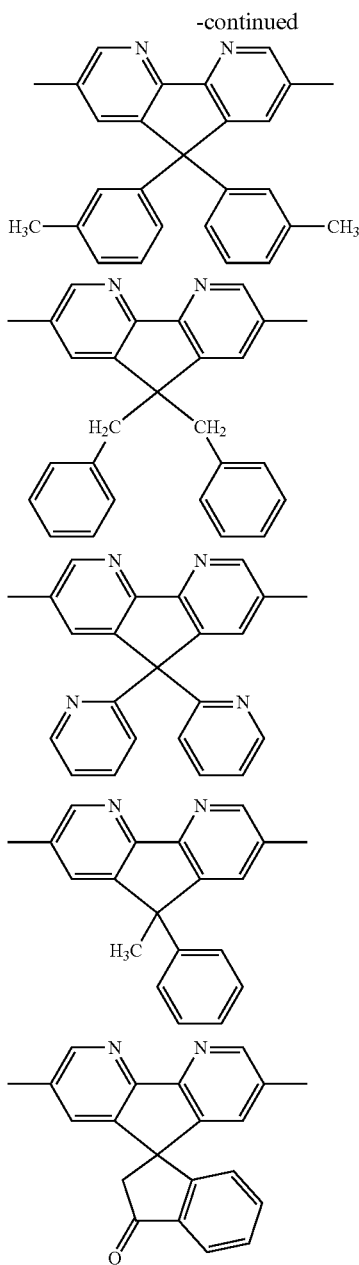

Substituents for the respective groups in the fluorene-based derivative represented by Formula (1) include the same group and specific examples as in $R_1$ to $R_6$ described above.

The fluorene-based derivative represented by Formula (1) is preferably those represented by the following formulas:

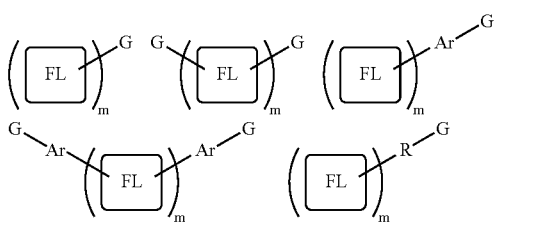

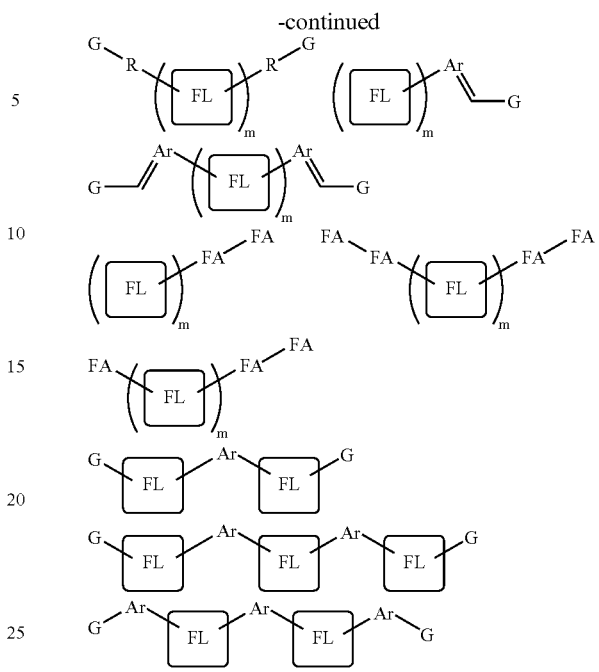

In the respective formulas described above, FL is the same as described above; G is a structure represented by any of Formulas (6) to (11); Ar represents a substituted or unsubstituted aromatic group having 6 to 50 nuclear carbon atoms or a substituted or unsubstituted aromatic heterocyclic group having 5 to 50 nuclear atoms; R represents a substituted or unsubstituted alkylene group having 1 to 50 carbon atoms or a substituted or unsubstituted alkenylene group having 1 to 50 carbon atoms; FA represents a substituted or unsubstituted condensed aromatic group having 8 to 50 nuclear carbon atoms or a substituted or unsubstituted condensed aromatic heterocyclic group having 8 to 50 nuclear atoms, and it is preferably the residues of condensed rings having the following structures:

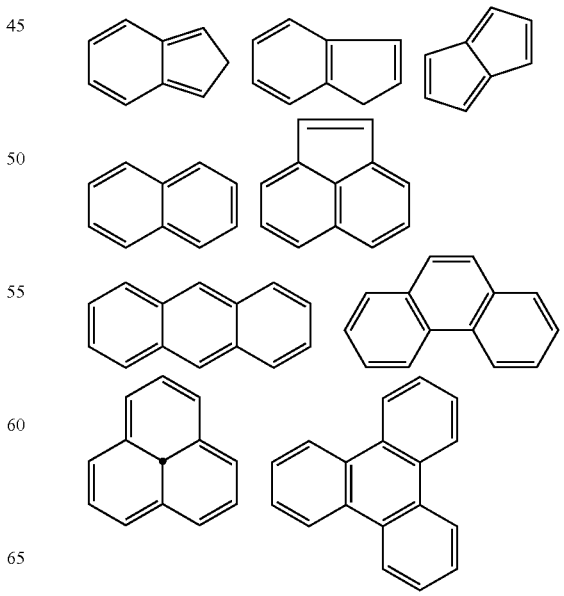

-continued
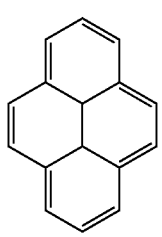 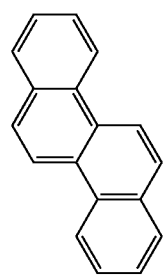
The specific examples of the above respective groups and the substituents thereof include the same ones as explained in Formula (1) described above.
The specific examples of the fluorene-based derivative of the present invention represented by Formula (1) shall be shown below, but they shall not be restricted to the compounds of these examples:
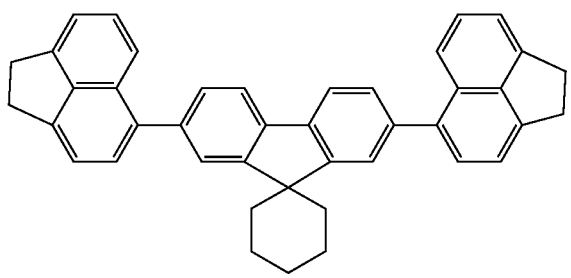
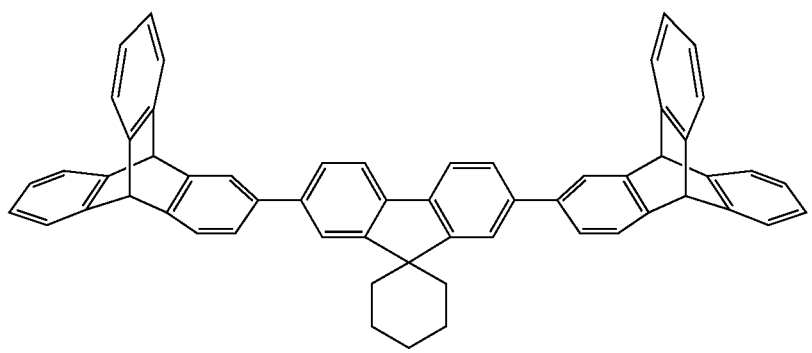
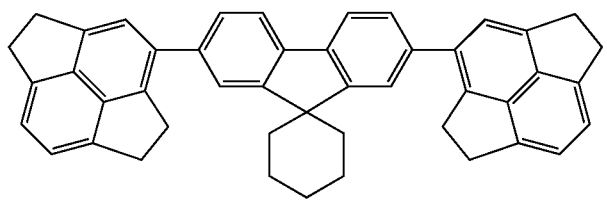
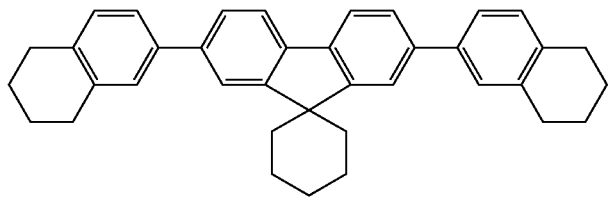
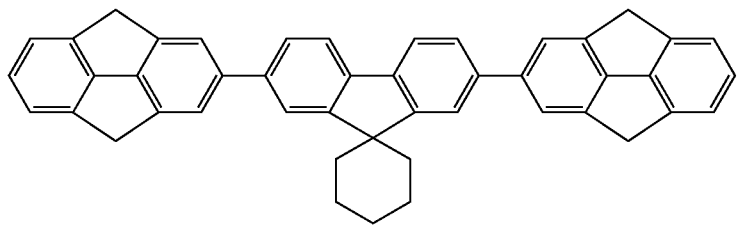

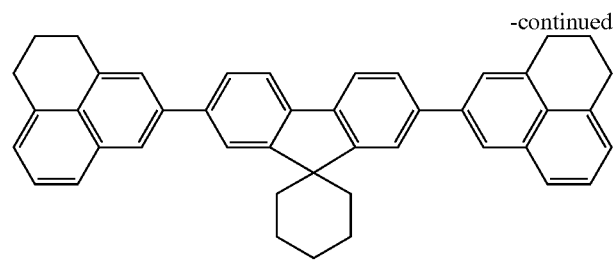
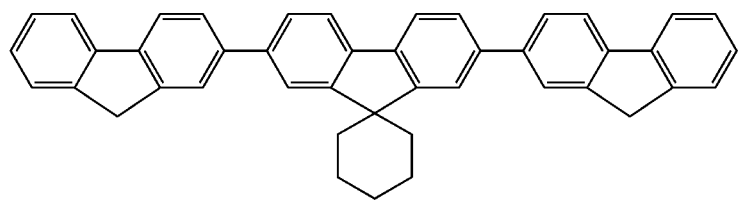
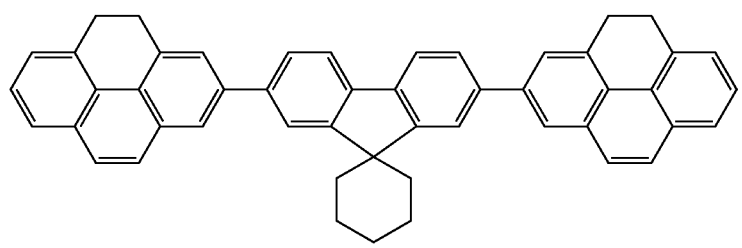
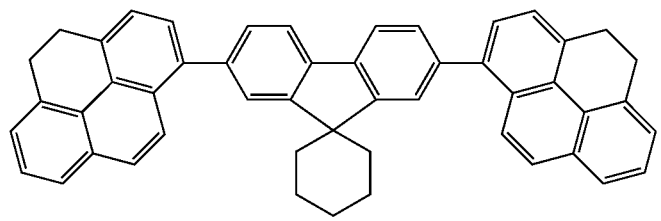
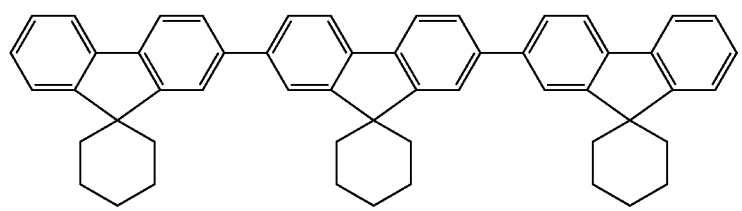
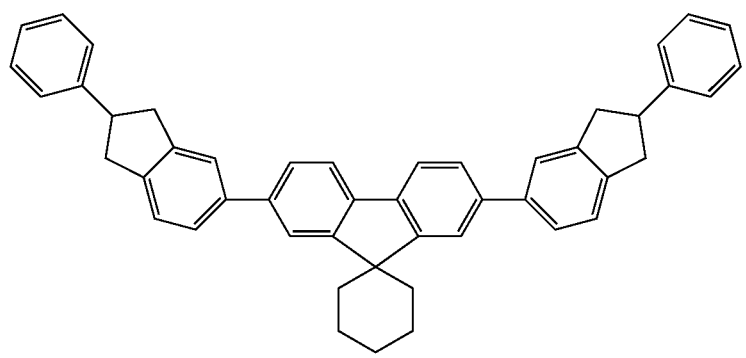

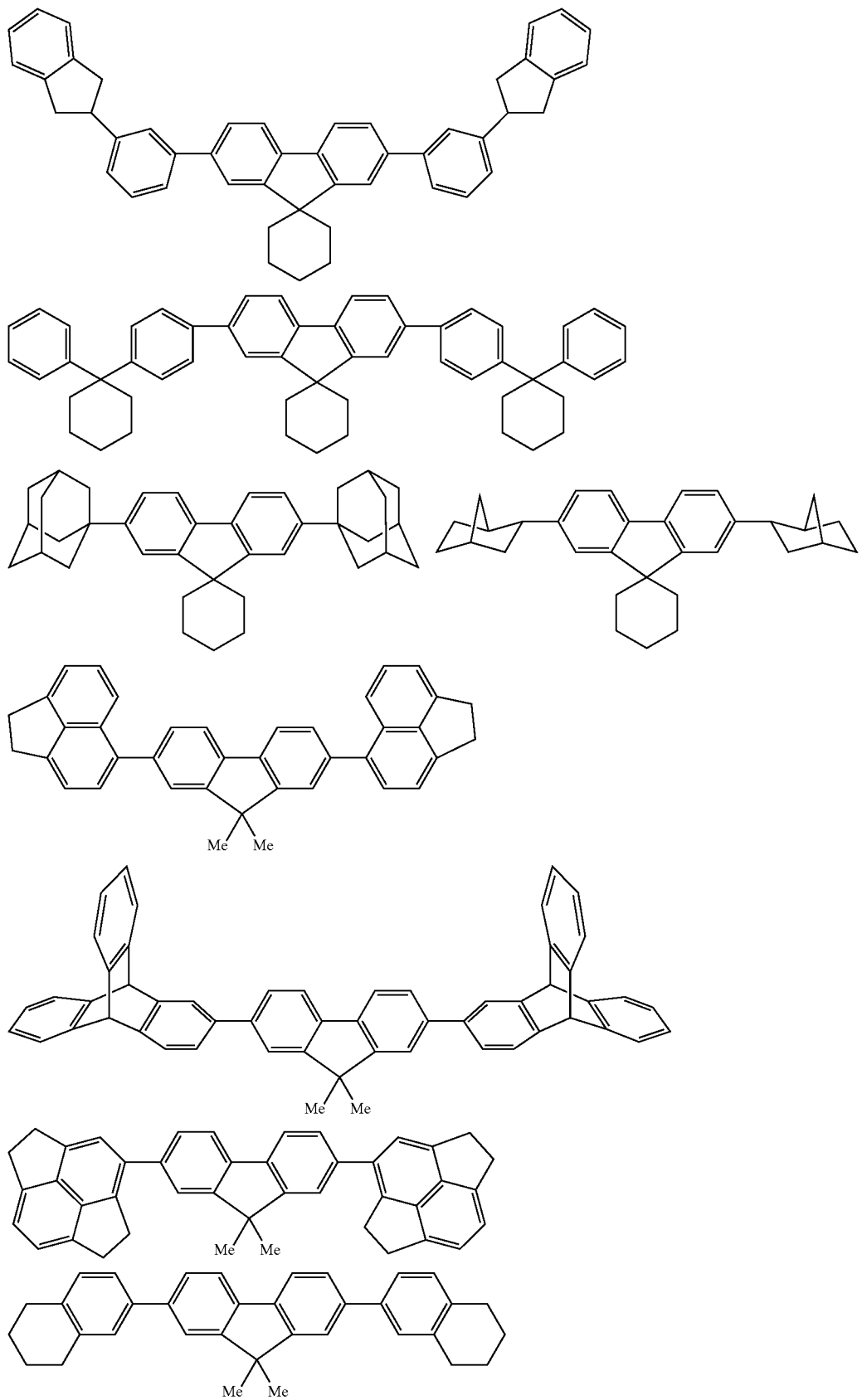

-continued
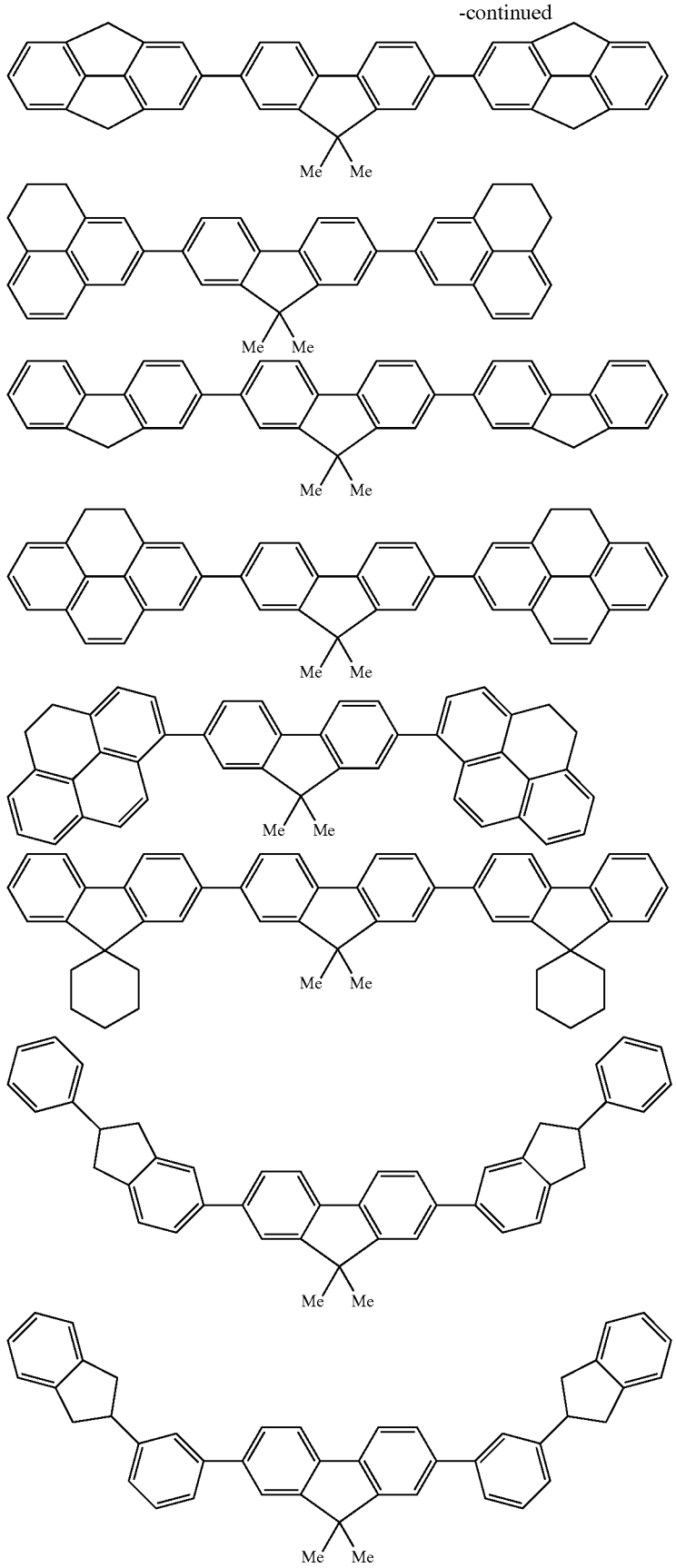

-continued
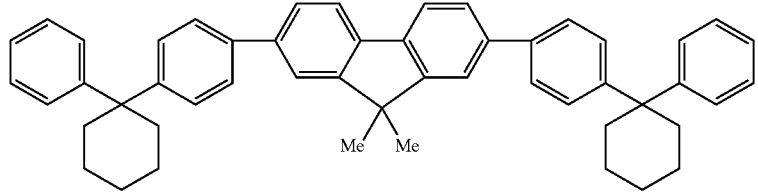
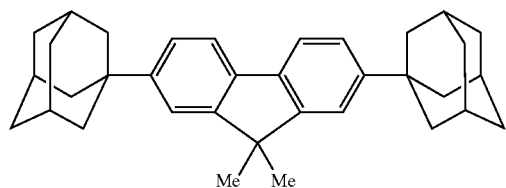
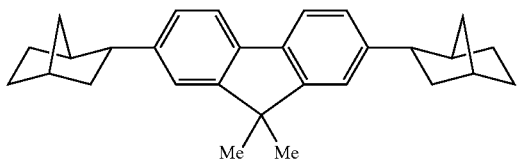
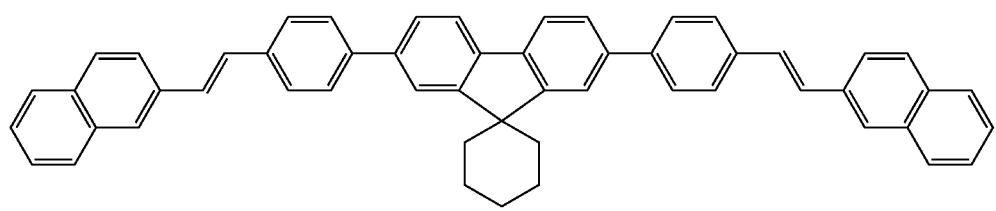
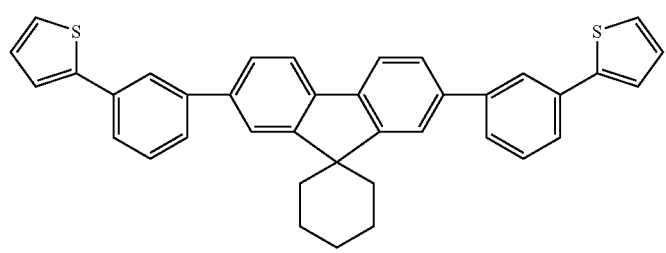
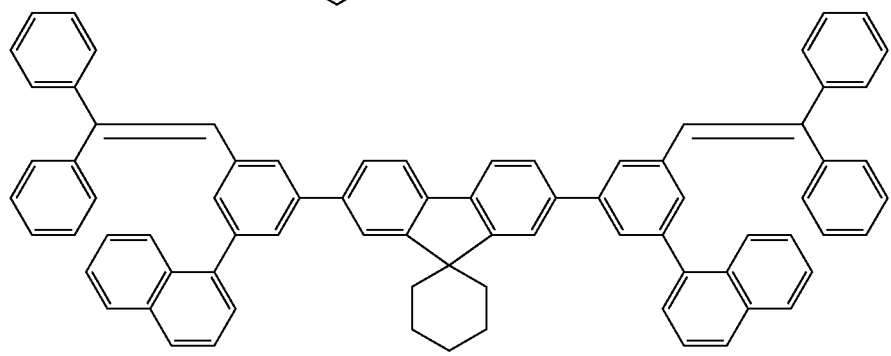
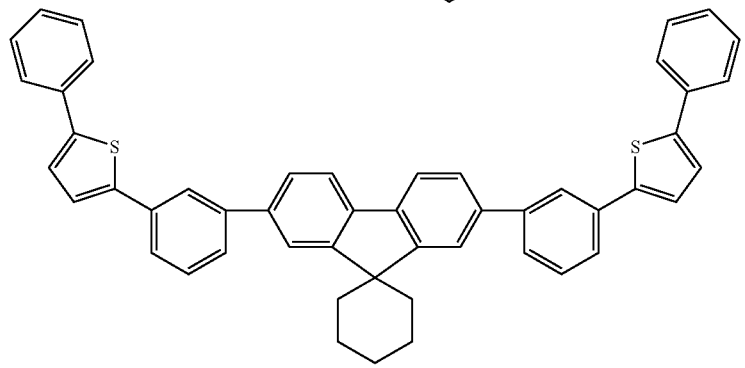

-continued
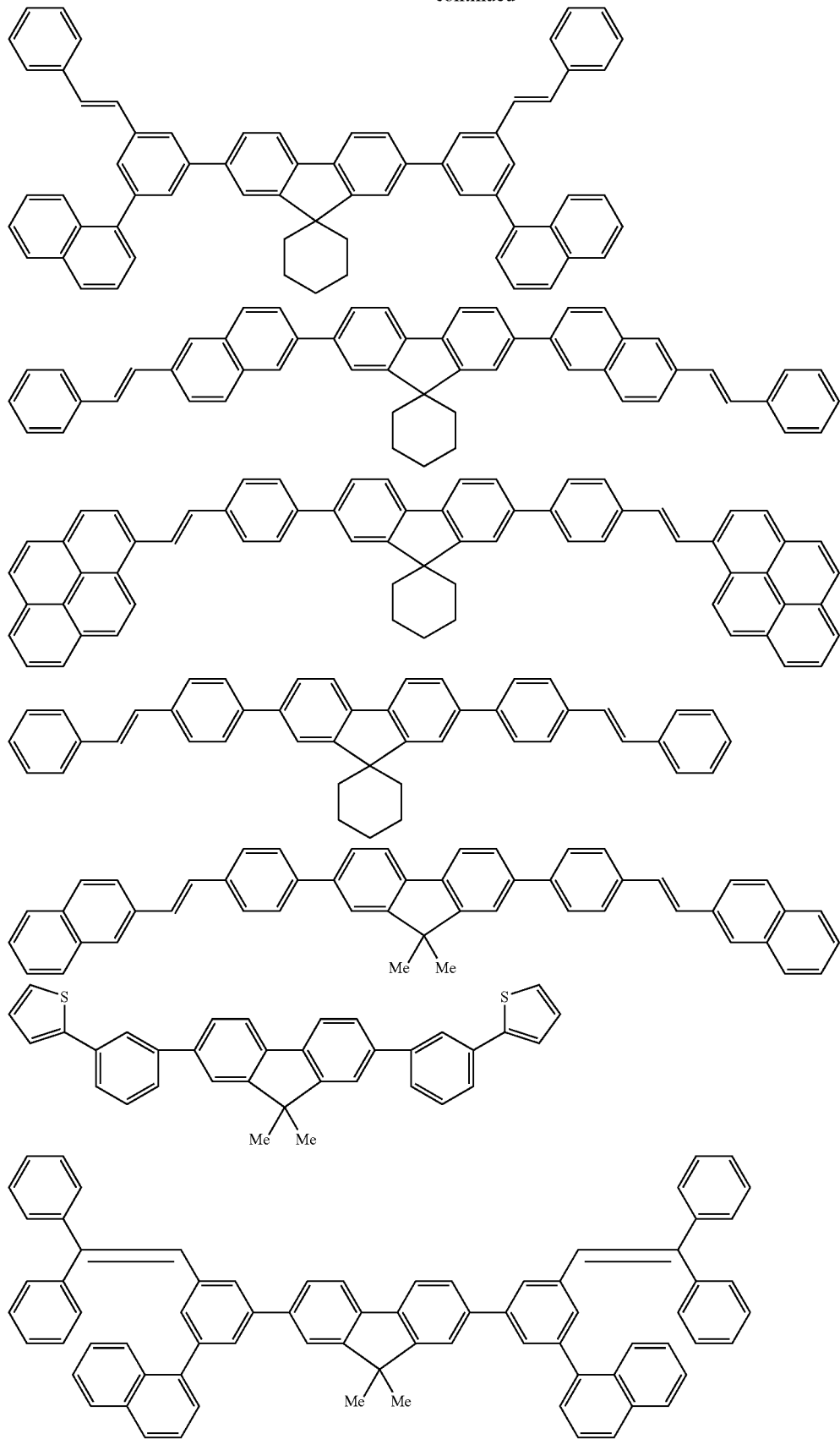

-continued
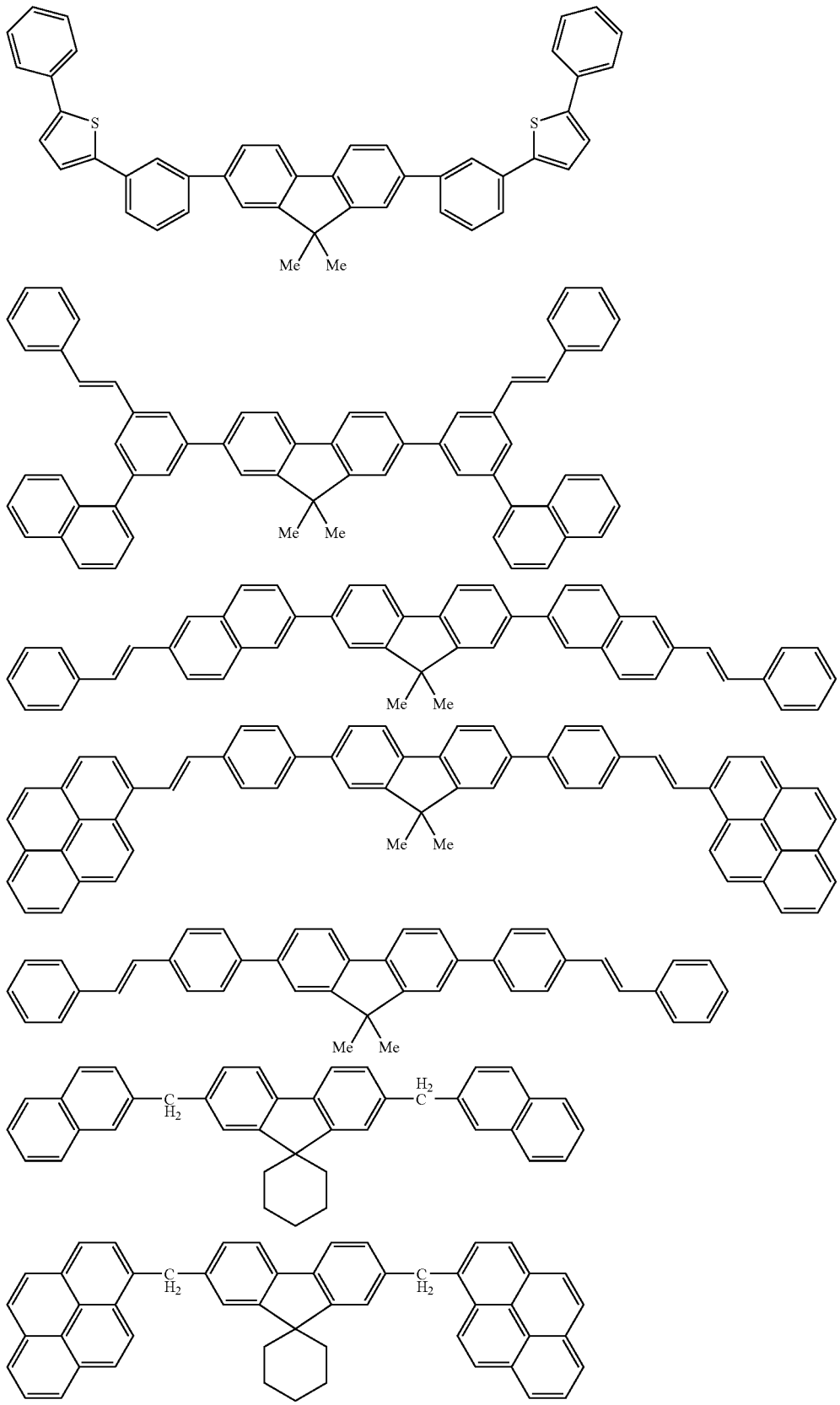

-continued
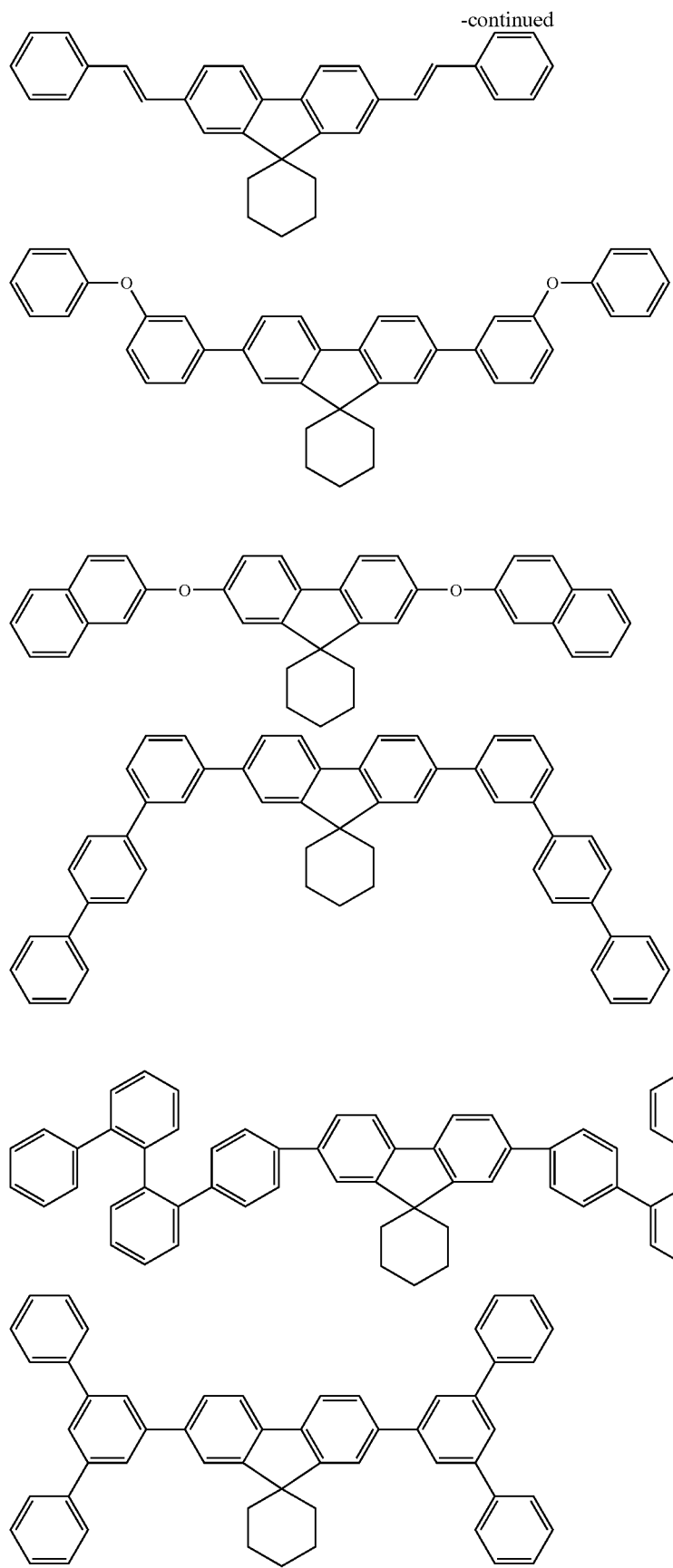

-continued
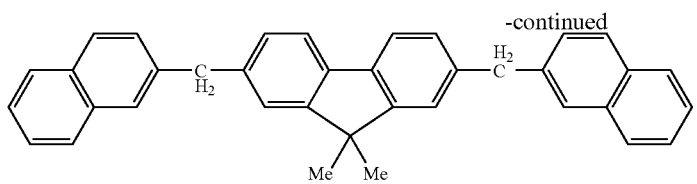
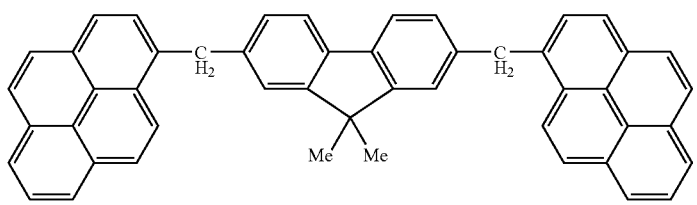
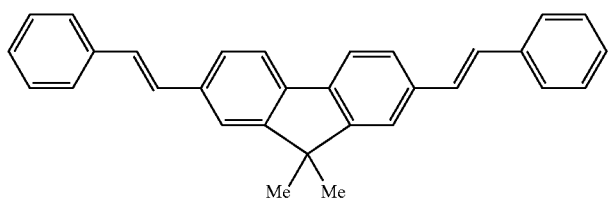
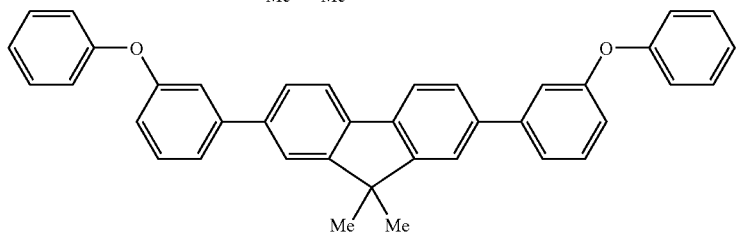
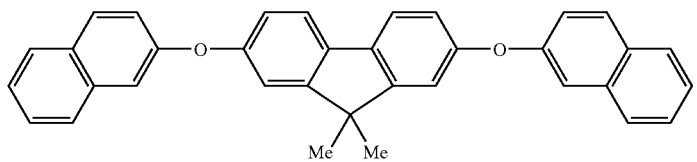
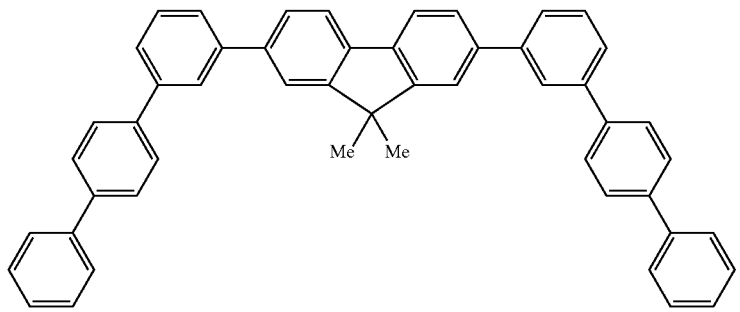
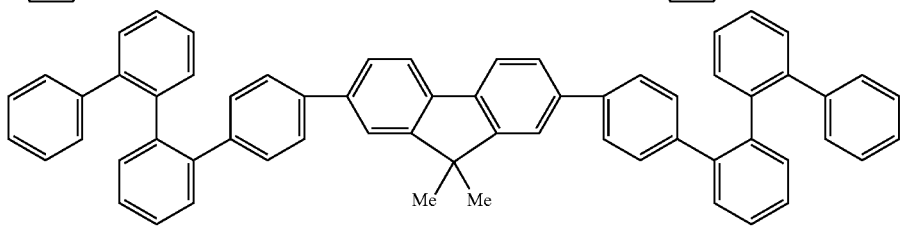

-continued
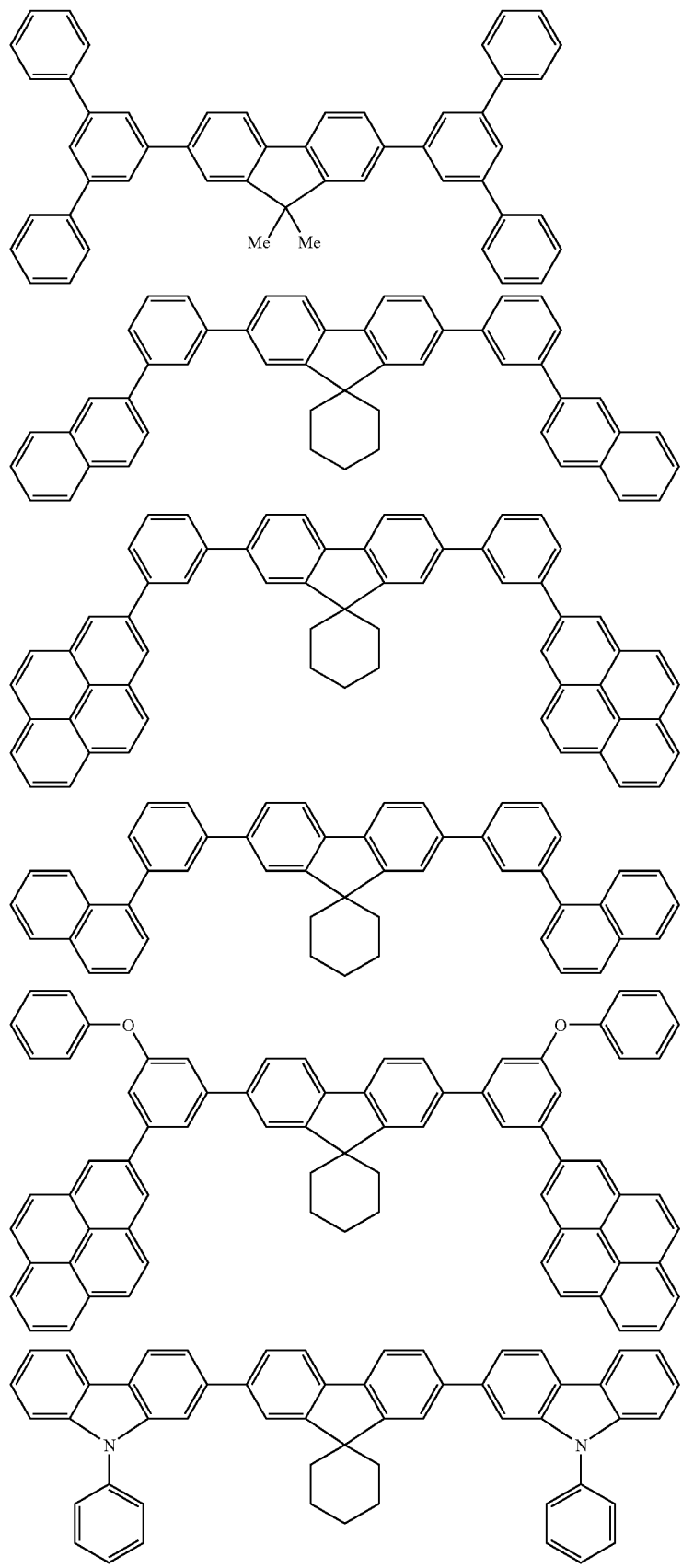

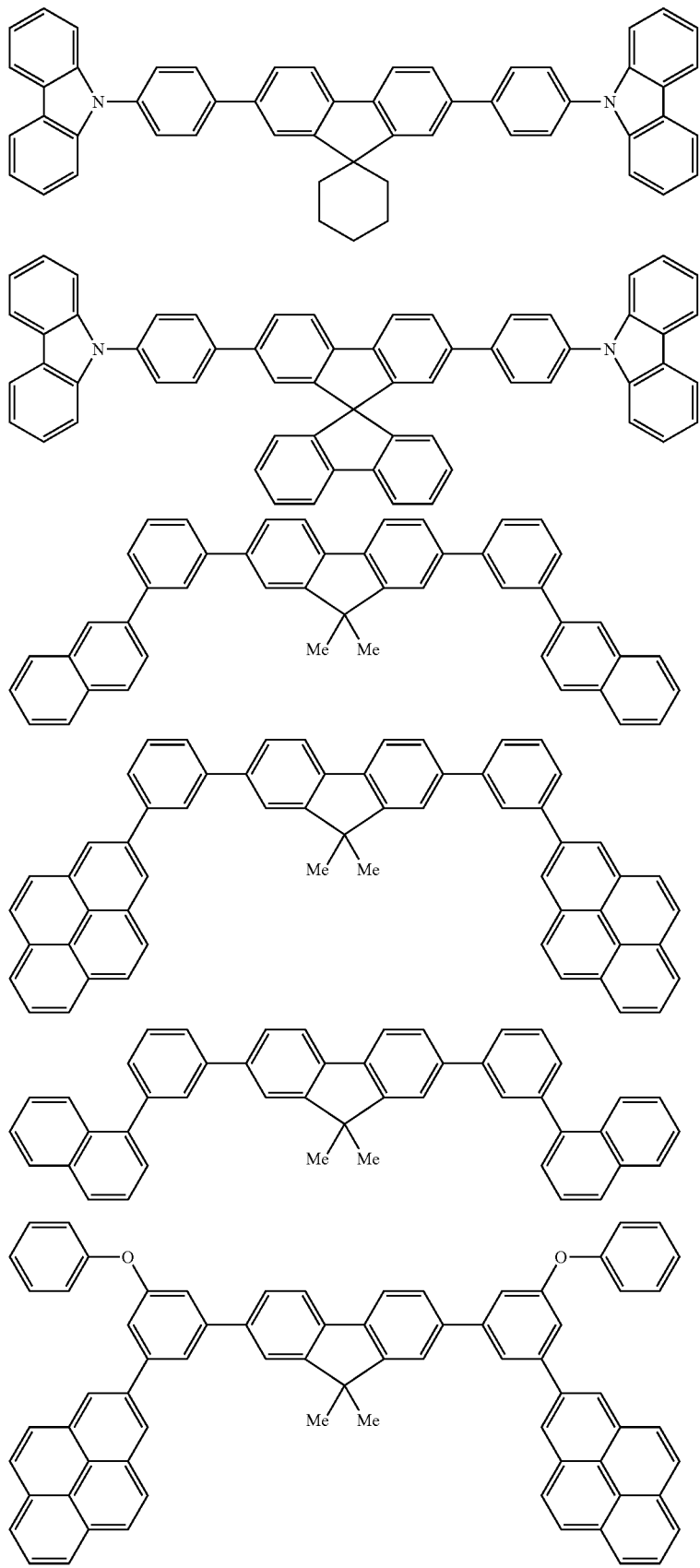

-continued
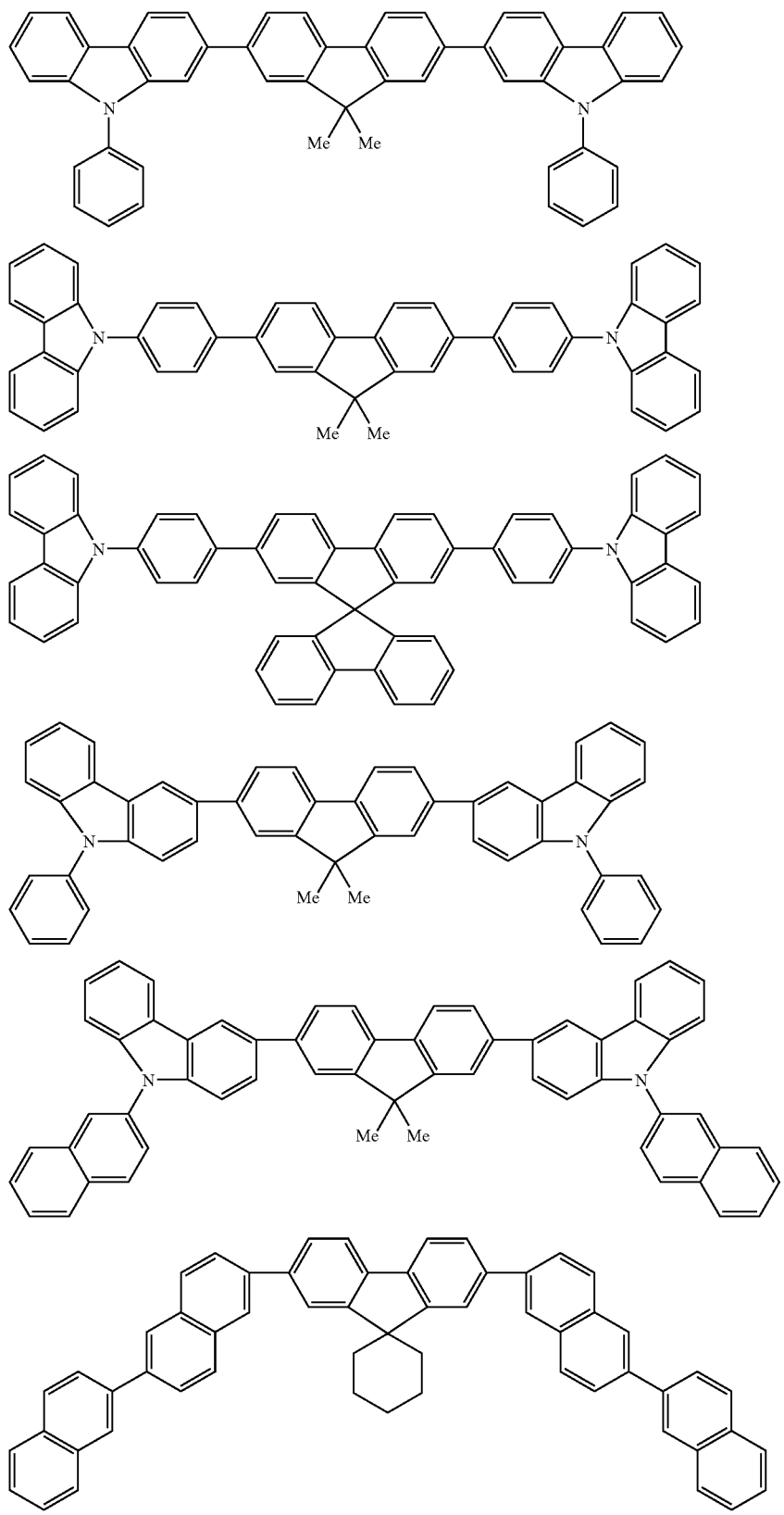

-continued
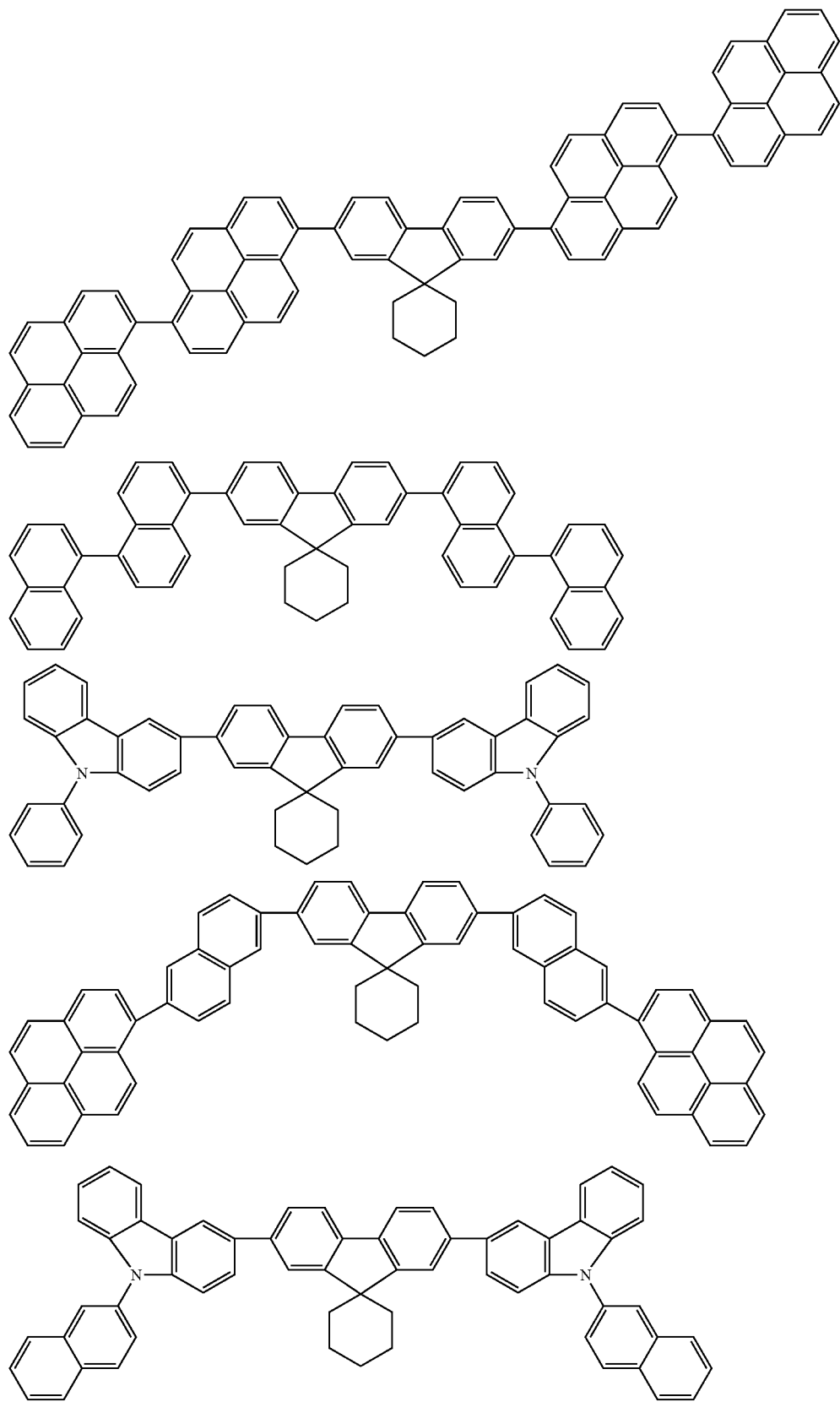

-continued
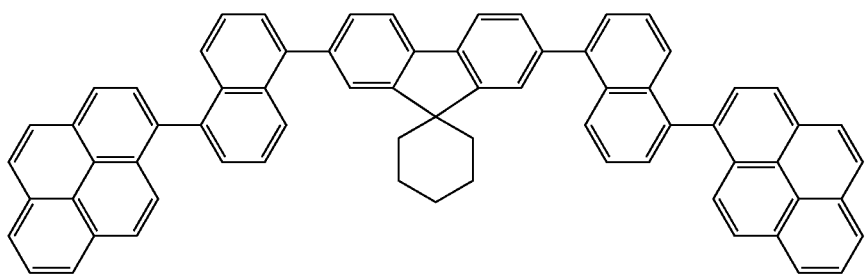
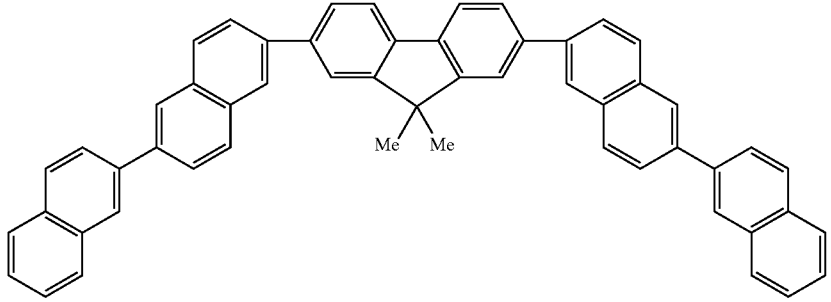
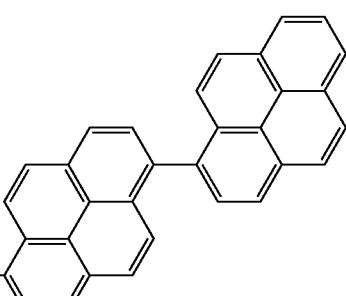
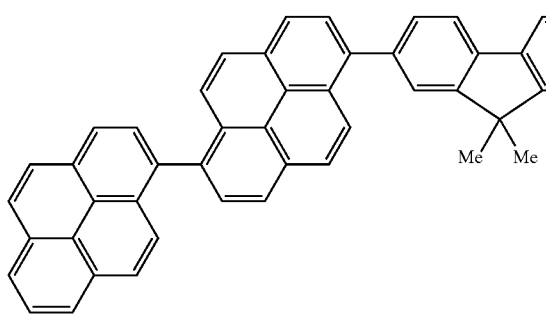
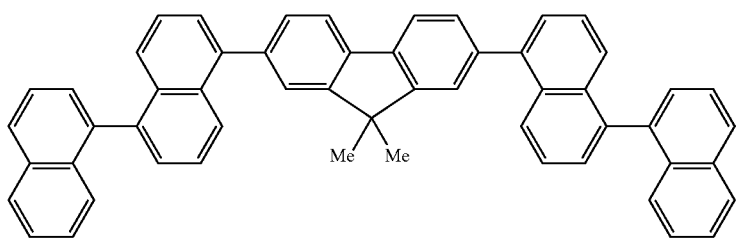
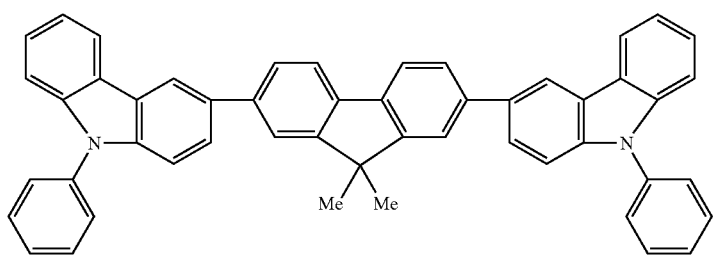

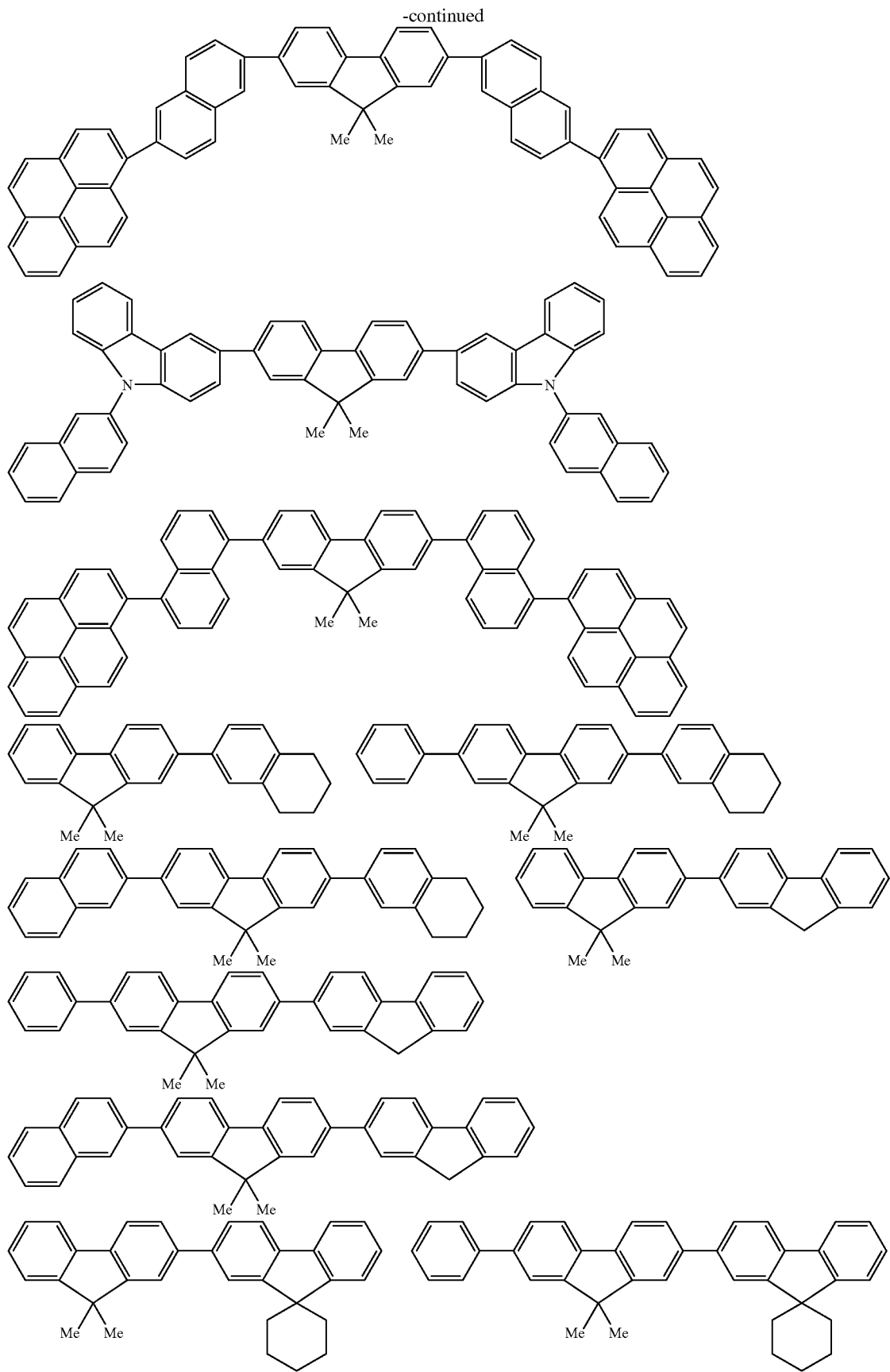

-continued
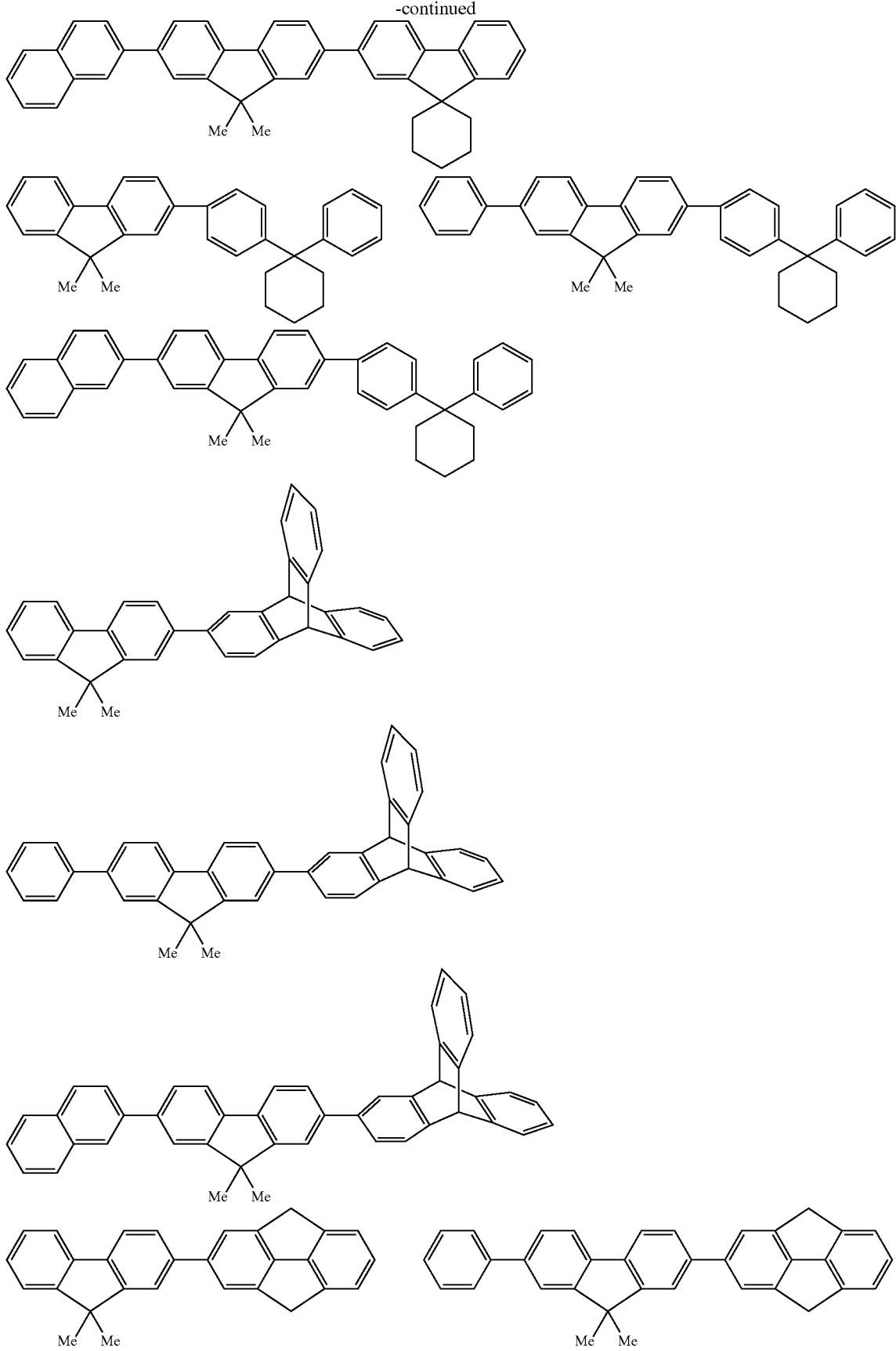

-continued
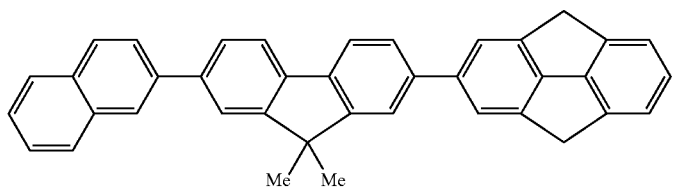
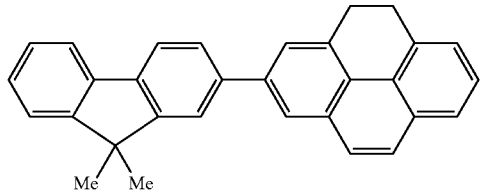
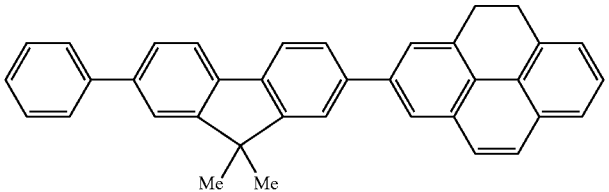
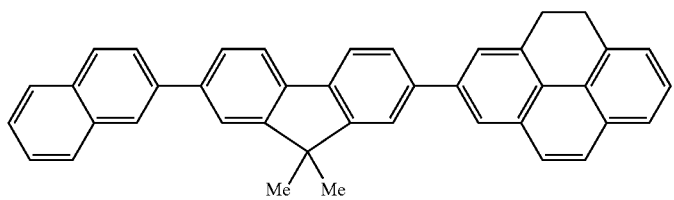
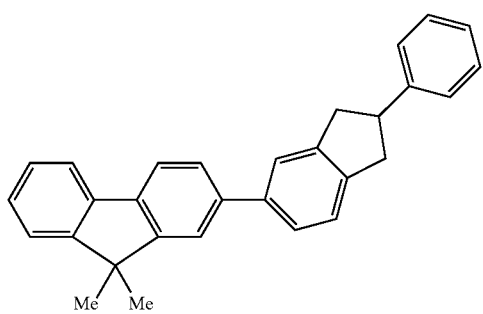
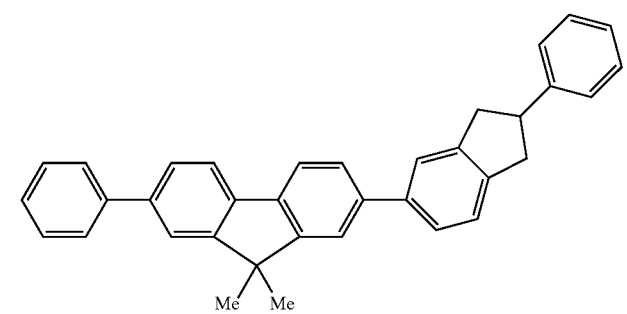
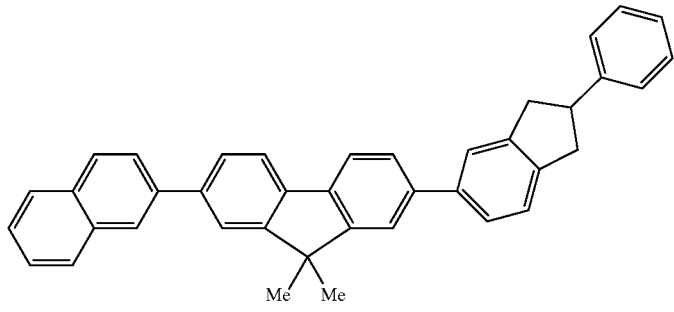
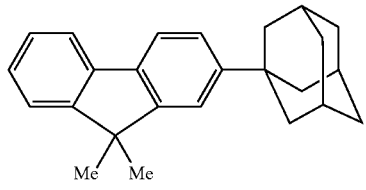
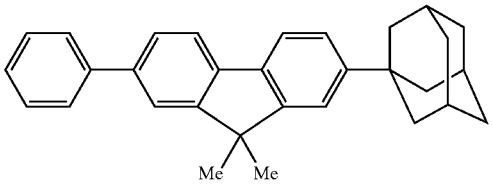
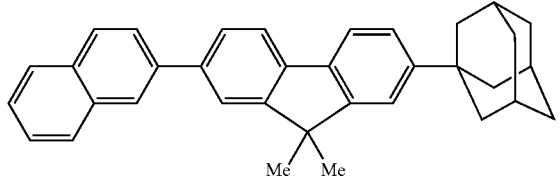
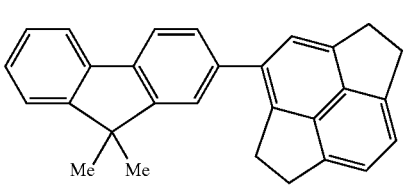

-continued
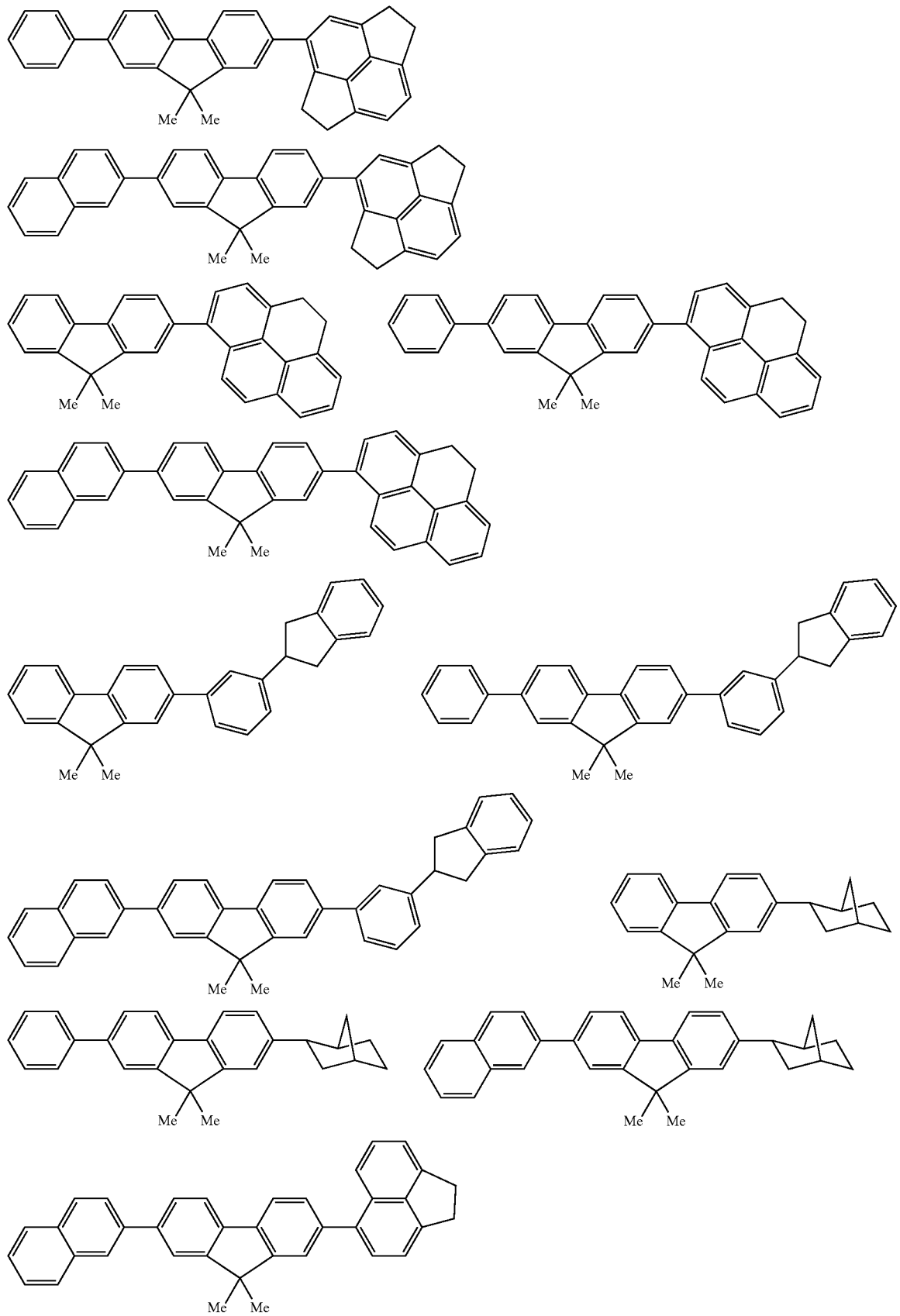

-continued
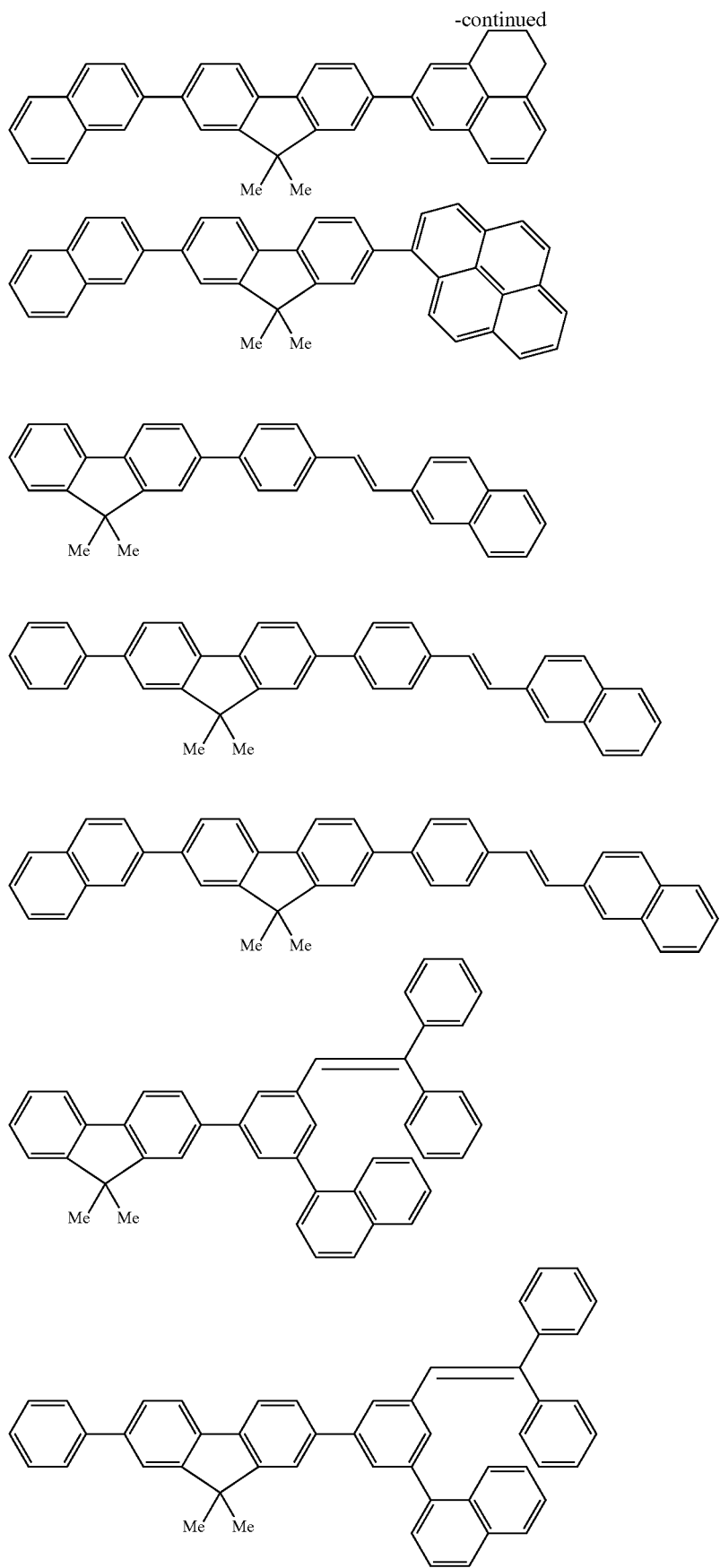

-continued
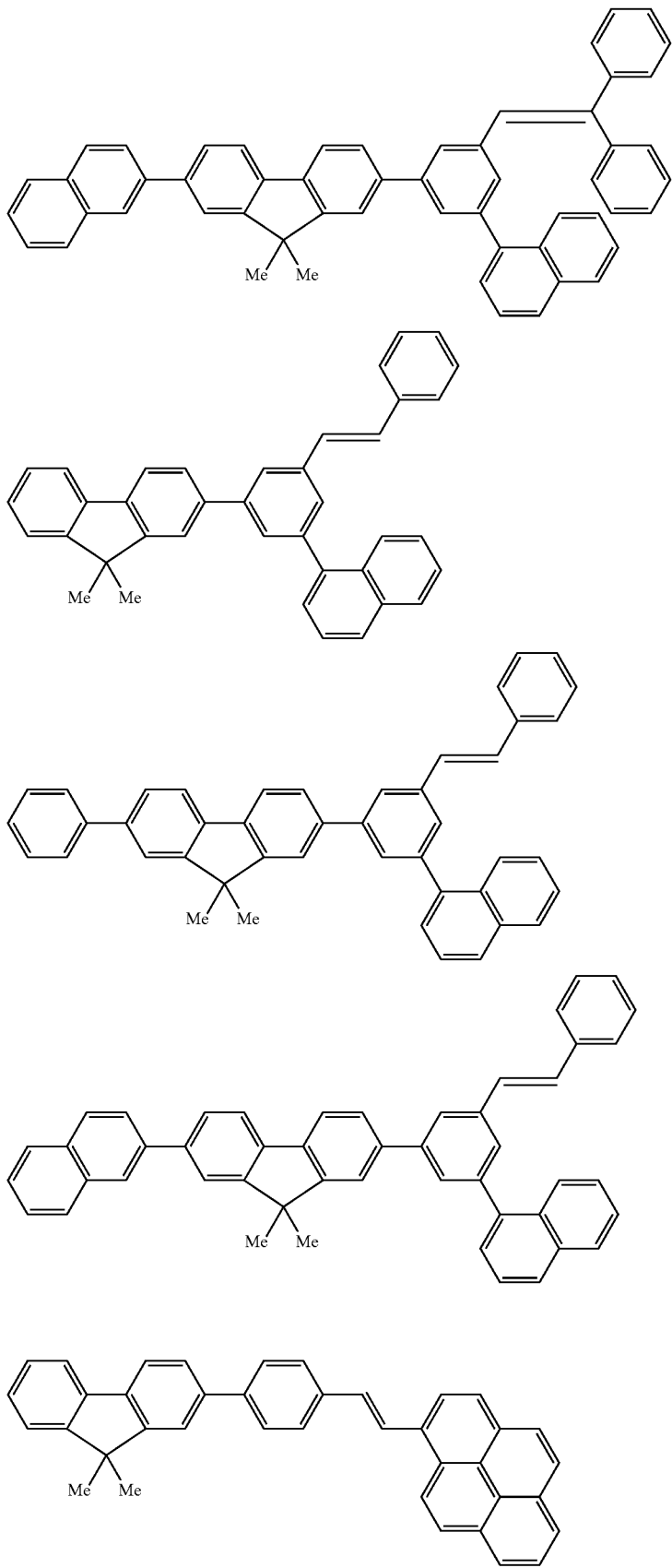

-continued
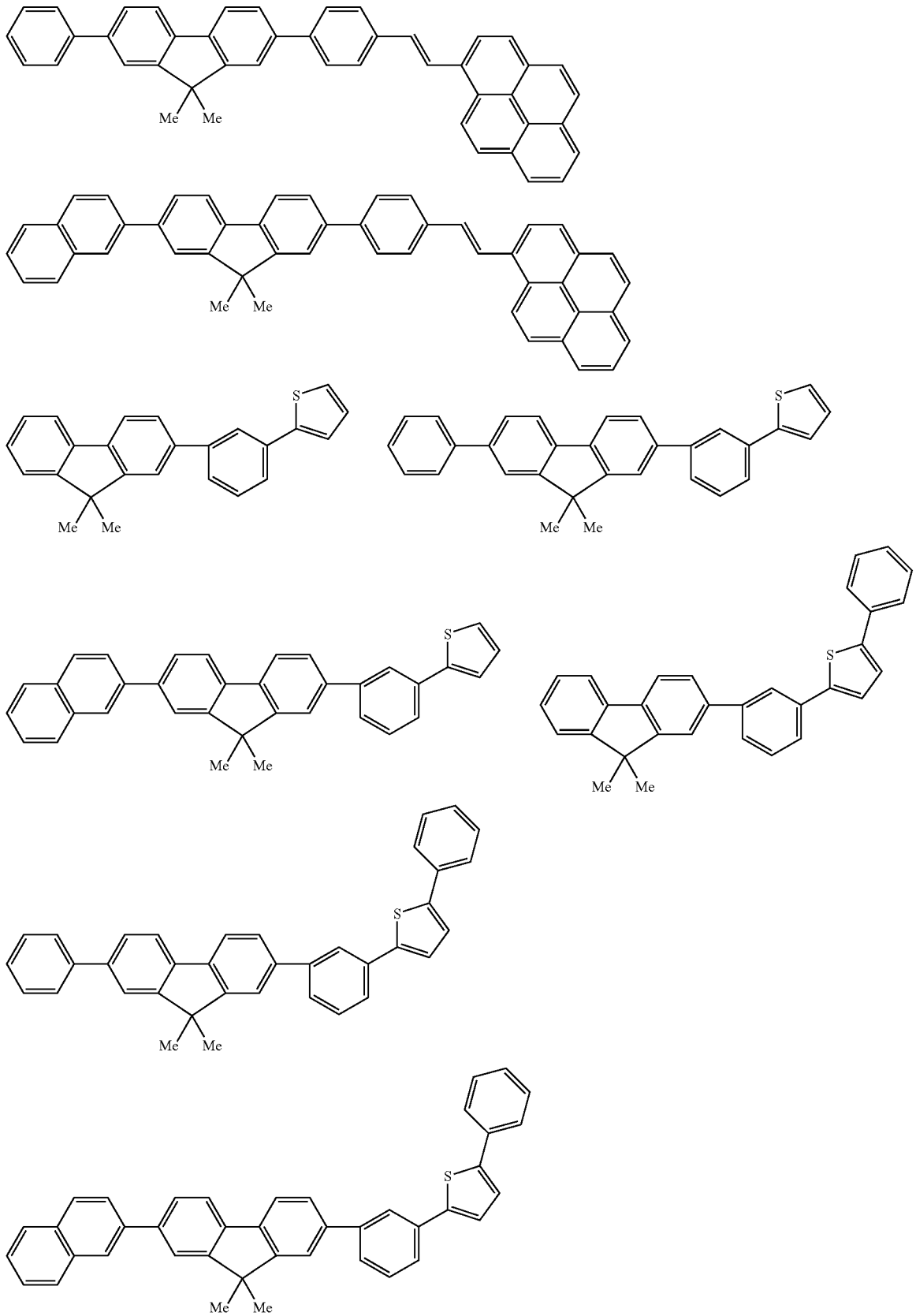

-continued
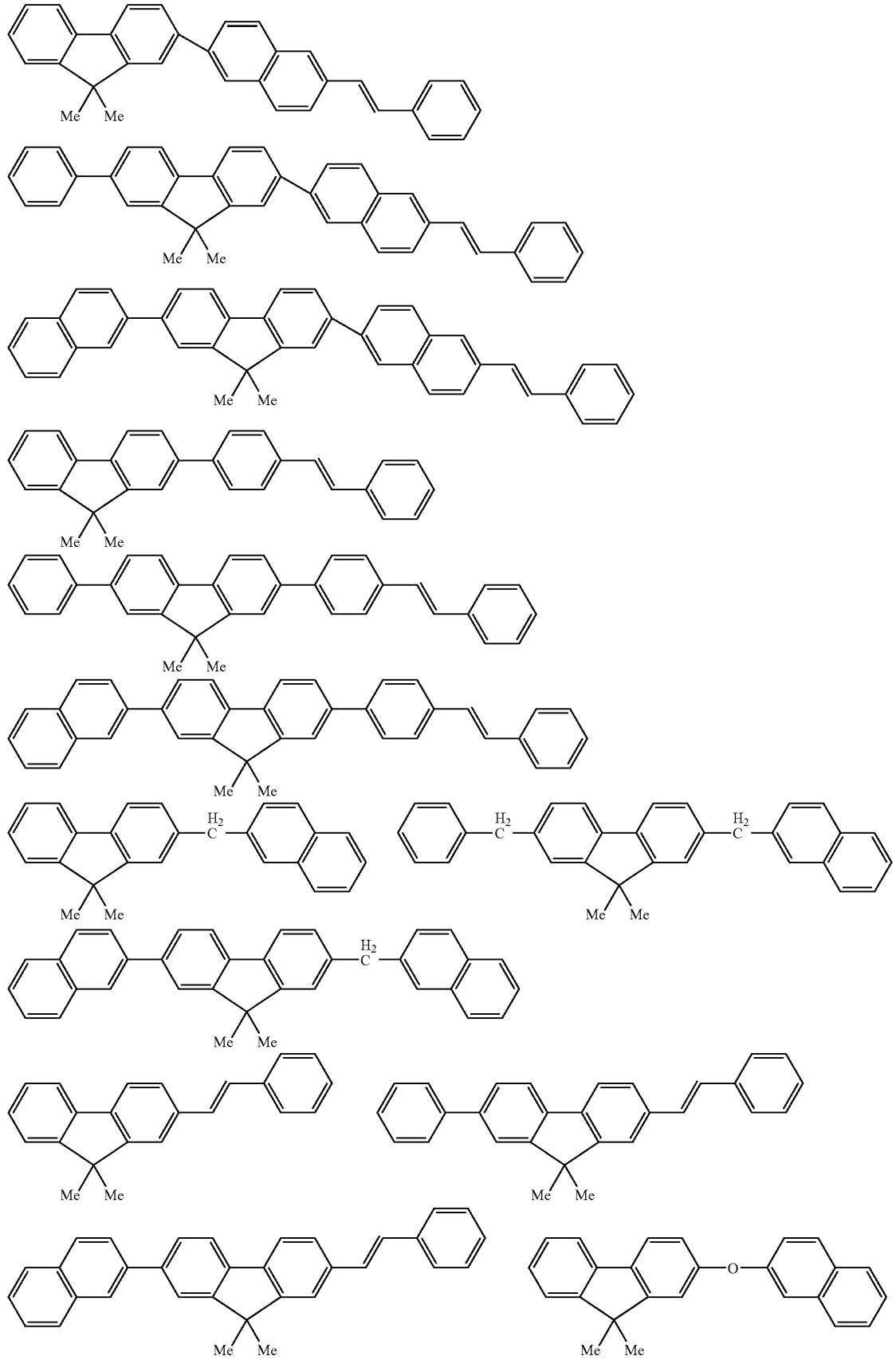

-continued
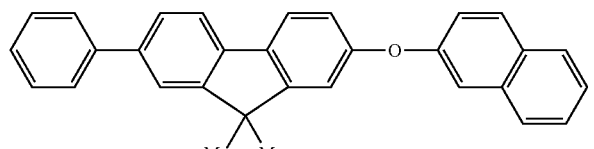
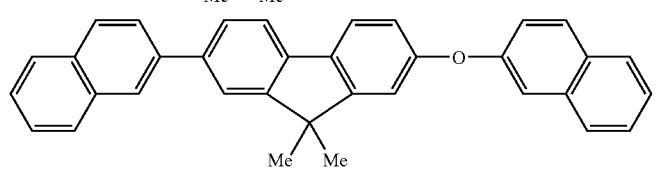
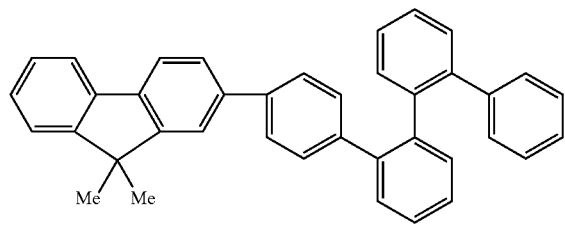
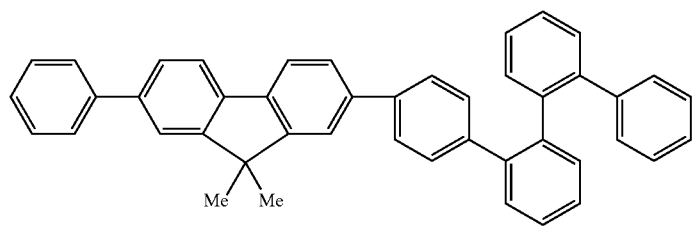
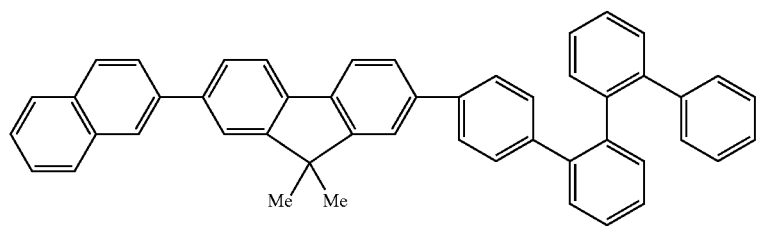
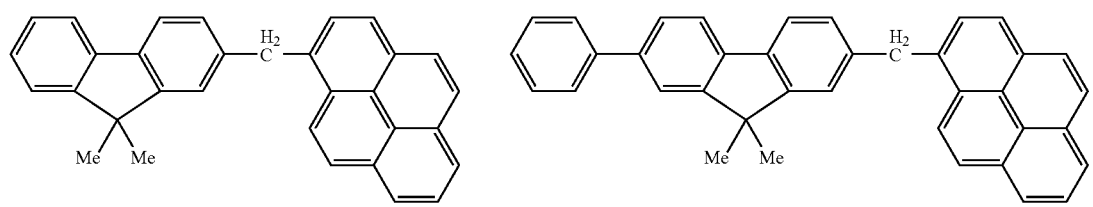
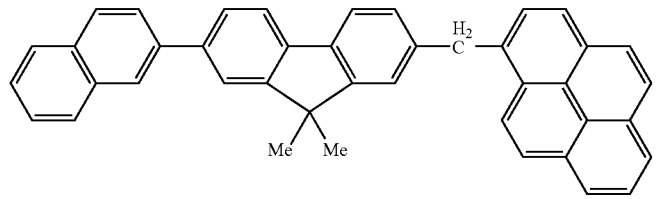
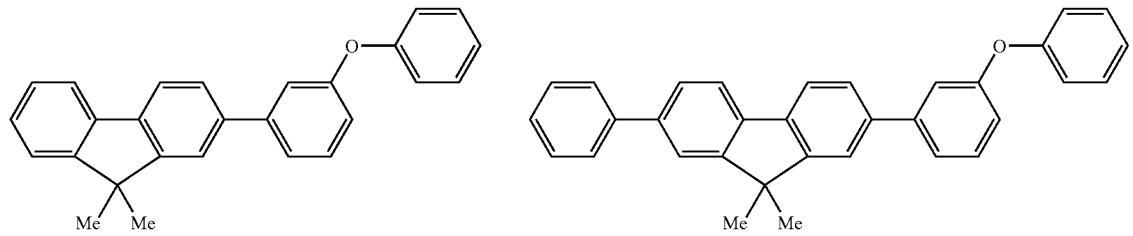

-continued
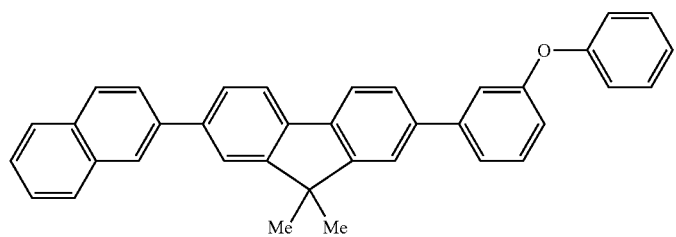
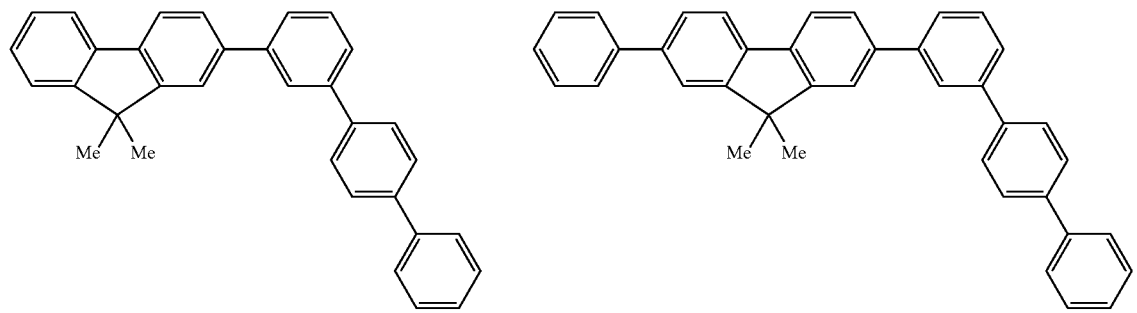
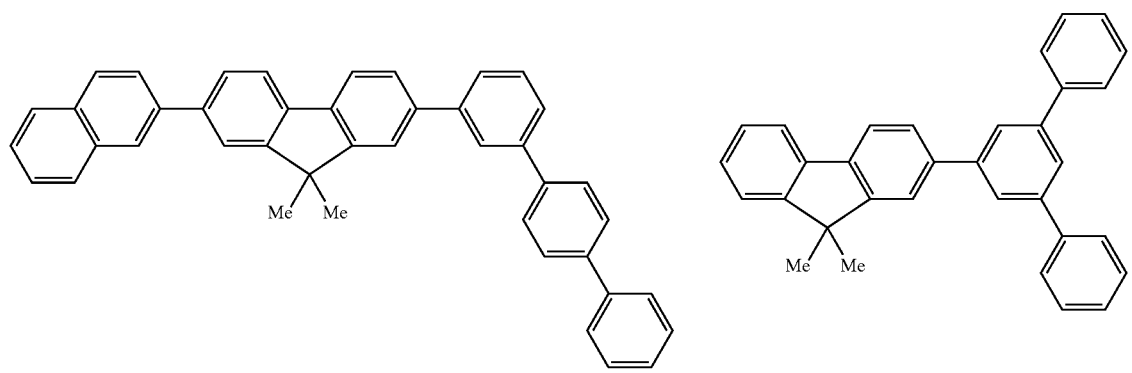
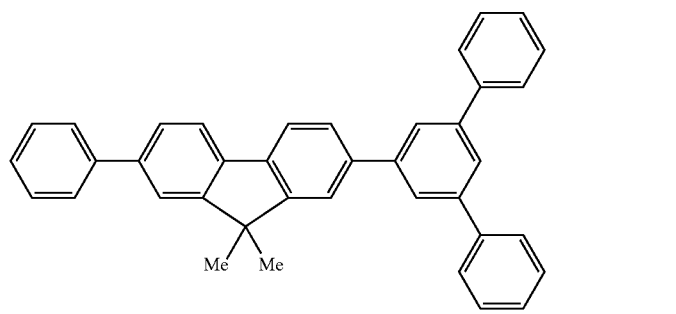
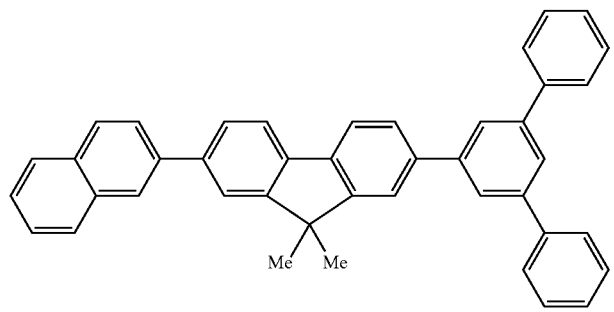

-continued
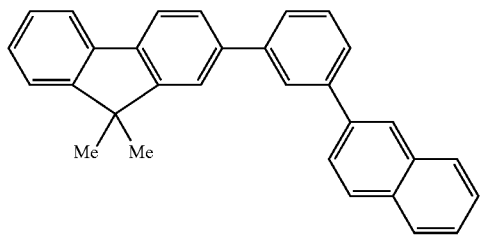
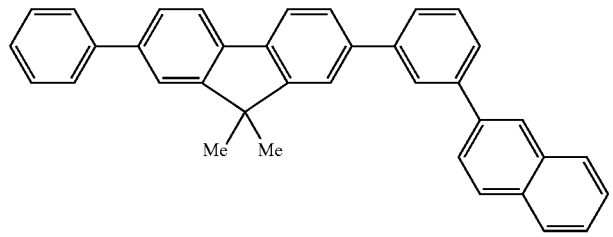
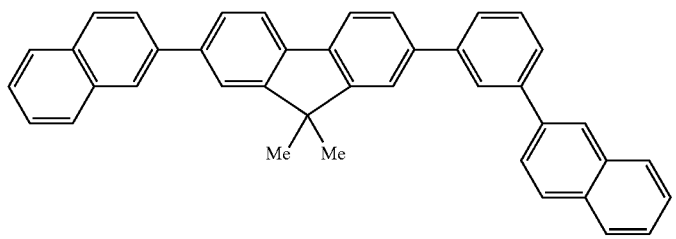
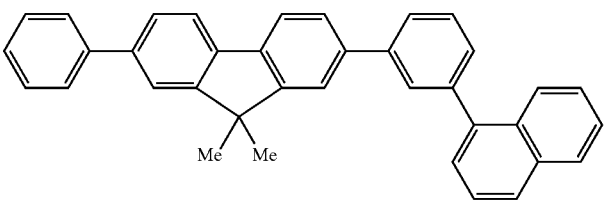
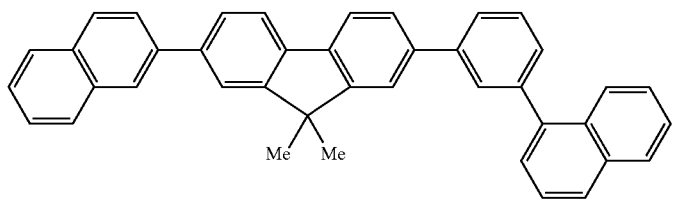
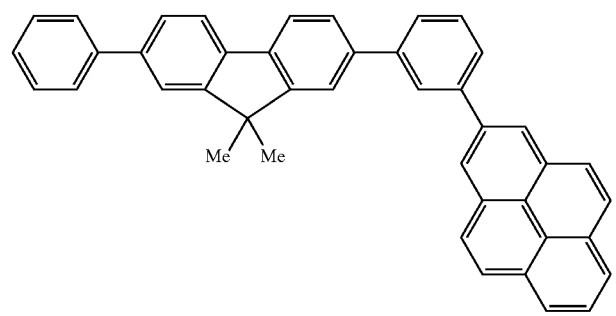
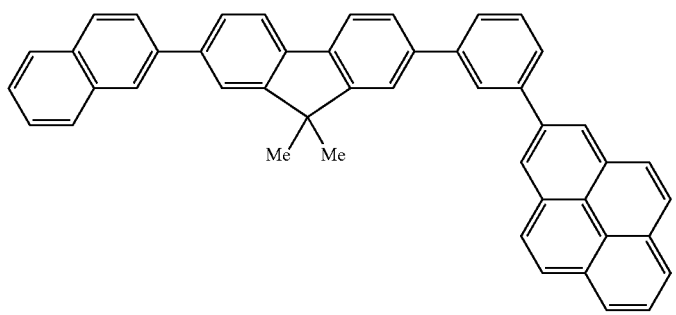

-continued
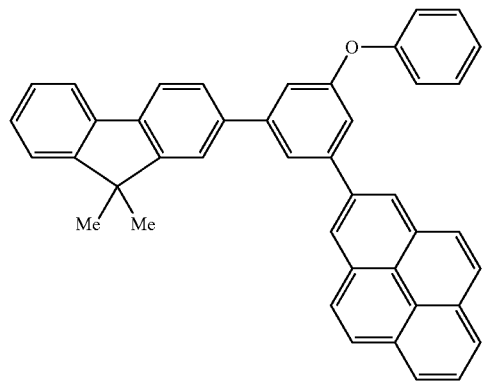
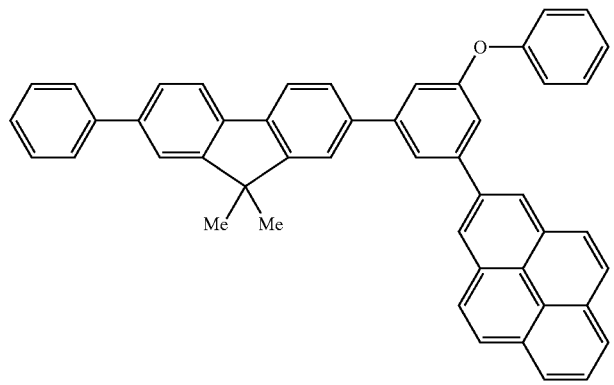
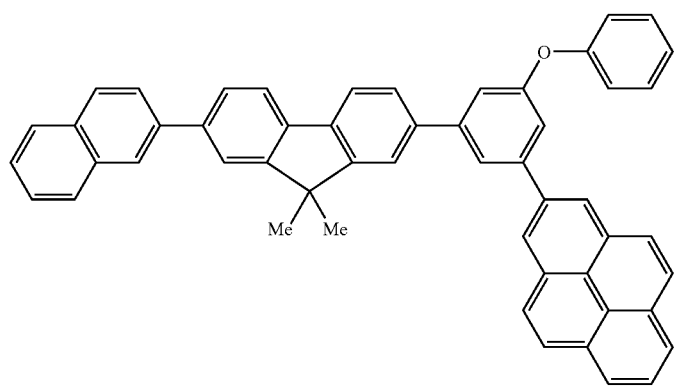
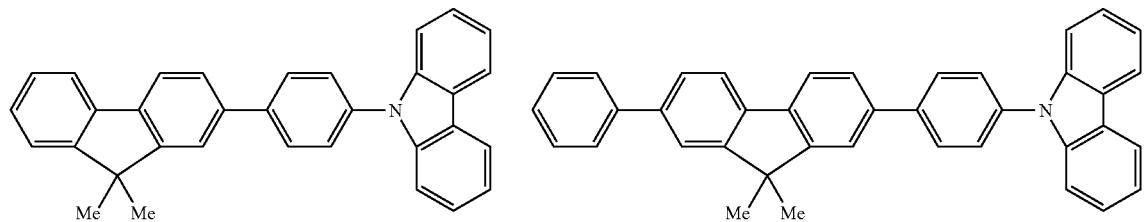
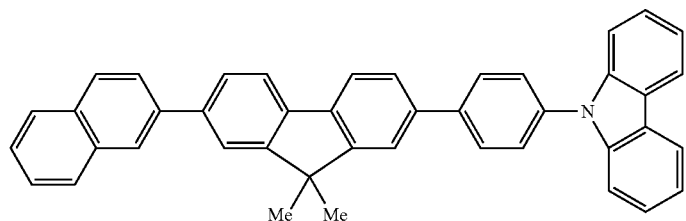
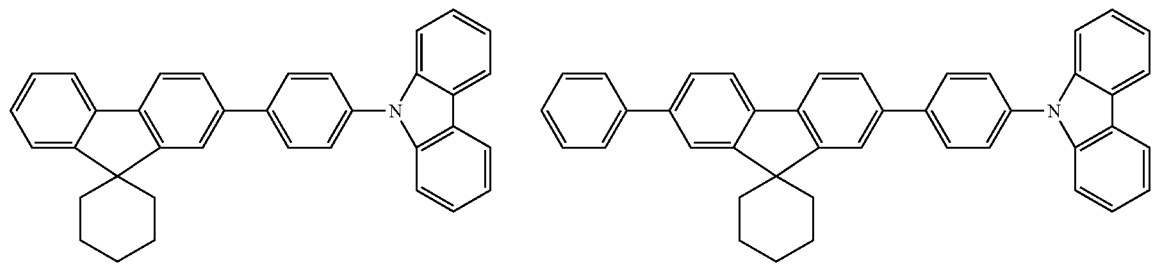

-continued
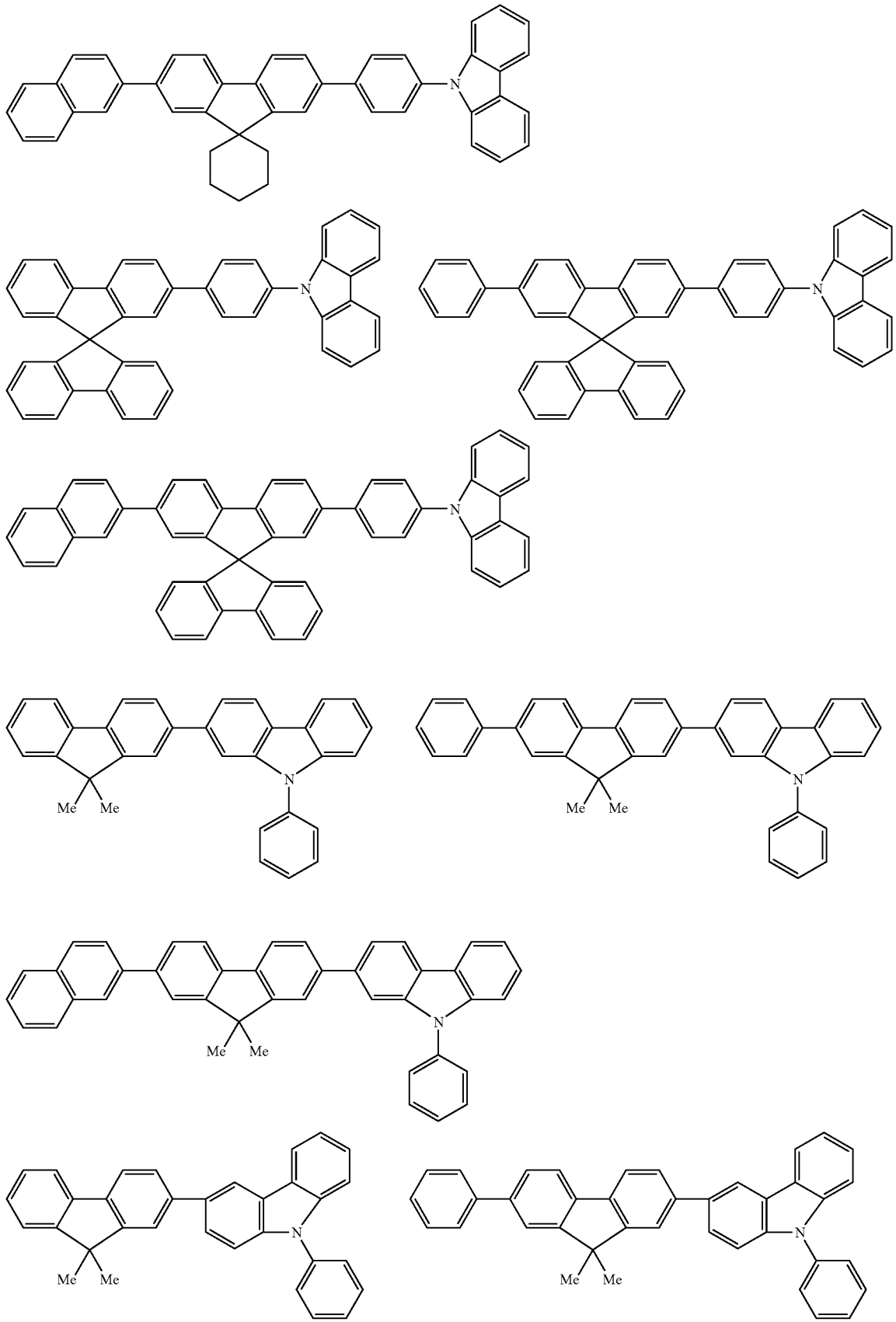

-continued
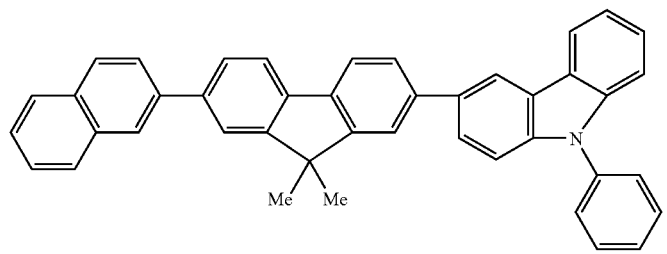
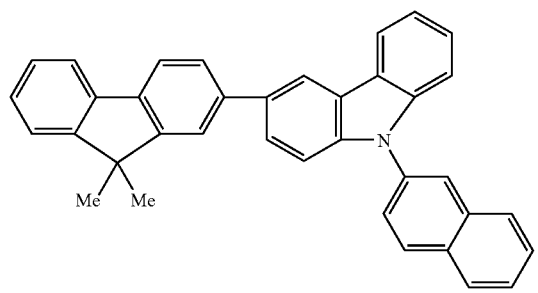
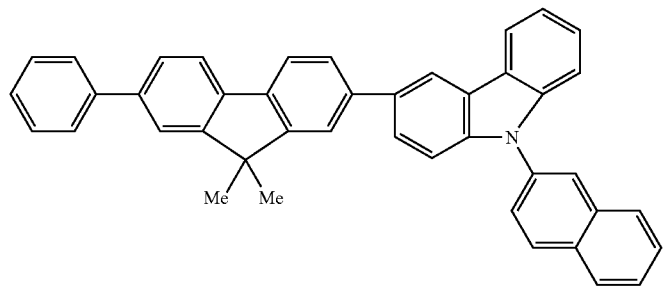
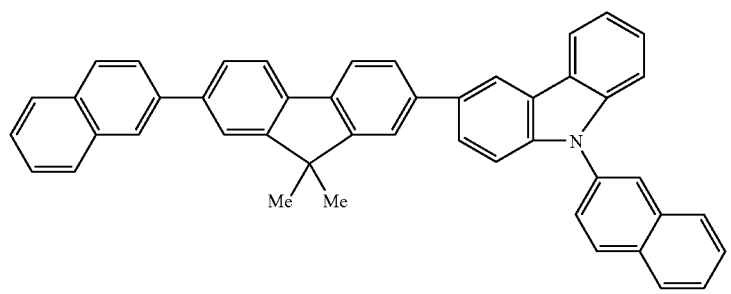
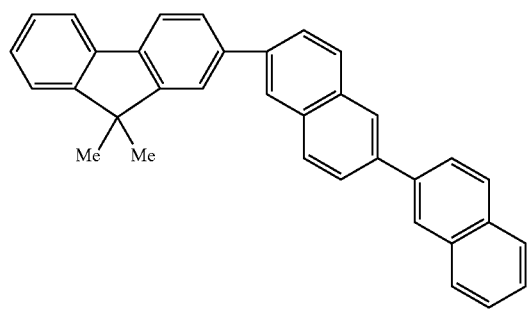

-continued
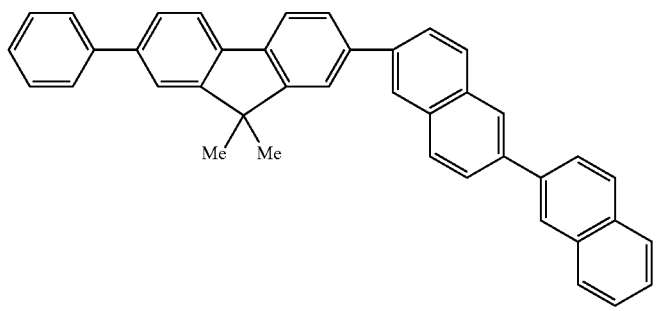
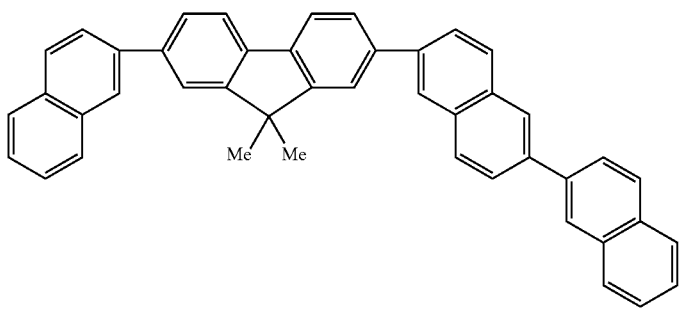
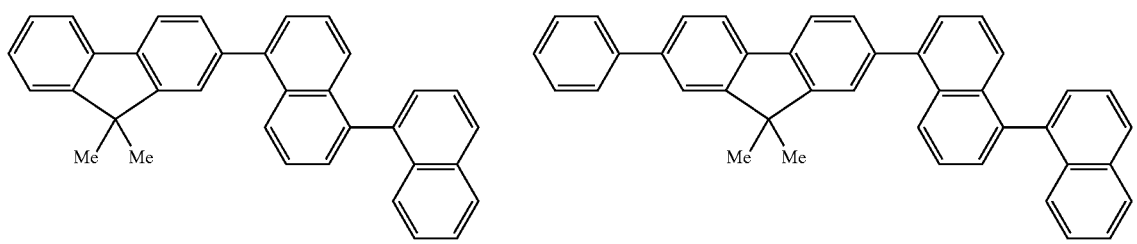
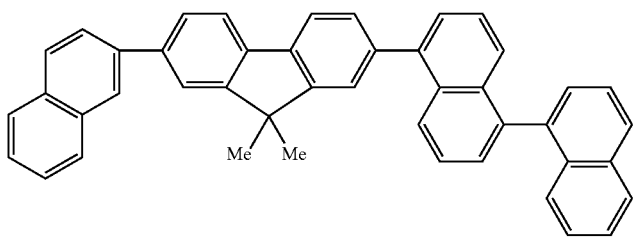
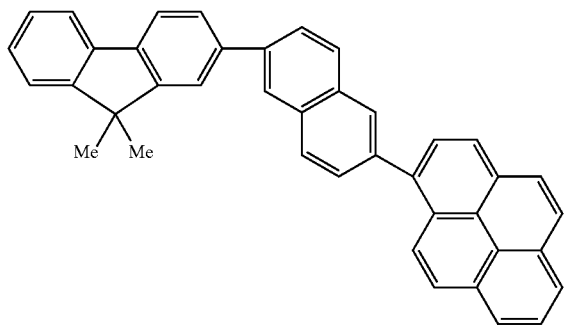

-continued
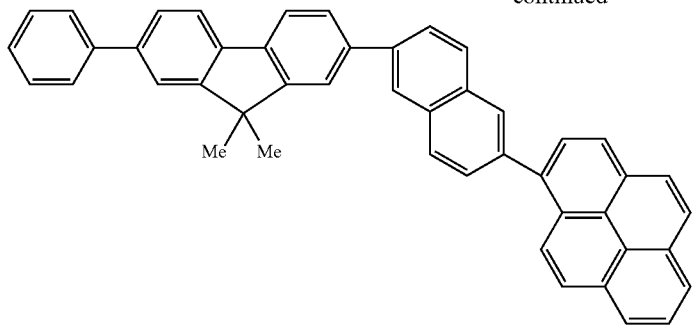
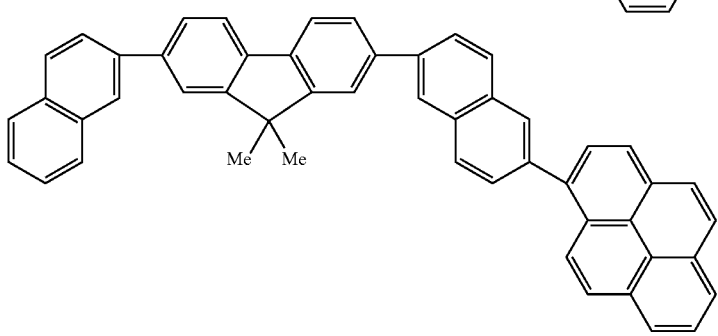
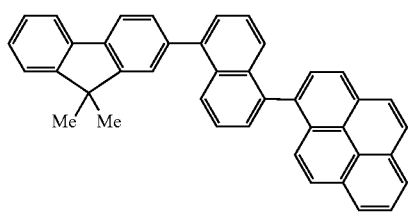
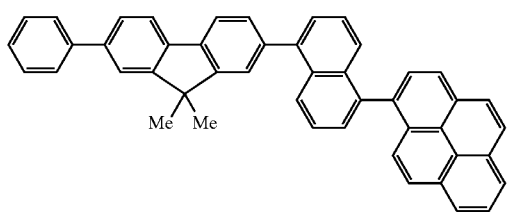
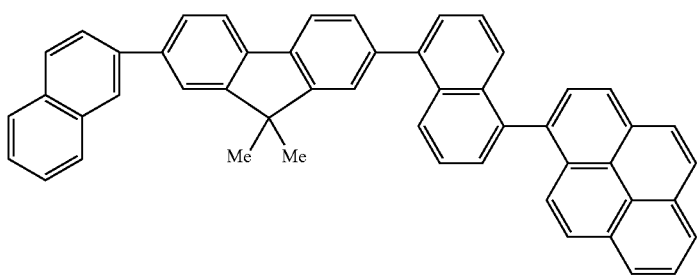
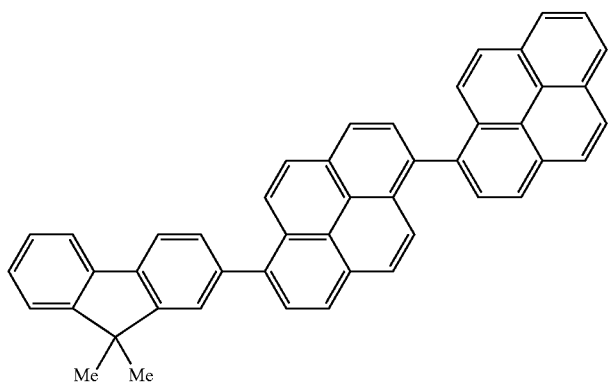

-continued
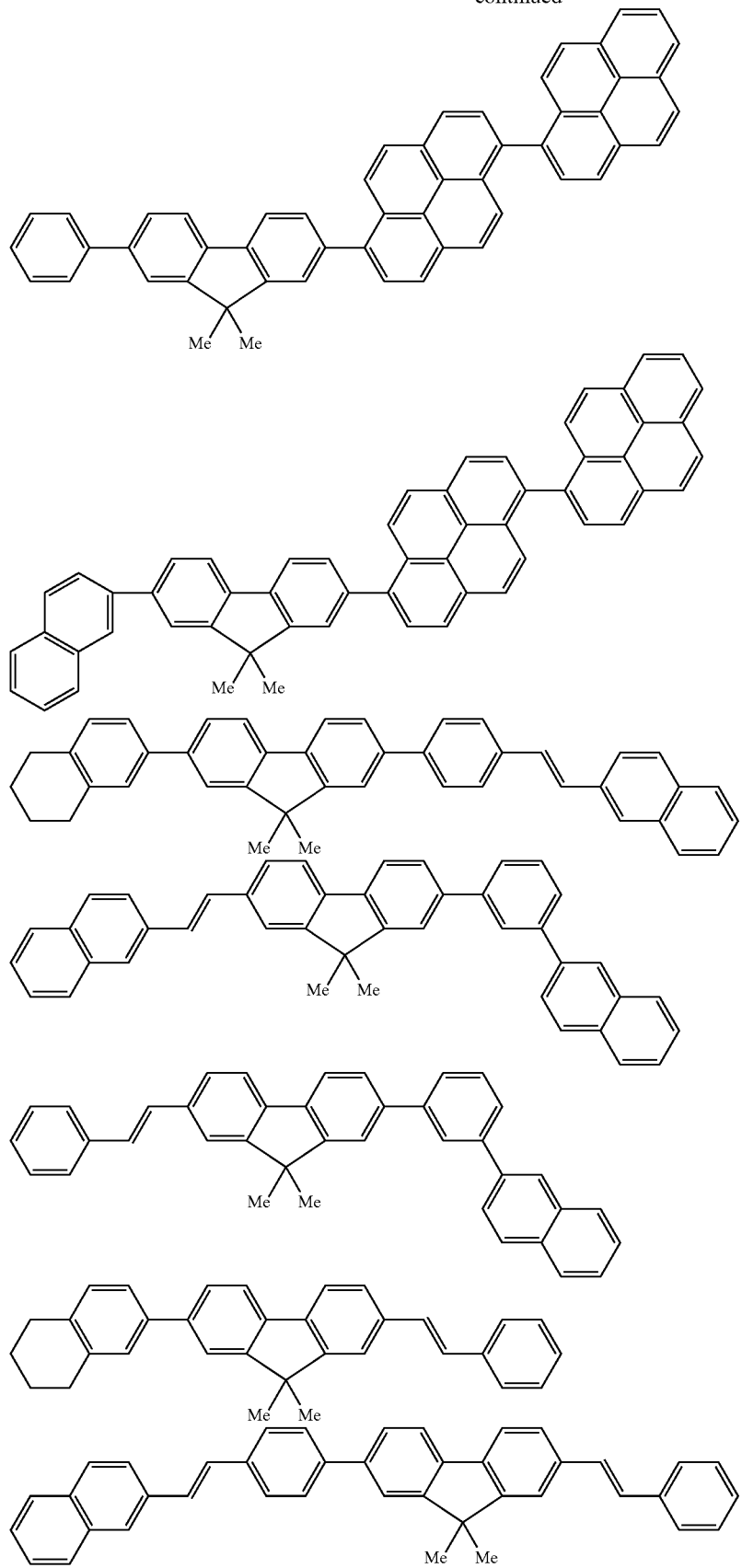

-continued
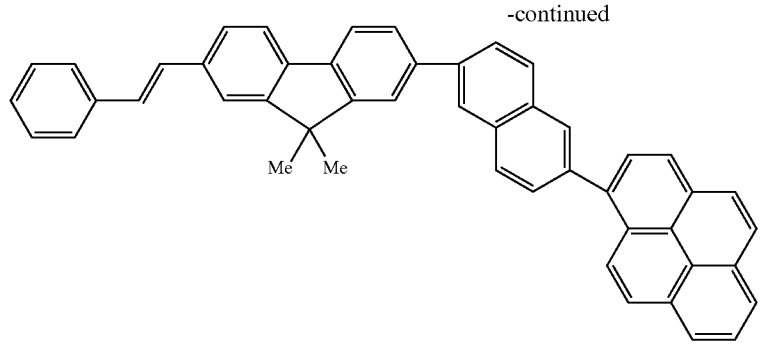
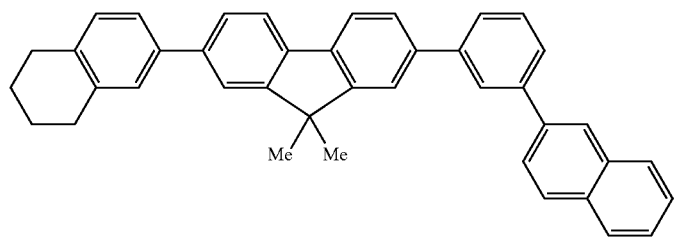
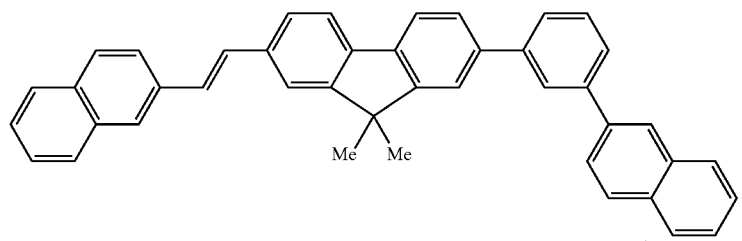
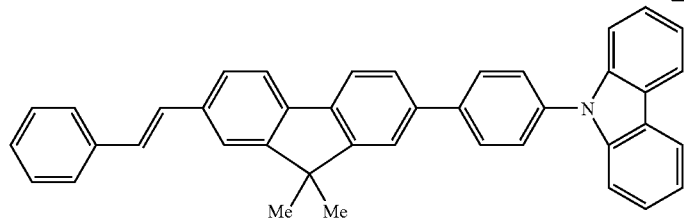
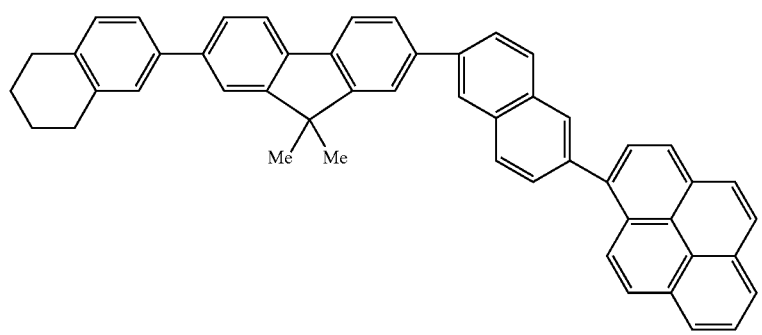
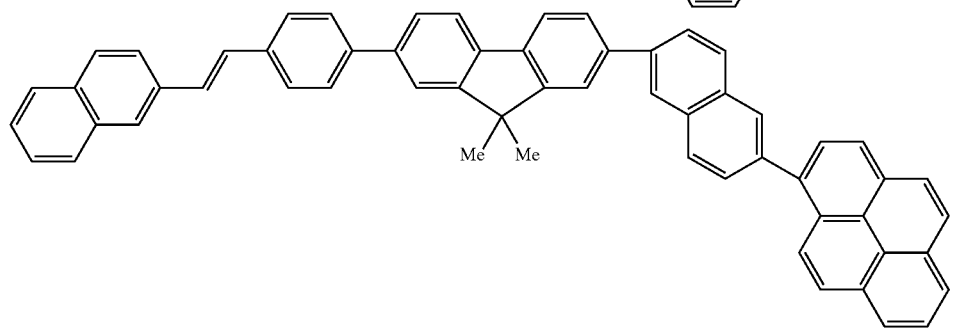

-continued
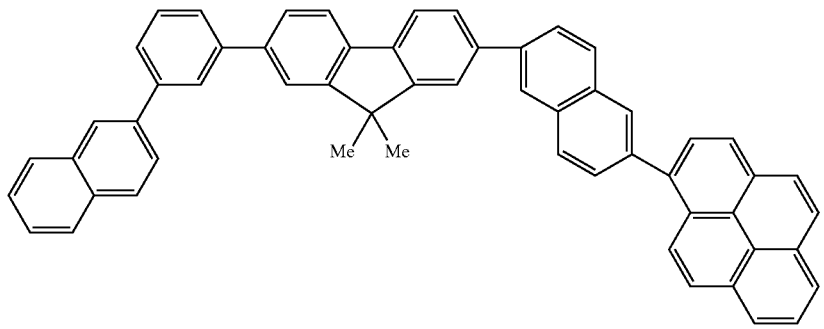
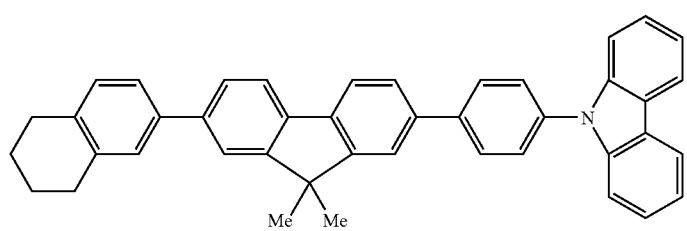
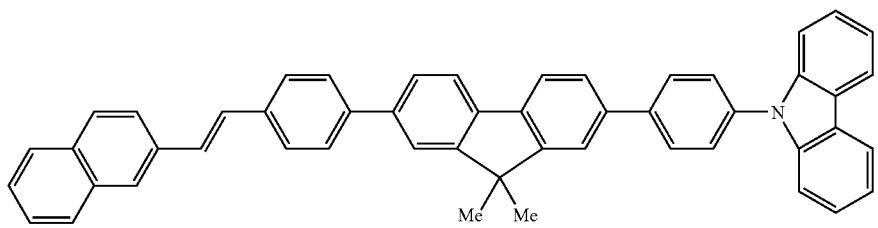
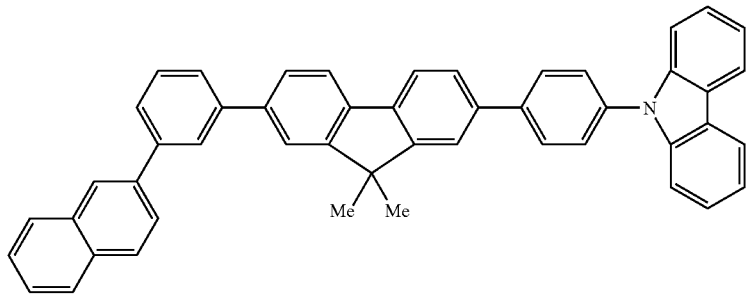
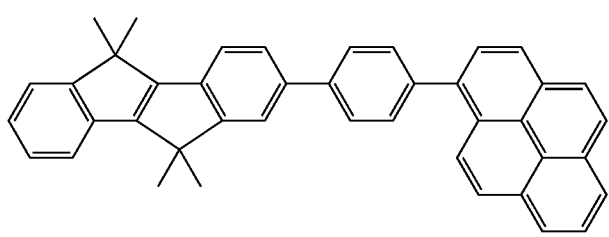
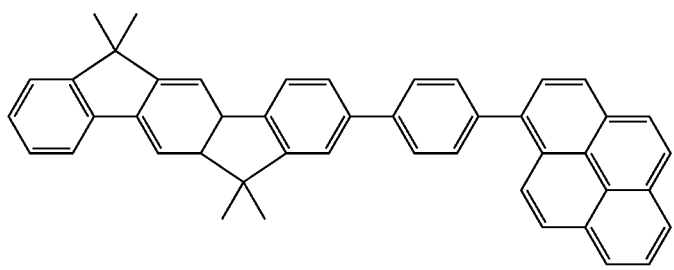

-continued
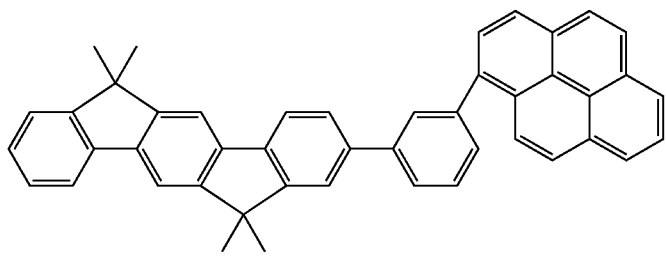
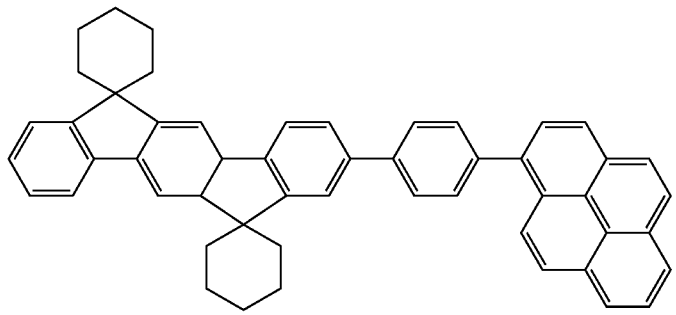
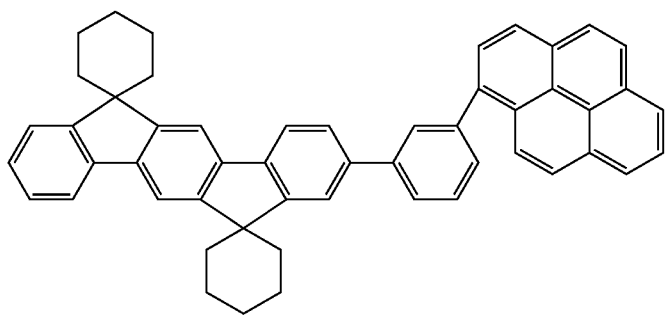
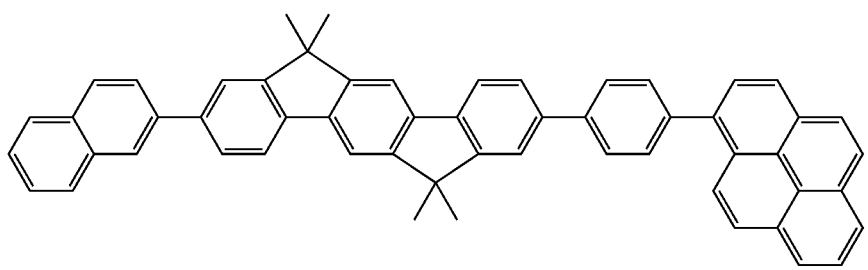
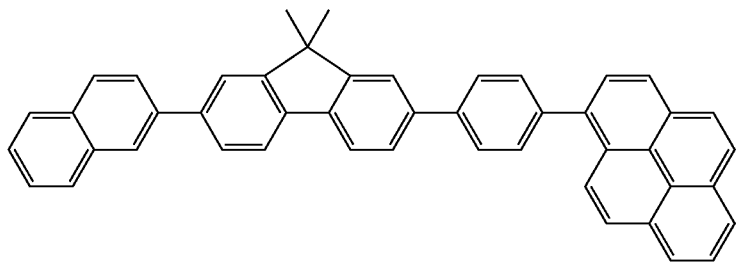
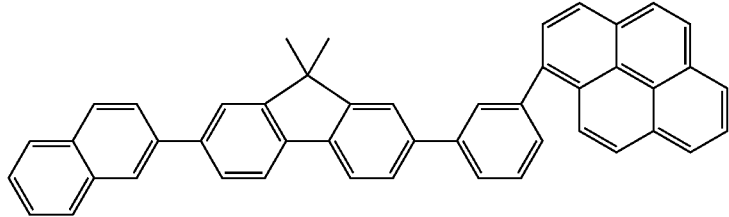

-continued
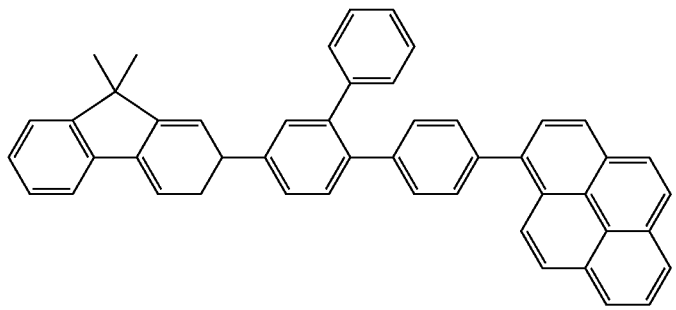
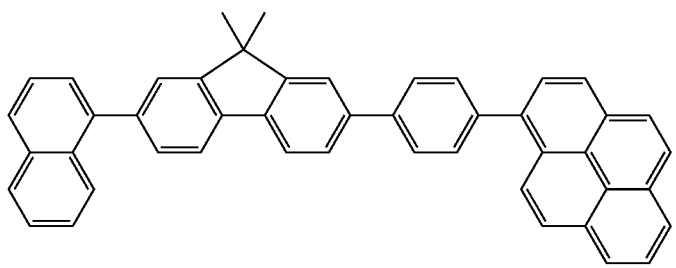
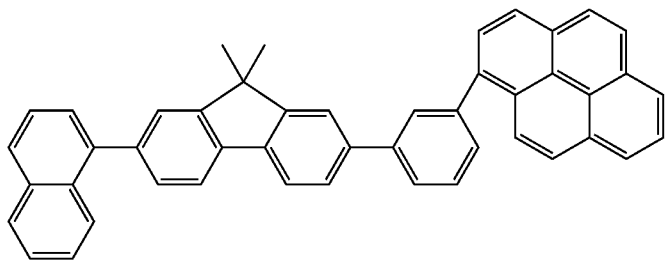
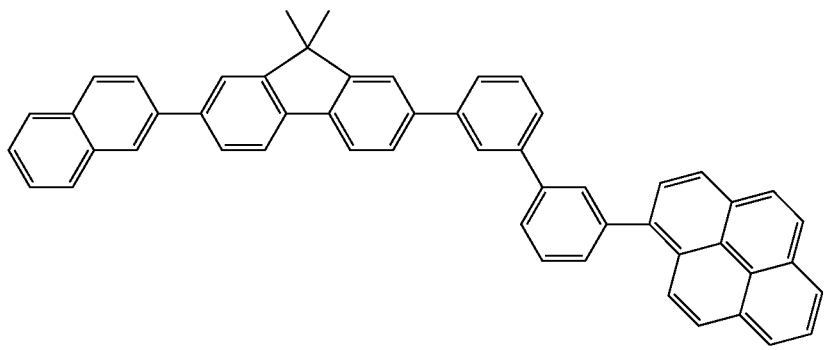
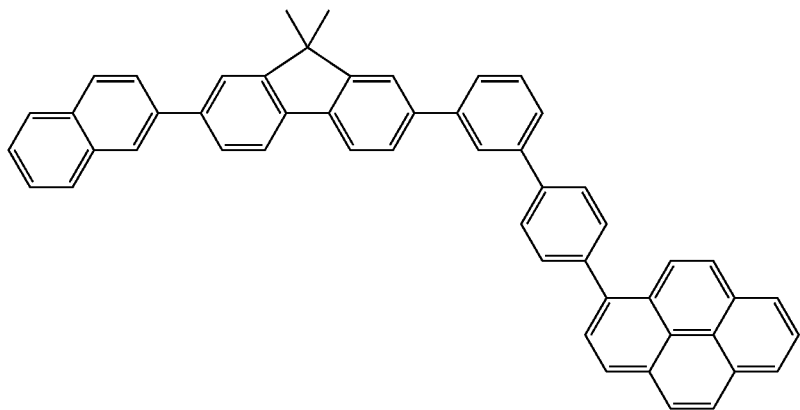

-continued
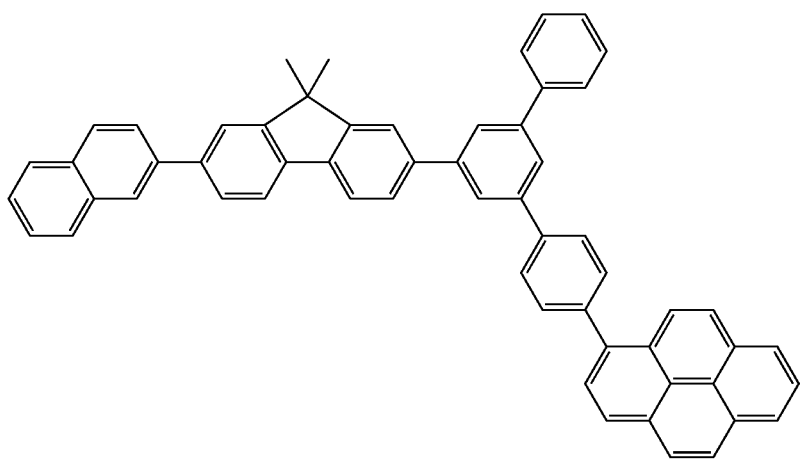
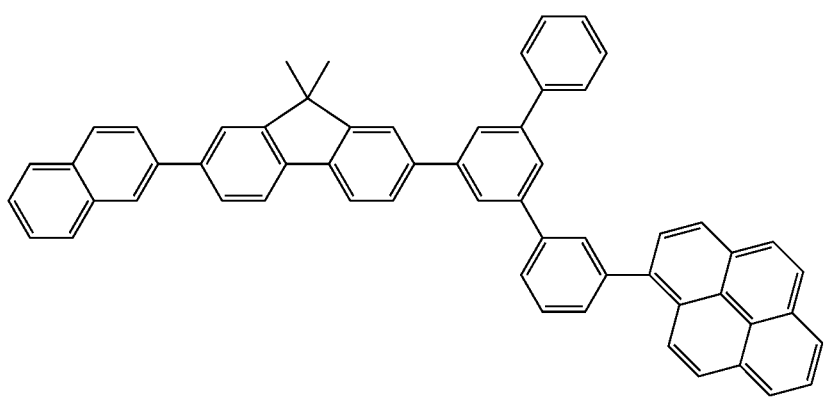
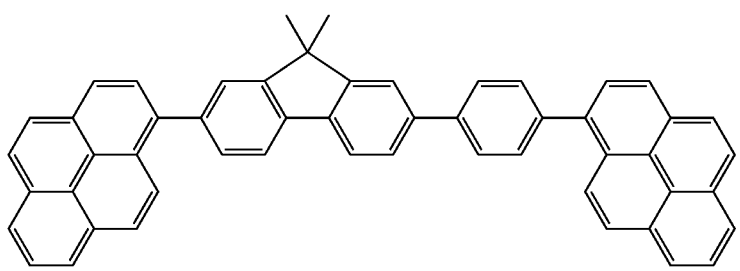
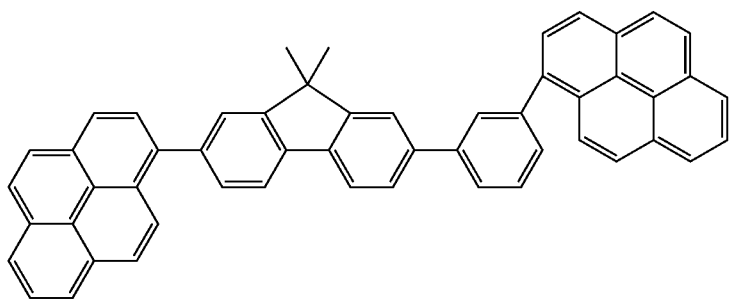

-continued
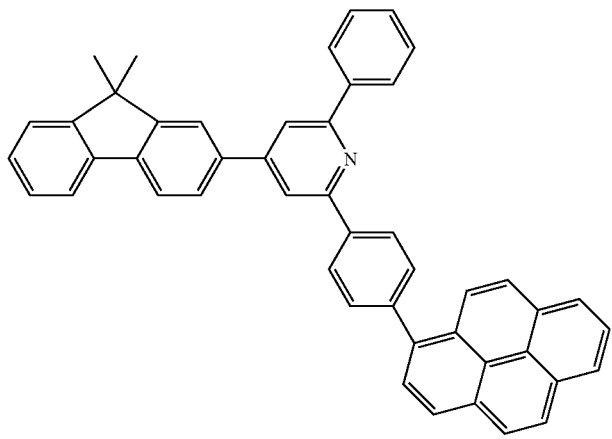
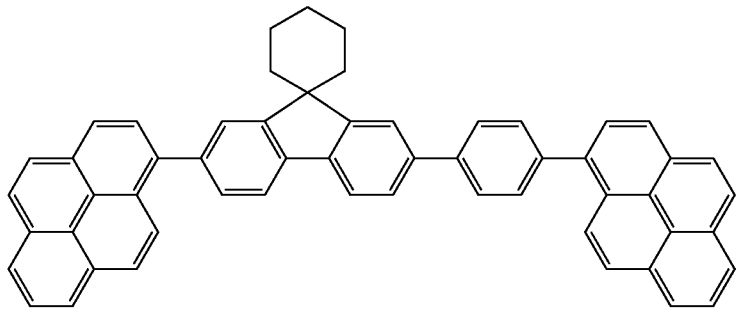
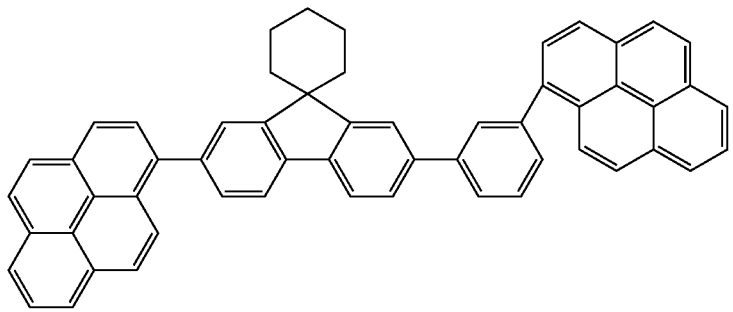
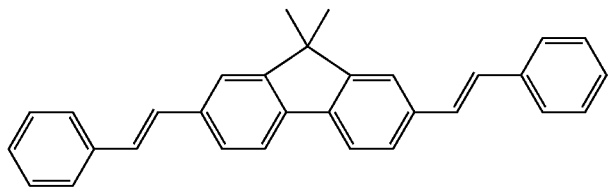
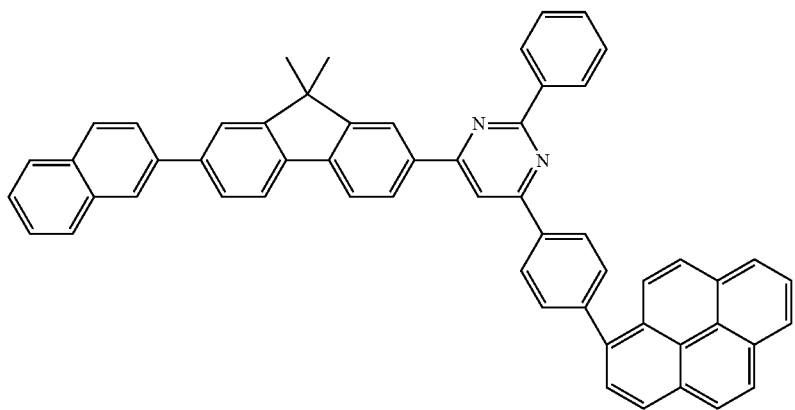

-continued
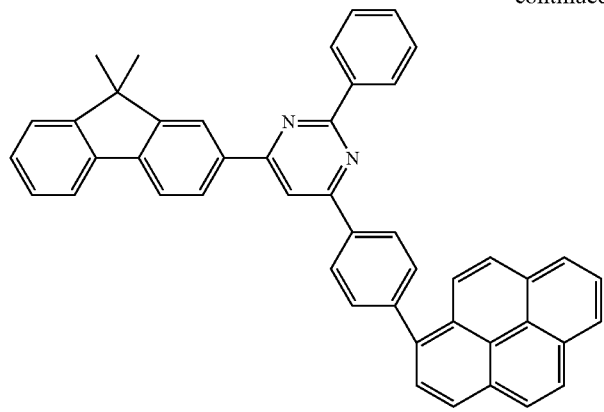
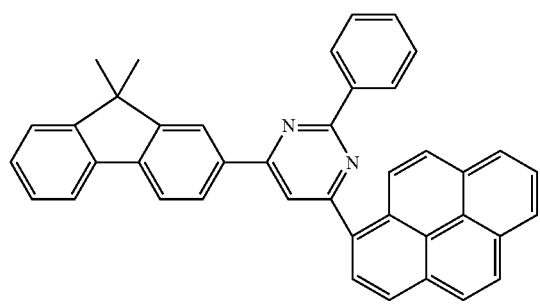
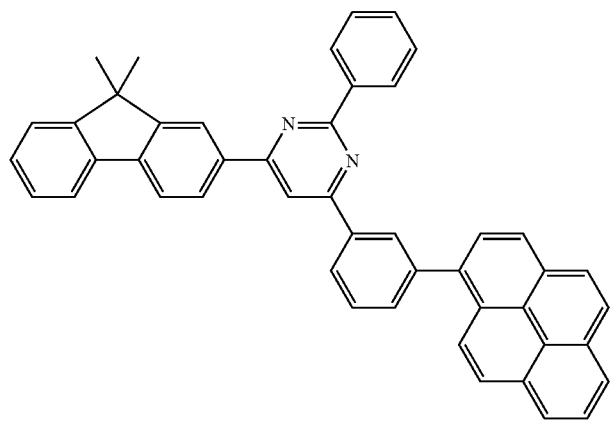
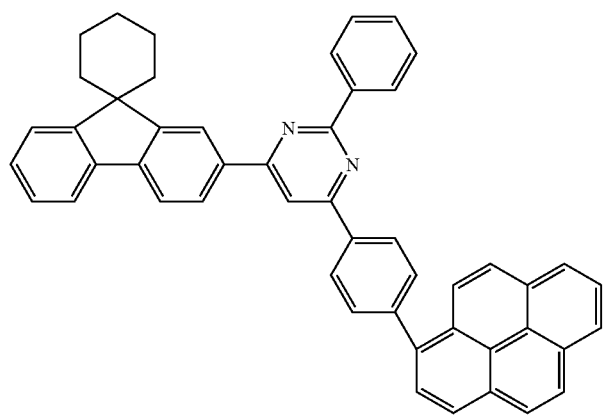

-continued
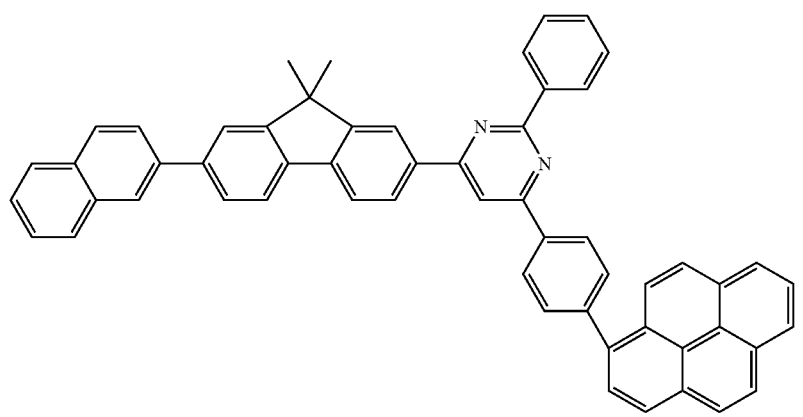
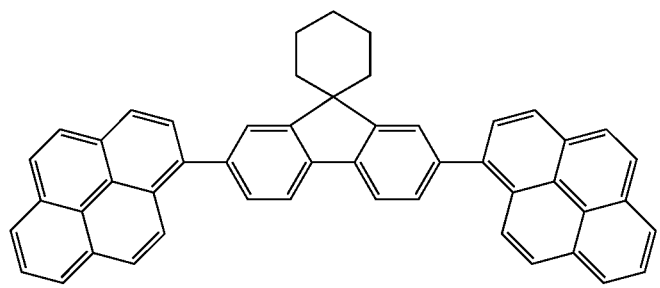
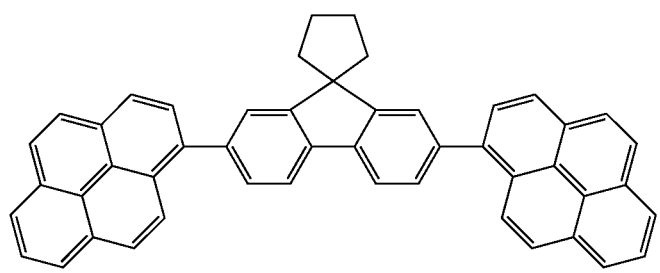
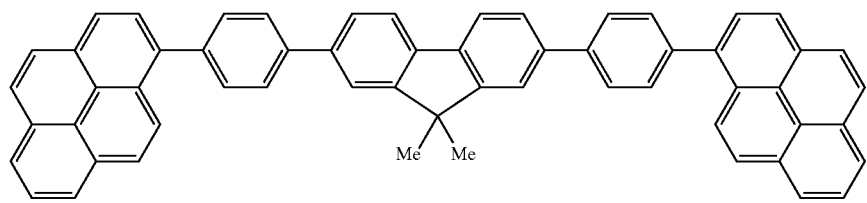
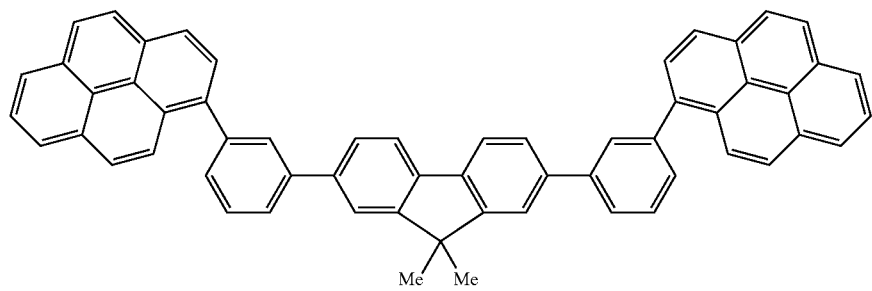
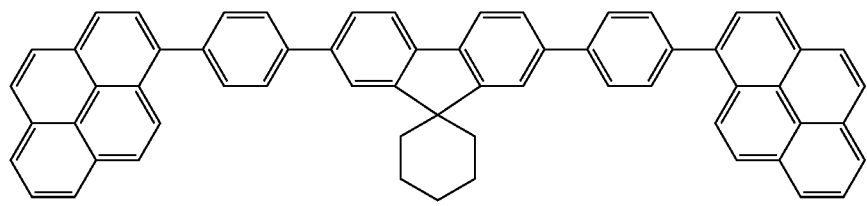

-continued
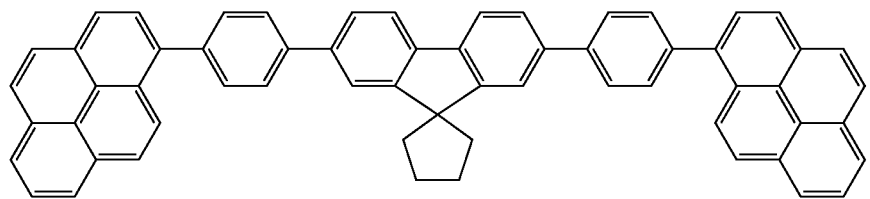
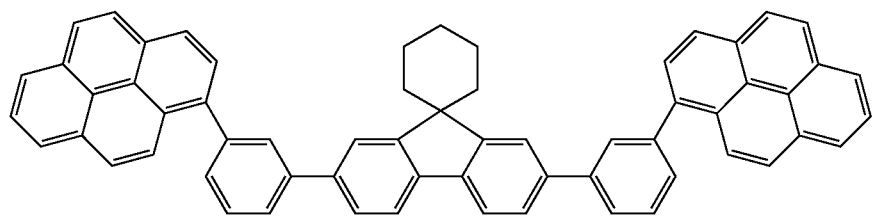
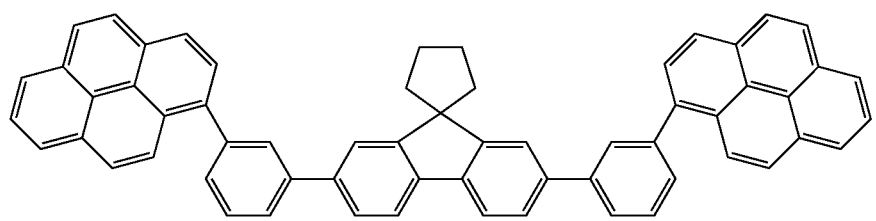
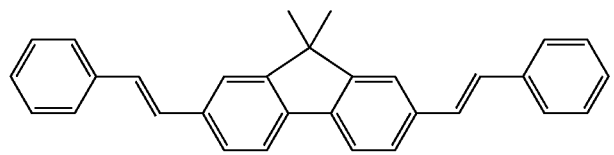
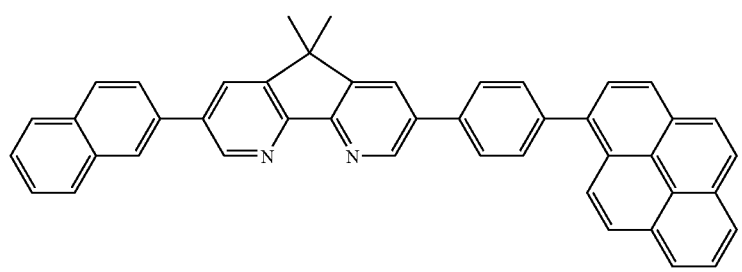
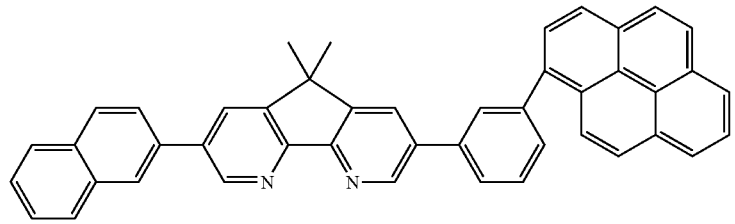
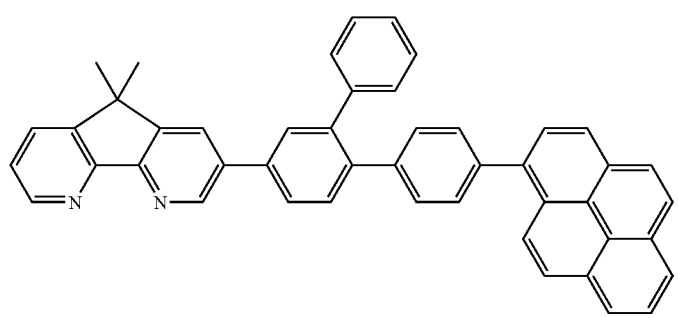

-continued
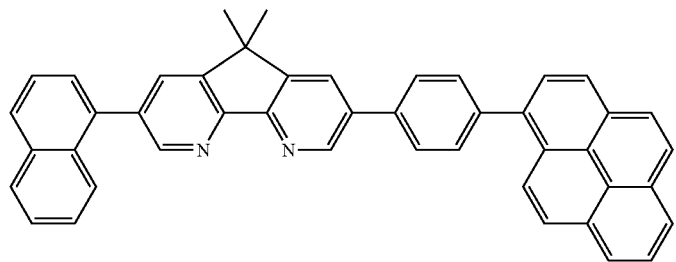
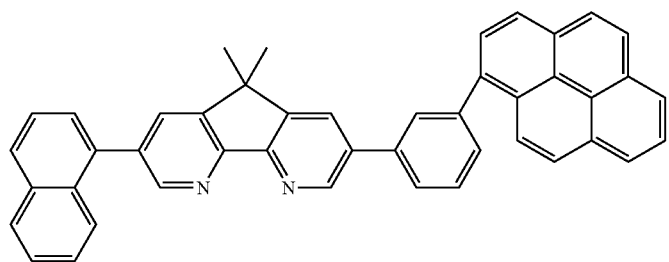
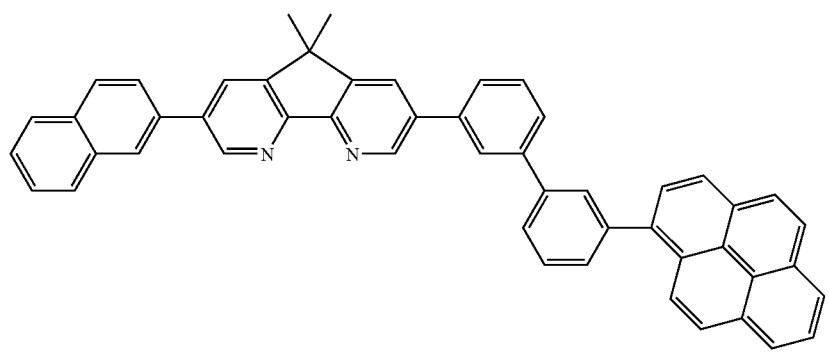
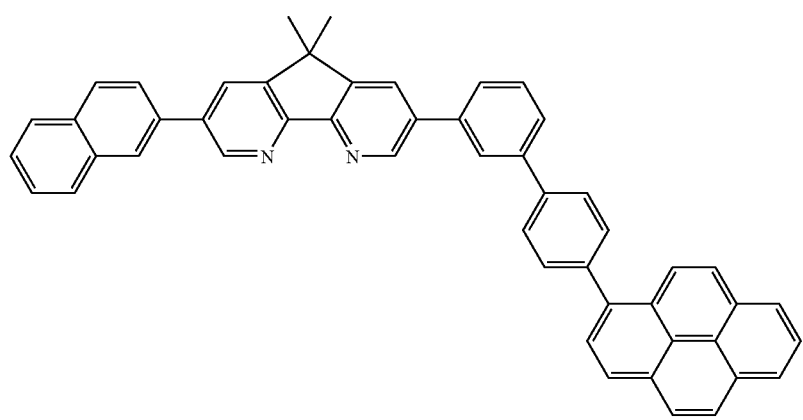

-continued
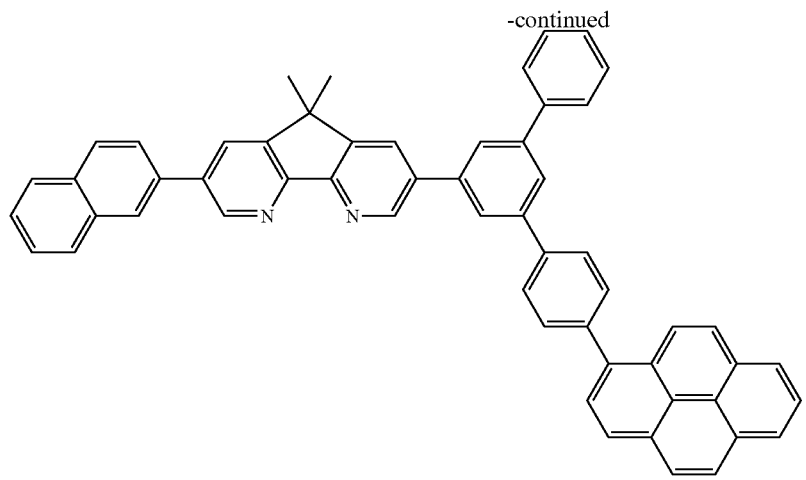
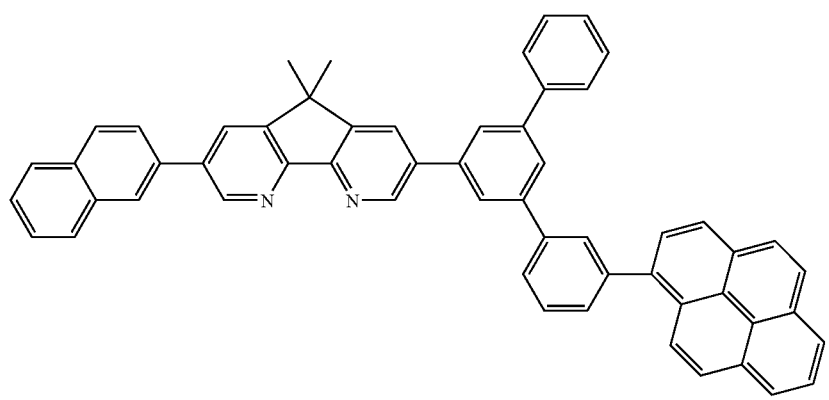
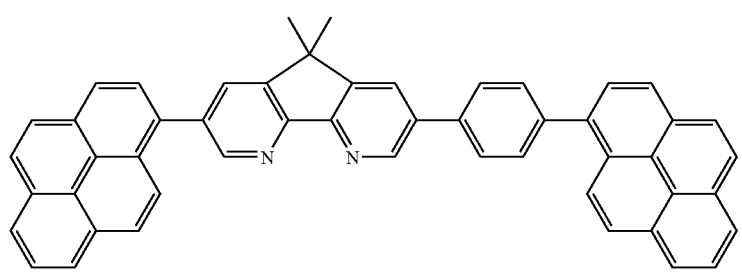
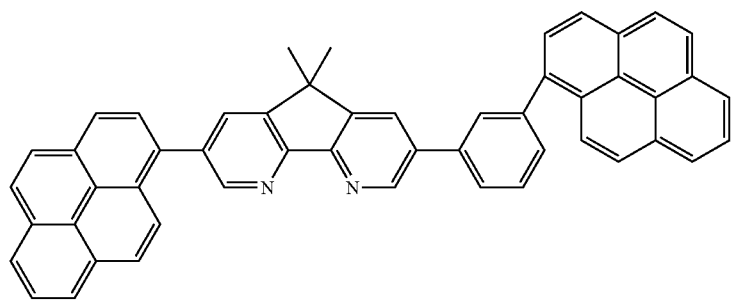

-continued
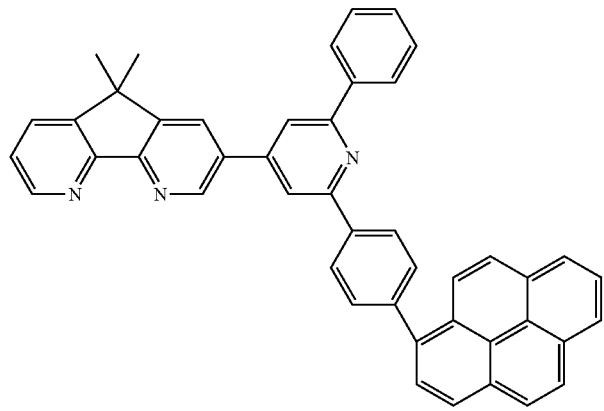
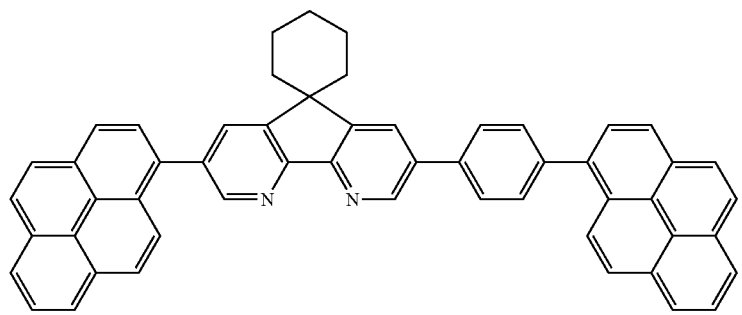
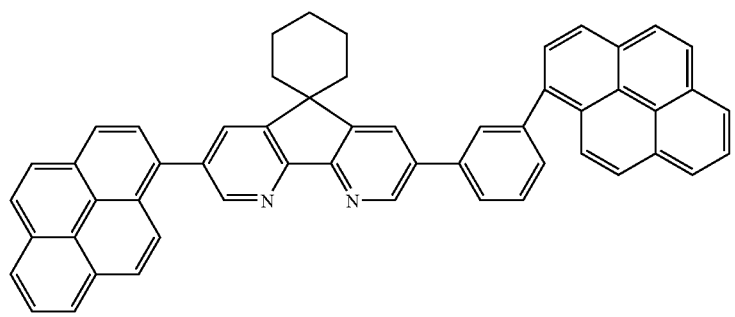
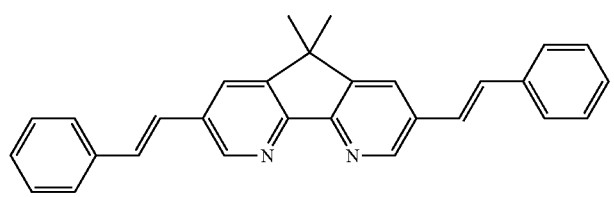
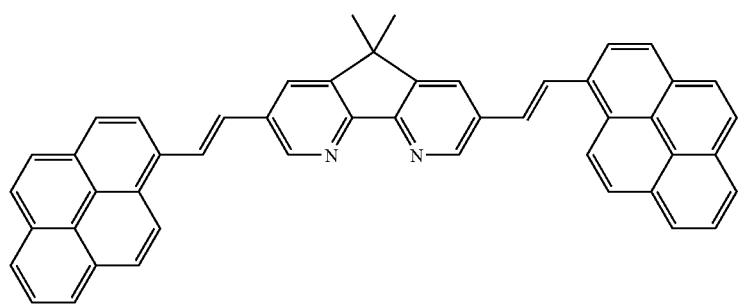

-continued
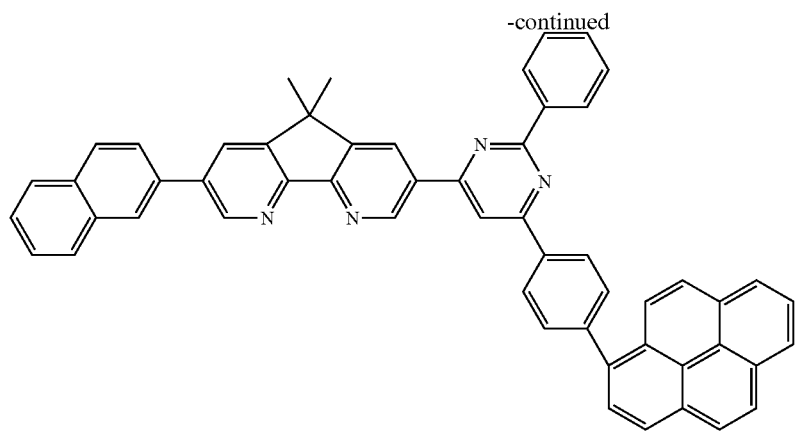
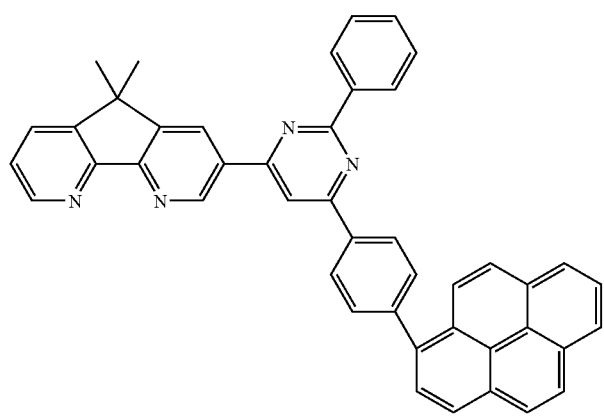
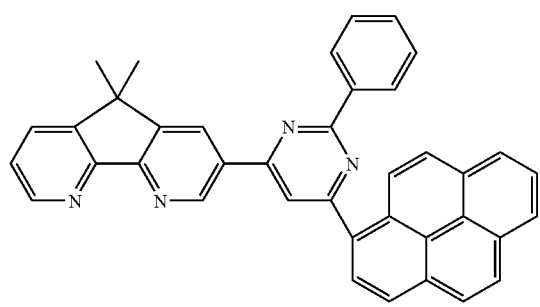
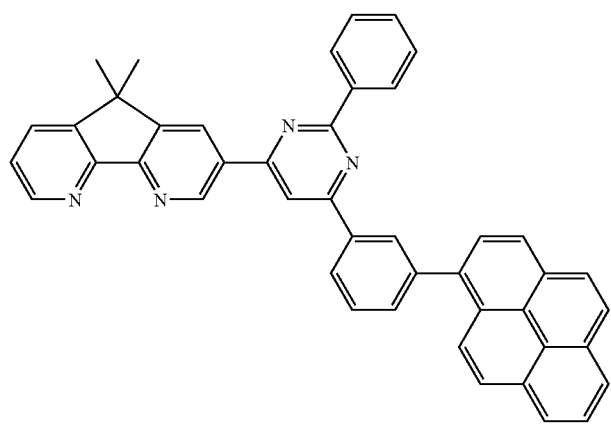

-continued
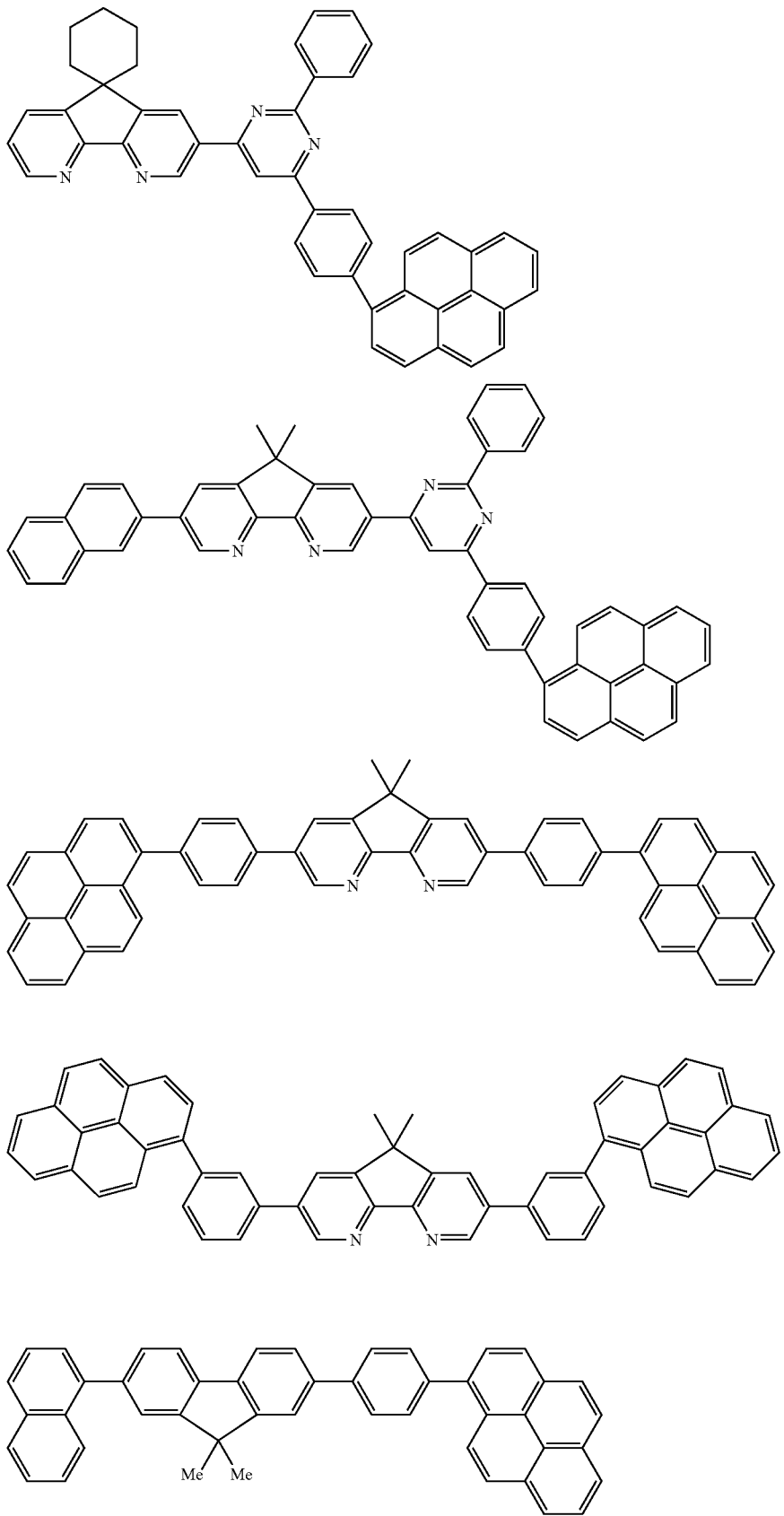

-continued
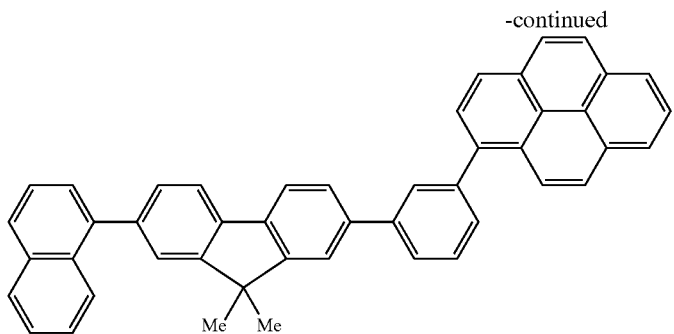
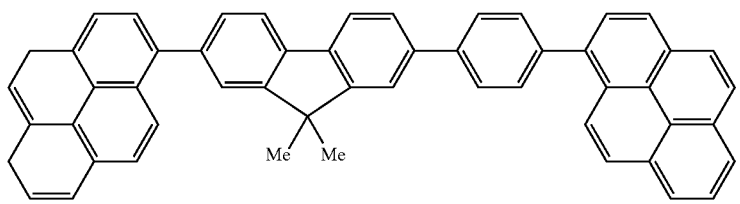
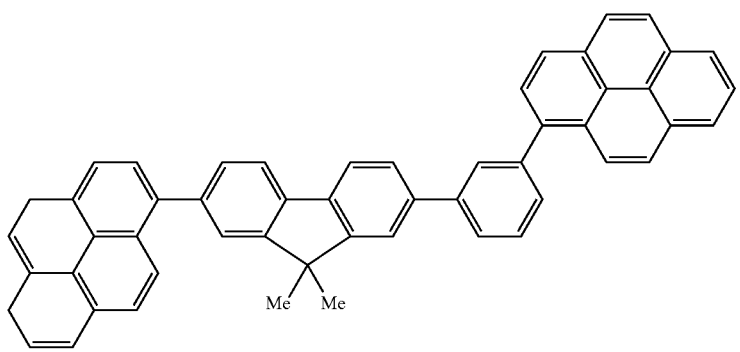
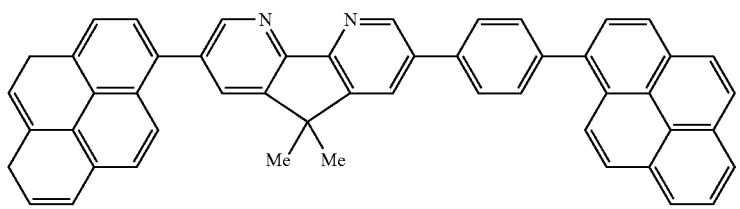
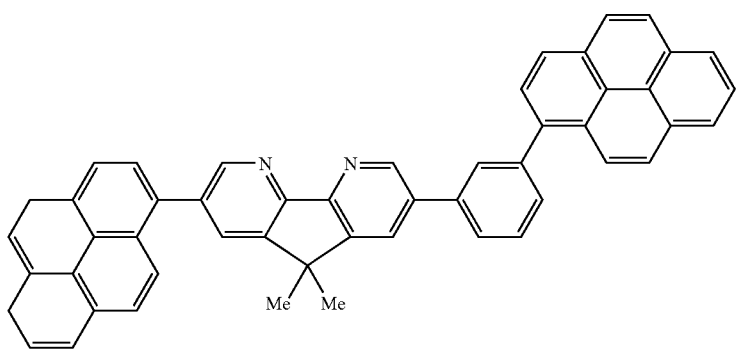

The fluorene-based derivative of the present invention represented by Formula (1) is preferably a material for an organic EL device, and it is preferably a host material for an organic EL device.

In the organic EL device of the present invention in which an organic thin film layer comprising a single layer or plural layers including at least a light emitting layer is sandwiched between a cathode and an anode, at least one layer of the above organic thin film layers comprises the fluorene-based derivative of the present invention represented by Formula (1) in the form of a single component or a mixed component.

In the organic EL device of the present invention, the light emitting layer described above preferably contains 10 to 100% by weight of the fluorene-based derivative of the present invention and more preferably contains 50 to 99% by weight thereof as a host material.

Further, in the organic EL device of the present invention, the light emitting layer described above may contain a fluorescent or phosphorescent dopant in addition to the fluorene-based derivative represented by Formula (1).

The fluorescent dopant described above is preferably a compound which is selected according to a required luminescent color from amine-based compounds, chelate complexes such as a tris(8-quinolinolate)aluminum complex, coumarine derivatives, tetraphenylbutadiene derivatives, bisstyrylarylene derivatives and oxadiazole derivatives.

Among them, the amine-based compounds are preferably arylamine compounds and/or styrylamine compounds.

The styrylamine compounds described above are preferably compounds represented by the following Formula (A):

(A)

wherein $Ar^3$ is a group selected from a phenyl group, a biphenyl group, a terphenyl group, a stilbene group and a distyrylaryl group; $Ar^4$ and $Ar^5$ each are a hydrogen atom or an aromatic group having 6 to 20 carbon atoms, and $Ar^3$ to $Ar^5$ may be substituted; p is an integer of 1 to 4; and more preferably, at least one of $Ar^4$ and $Ar^5$ is substituted with a styryl group.

In this regard, the aromatic group having 6 to 20 carbon atoms includes phenyl, naphthyl, anthranyl, phenanthryl and terphenyl.

The arylamine compounds described above are preferably compounds represented by the following Formula (B):

(B)

wherein $Ar^6$ to $Ar^8$ are a substituted or unsubstituted aryl group having 5 to 40 nuclear carbon atoms; and q is an integer of 1 to 4.

In this regard, the aryl group having 5 to 40 nuclear carbon atoms includes, for example, phenyl, naphthyl, chrysenyl, naphthacenyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acenaphthofluoranthenyl and stilbene. Preferred substituents for the above aryl group include an alkyl group having 1 to 6 carbon atoms (ethyl, methyl, i-propyl, n-propyl, s-butyl, t-butyl, pentyl, hexyl, cyclopentyl and cyclohexyl), an alkoxy group having 1 to 6 carbon atoms (ethoxy, methoxy, i-propoxy, n-propoxy, s-butoxy, t-butoxy, pentoxy, hexyloxy, cyclopentoxy and cyclohexyloxy), an aryl group having 5 to 40 nuclear carbon atoms, an amino group substituted with an aryl group having 5 to 40 nuclear carbon atoms, an ester group having an aryl group having 5 to 40 nuclear carbon atoms, an ester group having an alkyl group having 1 to 6 carbon atoms, a cyano group, a nitro group and a halogen atom.

The phosphorescent dopant described above is preferably a metal complex compound containing at least one metal selected from Ir, Ru, Pd, Pt, Os and Re, and the ligand preferably has at least one skeleton selected from a phenylpyridine skeleton, a bipyridyl skeleton and a phenanthroline skeleton. The specific examples of the above metal complexes include tris(2-phenylpyridine)iridium, tris (2-phenylpyridine)ruthenium, tris (2-phenylpyridine)-palladium, tris(2-phenylpyridine)platinum, tris(2-phenylpyridine)osmium, tris(2-phenylpyridine)rhenium, octaethylplatinum porphyrin, octaphenylplatinum porphyrin, octaethylpalladium porphyrin and octaphenylpalladium porphyrin. However, they shall not be restricted thereto, and the suitable complexes are selected in terms of the required luminescent color, the device performances and relation with the host compound.

The device structure of the organic EL device of the present invention shall be explained below.

The organic EL device of the present invention is a device in which an organic compound layer comprising a single layer or a multilayer is formed between an anode and a cathode. In the case of the single layer type, a light emitting layer is provided between an anode and a cathode. The light emitting layer contains a light emitting material, and in addition thereto, it may contain a hole injecting material or an electron injecting material in order to transport a hole injected from the anode or an electron injected from the cathode to the light emitting material. However, the light emitting material preferably has a very high fluorescent quantum efficiency, a high hole transporting ability and a high electron transporting ability in combination, and an even thin film is preferably formed. The organic EL element of the multilayer type is laminated in a multilayer structure of (anode/hole injecting layer/light emitting layer/cathode), (anode/light emitting layer/electron injecting layer/cathode) and (anode/hole injecting layer/light emitting layer/electron injecting layer/cathode).

Further, publicly known light emitting materials, doping materials, hole injection materials and electron injection materials in addition to the compound of the present invention represented by Formula (1) can be added and used, if necessary, in the light emitting layer as described above. All of heavy metal complexes represented by phosphorescent iridium in addition to conventional fluorescent materials can be used as the doping material. The organic EL element can be prevented from a reduction in a luminance and a life due to quenching by assuming a multilayer structure. The light emitting material, other doping materials, a hole injecting material and an electron injecting material can be used, if necessary, in combination. The other doping materials make it possible to obtain a rise in the light emitting luminance and the luminous efficiency and luminescence of a red color and a white color. The hole injecting layer, the light emitting layer and the electron injecting layer each may be formed in a layer structure of two or more layers. In such case, in the case of the hole injecting layer, a layer into which a hole is injected from an electrode is called a hole injecting layer, and a layer which receives a hole from the hole injecting layer and transports it to a light emitting layer is called a hole transporting layer. Similarly, in the case of the electron injecting layer, a layer into which an electron is injected from an electrode is called an electron injecting layer, and a layer which receives an electron from the electron injecting layer and transports it to the light emitting layer is called an electron transporting layer. The above respective layers are selected and used according to respective factors such as an energy level of the materials, a heat resistance and an adhesion to the organic thin film layer or the metal electrode.

In the organic EL device of the present invention, the light emitting material or the host material which can be used in the organic thin film layer together with the compound of the present invention represented by Formula (1) includes anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, stilbene-based derivatives and fluorescent coloring matters. However, it shall not be restricted to them.

The hole injecting materials which can be used in the organic EL device of the present invention are preferably compounds which are provided with ability to transport holes and have an effect of injecting holes from an anode and an excellent effect of injecting holes into a light emitting layer or a light emitting material and which prevent excitons formed in the light emitting layer from transferring to an electron injecting layer or an electron injecting material and are excellent in a thin film-forming ability. To be specific, they include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine and derivatives thereof and high molecular materials such as polyvinylcarbazole, polysilane and conductive polymers, but they shall not be restricted thereto.

Among the hole injecting materials which can be used in the organic EL device of the present invention, more effective hole injection materials are aromatic tertiary amine derivatives and phthalocyanine derivatives.

The specific examples of the aromatic tertiary amine derivatives described above are triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-tolylaminophenyl)-4-phenyl-cyclohexane and oligomers or polymers having aromatic tertiary amine skeletons thereof, but they shall not be restricted thereto.

The specific examples of the phthalocyanine (Pc) derivatives described above include phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VoPc, TiOPc, MoOPc and GaPc—O—GaPc and naphthalocyanine derivatives, but they shall not be restricted thereto.

The electron injecting materials which can be used in the organic EL device of the present invention are preferably compounds which are provided with ability to transport electrons and have an effect of injecting electrons from a cathode and an excellent effect of injecting electrons into a light emitting layer or a light emitting material and which prevent excitons formed in the light emitting layer from transferring to a hole injecting layer and are excellent in a thin film-forming ability. To be specific, they include fluorenone, anthraquinodimethane, diphenoquinone, thiopyran dioxide, oxazole, oxadiazole, triazole, imidazole, perylenetetracarboxylic acid, fluorenilidenemethane, anthraquinodimethane, anthrone and derivatives thereof, but they shall not be restricted thereto. Further, the charge injecting property can be raised by adding an electron receiving substance to the hole injecting material and adding an electron donating substance to the electron injecting material.

In the organic EL device of the present invention, more effective electron injecting materials are metal complex compounds or nitrogen-containing five-membered ring derivatives.

The specific examples of the metal complex compounds described above include 8-hydroxyquinolinatelithium, bis(8-hydroxyquinolinate)zinc, bis(8-hydroxyquinolinate)copper, bis(8-hydroxyquinolinate)manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-quinolinate)chlorogallium, bis(2-methyl-8-quinolinate) (o-crezolate)gallium, bis(2-methyl-8-quinolinate) (o-naphtholate)aluminum, bis(2-methyl-8-quinolinate)(1-naphtholate)aluminum and bis(2-methyl-8-quinolinate) (2-naphtholate)gallium, but they shall not be restricted thereto.

The nitrogen-containing five-membered ring derivatives described above are preferably oxazole, thiazole, oxadiazole, thiadiazole and triazole derivatives. To be specific, they include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene, but they shall not be restricted thereto.

In the organic EL device of the present invention, at least one of light emitting materials, doping materials, hole injection materials and electron injection materials in addition to the compound represented by Formula (1) may be contained in the same layer in the organic thin film layer. Further, in order to improve a stability of the organic EL device obtained according to the present invention against the temperature, the humidity and the environment, a protective layer can be provided on the surface of the device, and the whole part of the device can be protected by a silicon oil, a resin and the like.

A conductive material used for an anode in the organic EL device of the present invention is suitably a material having a work function of greater than 4 eV, and usable are carbon, aluminum, vanadium, iron, cobalt, nickel, tungsten, silver, gold, platinum, palladium and alloys thereof, metal oxides such as tin oxide and indium oxide which are used for an ITO substrate and an NESA substrate and organic conductive resins such as polythiophene and polypyrrole. The conductive material used for the cathode is suitably a material having a work function of smaller than 4 eV, and used therefor are magnesium, calcium, tin, lead, titanium, yttrium, lithium, ruthenium, manganese, aluminum and alloys thereof, but it shall not be restricted to them. The representative examples of the alloys include magnesium/silver, magnesium/indium and lithium/aluminum, but it shall not be restricted to them. A proportion of the alloys is controlled according to a temperature of the vapor deposition source, the atmosphere and the vacuum degree, and the suitable proportion is selected. The anode and the cathode may be formed, if necessary, in a layer structure of two or more layers.

In the organic EL device, it is preferred that at least one surface thereof is sufficiently transparent in a luminescent wavelength area of the device in order to efficiently emit light. Further, the substrate is preferably transparent as well. A transparent electrode is set up by a method such as vapor deposition and sputtering using the conductive materials described above so that prescribed transparency is secured. The electrode on the luminescent face is preferably controlled to a light transmittance of 10% or more. The substrate shall not be restricted as long as it has mechanical and thermal strengths and is transparent, and it includes a glass substrate and a transparent resin film. The transparent resin film includes polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide and polypropylene.

The respective layers in the organic EL device of the present invention can be formed by applying any of a dry film forming method such as vacuum vapor deposition, sputtering, plasma and ion plating and a wet film forming method such as spin coating, dipping and flow coating. The film thickness shall not specifically be restricted, and it has to be set to a suited film thickness. When the film thickness is too large, large voltage has to be applied in order to obtain a constant light output, so that the efficiency is deteriorated. When the film thickness is too small, pinholes are formed, and the satisfactory light emitting luminance is not obtained when applying an electric field. Usually, the film thickness falls in a range of suitably 5 nm to 10 μm, more preferably 10 nm to 0.2 μm. In the case of the wet film forming method, materials for forming the respective layers are dissolved or dispersed in a suitable solvent such as ethanol, chloroform, tetrahydrofuran and dioxane to form thin films, and the solvent may be any one. Suitable resins and additives may be used in any organic thin film in order to improve the film forming property and prevent pinholes from being formed on the film. The resins which can be used include insulating resins such as polystyrene, polycarbonate, polyallylate, polyester, polyamide, polyurethane, polysulfone, polymethyl methacrylate, polymethyl acrylate and cellulose and copolymers thereof, photoconductive resins such as poly-N-vinylcarbazole and polysilane and conductive resins such as polythiophene and polypyrrole. The additives include antioxidants, UV absorbers and plasticizers.

As described above, the organic EL device having a high luminous efficiency can be obtained by using the fluorene-based derivative represented by Formula (1) of the present invention for the organic thin film layer of the organic EL device.

The organic EL device of the present invention can be used, for example, as a planar illuminant for flat panel displays of wall-hanging type television sets, a backlight for copying machines, printers and liquid crystal displays, a light source for measuring instruments, a display board and a marker lamp.

EXAMPLES

Next, the present invention shall be explained in further details with reference to examples. The performances of the organic EL devices obtained in the respective examples were evaluated in the following manners.

Example 1

Synthesis of Compound (H-1) and Fabrication of Organic EL Device (1) Synthesis of Compound (H-1)

A Compound (H-1) which was the fluorene-based derivative represented by Formula (1) described above was synthesized in the following manner.

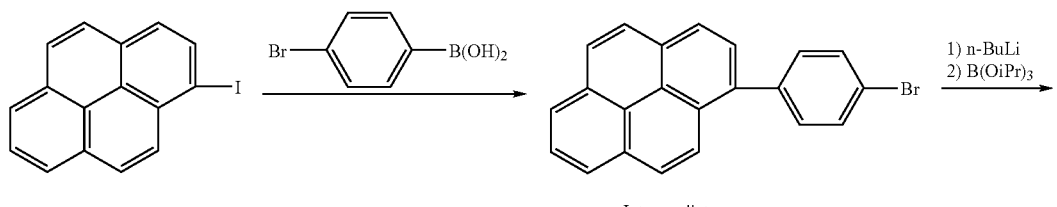

Intermediate a

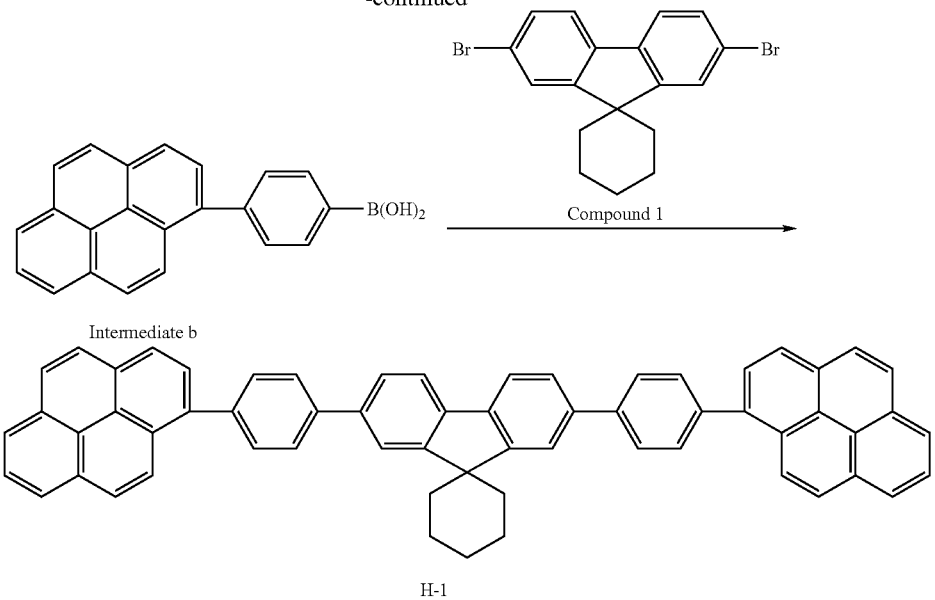

Intermediate b

H-1

A 300 ml three neck flask was charged with 7.22 g (22 mmol) of 1-iodo-pyrene, 4.02 g (20 mmol) of 4-bromophenylboronic acid and 0.46 g (0.40 mmol, 2% Pd) of tetrakis(tiphenylphosphine)palladium (0), and the inside of the vessel was replaced with argon. Further, 40 ml of 1,2-dimethoxyethane and 30 ml (3 eq) of a 2M-sodium carbonate aqueous solution were added thereto, and the mixture was heated and refluxed on an oil bath of 90° C. for 9 hours. The reaction solution was cooled down to room temperature, and methylene chloride and water were added to separate the solution into two layers. Then, the organic layer was washed with water and dried on anhydrous sodium sulfate. The organic solvent was distilled off, and then the residue was refined by silica gel column chromatography to obtain 5.85 g (yield 82%) of an Intermediate a.

The Intermediate a in an amount of 5.72 g (16 mmol) was dissolved in 100 ml toluene, and 12 ml (19.2 mmol) of a normal butyllithium hexane solution (1.6M) was added thereto at −70° C. under argon atmosphere, followed by stirring at −70° C. to 0° C. for one hour.

Next, the reaction solution was cooled down to −70° C., and 11 ml (48 mmol) of triisopropyl borate was dropwise added thereto, followed by stirring at −70° C. for one hour. Then, the solution was heated up to room temperature and stirred for 6 hours. Further, 100 ml of 5% hydrochloric acid was dropwise added to the reaction solution, and then the solution was stirred at room temperature for 45 minutes. The reaction solution was separated into two layers, and then the organic layer was washed with a saturated sodium chloride aqueous solution and dried on anhydrous sodium sulfate. The organic solvent was distilled off under vacuum to a level of one fifth, and then deposited crystal was filtered and washed in order with a toluene-normal hexane mixed solvent and normal hexane to obtain 4.52 g (yield 88%) of an Intermediate b.

A 100 ml three neck flask was charged with 1.96 g (5 mmol) of the compound 1, 3.54 g (11 mmol) of the Intermediate b and 0.254 g (0.22 mmol, 2 mol %) of tetrakis(tiphenylphosphine)palladium (0), and the inside of the vessel was replaced with argon. Further, 20 ml of 1,2-dimethoxyethane and 16.5 ml (3 eq) of a 2M-sodium carbonate aqueous solution were added thereto, and the mixture was heated and refluxed on an oil bath of 90° C. for 8 hours. After one night, the deposit was filtered and washed with 1,2-dimethoxyethane, ion-exchanged water and methanol. The resulting grey solid matter was further refined by refluxing in ethyl acetate for one hour and then filtered. The synthesized amount was 3.37 g (yield: 84%). The Compound (H-1) thus obtained was measured for FD-MS (field desorption mass spectrum), and the result thereof is shown below.

FD-MS: calculated for $C_{63}H_{46}$=803, found m/z=803 (M$^+$, 100)

(2) Fabrication of Organic EL Device

A glass substrate (manufactured by GEOMATIC Company) of 25 mm×75 mm×1.1 mm thickness equipped with an ITO transparent electrode was subjected to ultrasonic wave washing in isopropyl alcohol for 5 minutes and then to UV ozone washing for 30 minutes. The glass substrate equipped with an ITO transparent electrode line after washing was mounted on a substrate holder of a vacuum depositing apparatus, and a film of N,N'-bis(N,N'-diphenyl-4-aminophenyl)-N,N'-diphenyl-4,4'-diamino-1,1'-biphenyl (hereinafter referred to as "TPD232 film") having a film thickness of 60 nm was formed on a surface at a side on which the transparent electrode line was formed so that the transparent electrode described above was covered. This TPD232 film functions as a hole injecting layer. A film of N,N,N',N'-tetra(4-biphenyl)-diaminobiphenylene (hereinafter referred to as "TBDB film") having a film thickness of 20 nm was formed on the above TPD232 film. This TBDB film functions as a hole transporting layer. Further, the Compound (H-1) was deposited as a host material to form a film having a film thickness of 40 nm. The following amine Compound D1 having a styryl group was deposited as a light emitting molecule at the same time as above at a weight ratio of D1:(H-1)=3:40. This film functions as a light emitting layer. A film of the following compound Alq having a film thickness of 10 nm was formed on the above film. This film functions as an electron injecting layer. Thereafter, Li (Li source: manufactured by SAES GETTERS Company) which was a reducing dopant and Alq were subjected to binary deposition to form an Alq:Li film (film thickness: 10 nm) as an electron injecting layer (cathode). Metal Al was deposited on the above Alq:Li film to form a metal cathode, whereby an organic EL device was fabricated.

The device thus obtained was measured about a current efficiency and a color of light emission, and the results thereof are shown in Table 1.

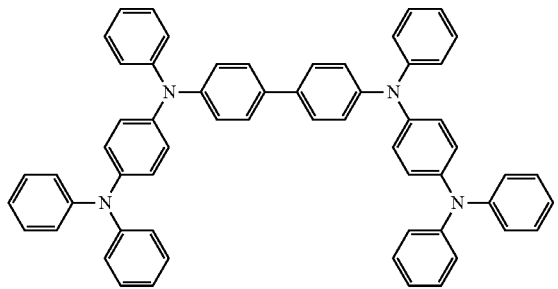

TPD232

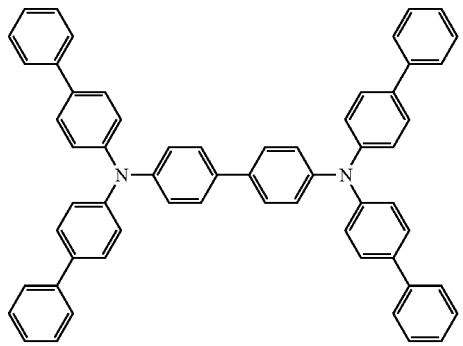

TBDB

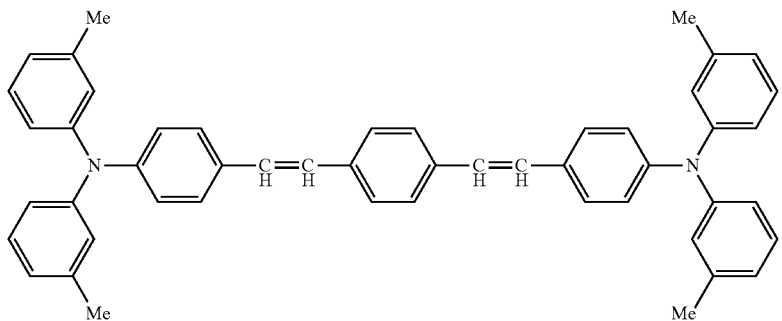

D1

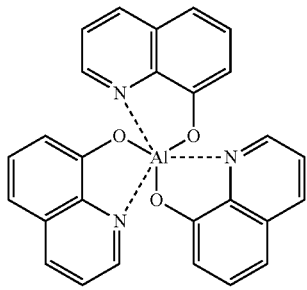

Alq

Examples 2 to 8

Fabrication of Organic EL Devices

Organic EL devices were fabricated in the same manner as term (2) of Example 1, except that the following Compounds (H-2) to (H-4) which are the fluorene-based derivatives represented by Formula (1) described above were employed instead of the Compound (H-1).

The device thus obtained was measured about a current efficiency and a color of light emission, and the results thereof are shown in Table 1.

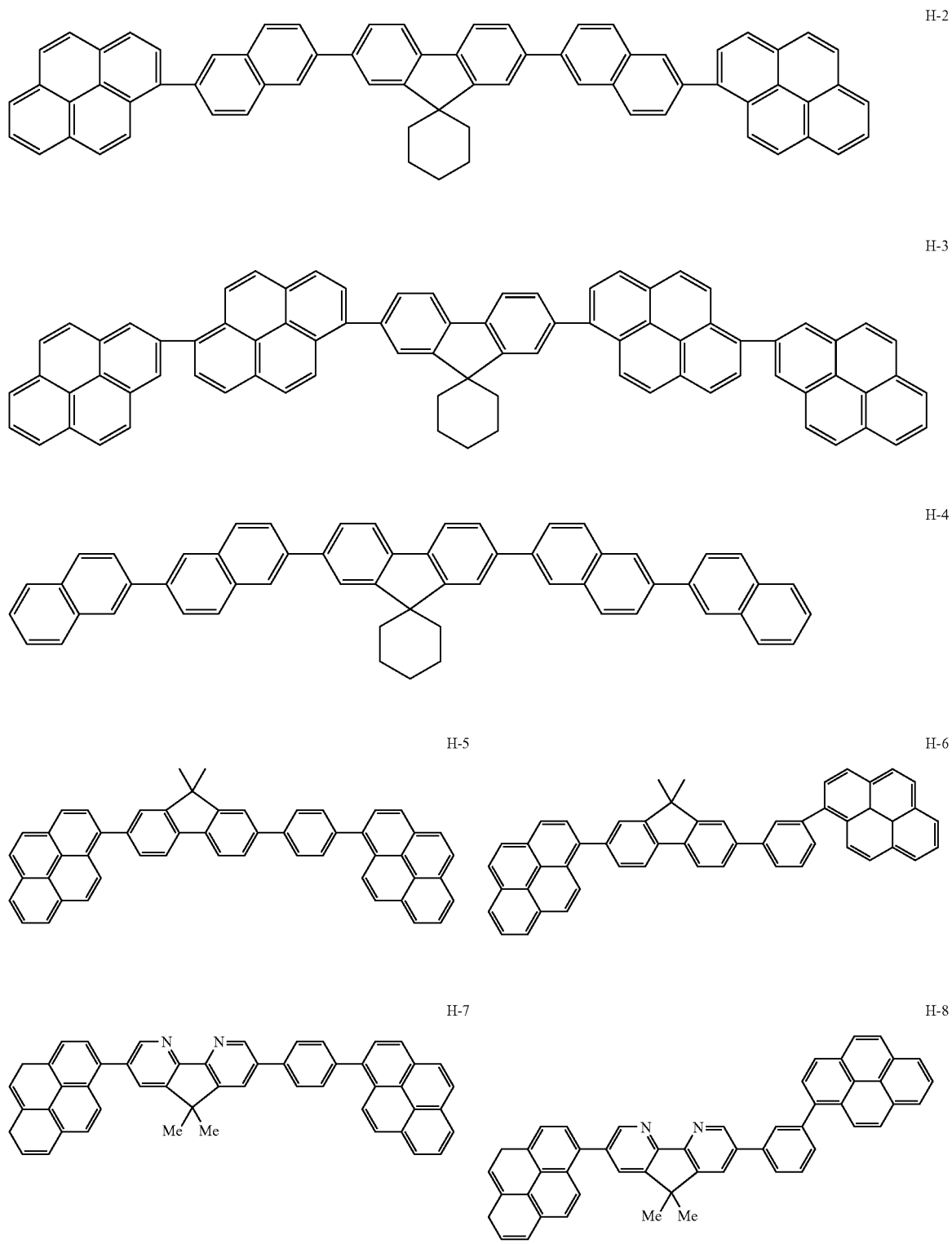

Comparative Examples 1 to 2

Organic EL devices were produced in the same manner as term (2) of Example 1, except that the following compounds (Comparative Compound 1 and Comparative Compound 2) which are fluorene-based derivatives not satisfying Formula (1) described above were employed instead of the Compound (H-1). In the Comparative Compounds 1 and 2, Me is methyl.

The device thus obtained was measured about a current efficiency and a color of light emission, and the results thereof are shown in Table 1.

TABLE 1

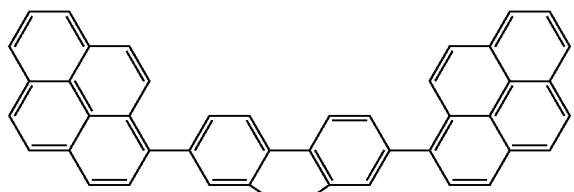

Comparative Compound 1

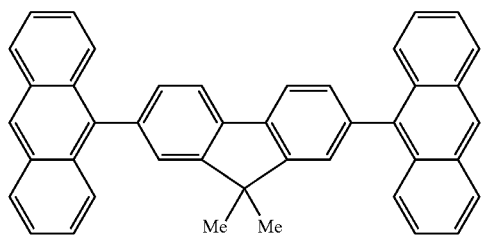

Comparative Compound 2

| | Host material in light emitting layer | Current efficiency (cd/A) | Color of light emission |
|---|---|---|---|
| Example 1 | H-1 | 11.2 | Blue |
| Example 2 | H-2 | 11.1 | Blue |
| Example 3 | H-3 | 11.4 | Blue |
| Example 4 | H-4 | 11.5 | Blue |
| Example 5 | H-5 | 12.1 | Blue |
| Example 6 | H-6 | 11.9 | Blue |
| Example 7 | H-7 | 11.8 | Blue |
| Example 8 | H-8 | 11.3 | Blue |
| Comparative Example 1 | Comparative compound 1 | 9.5 | Blue |
| Comparative Example 2 | Comparative compound 2 | 9.1 | Blue |

Example 9

Synthesis of Compound (H-5) and Fabrication of Organic EL Device (1) Synthesis of Compound (H-5)

A Compound (H-5) which is the fluorene-based derivative represented by Formula (1) described above was synthesized in the following manner.

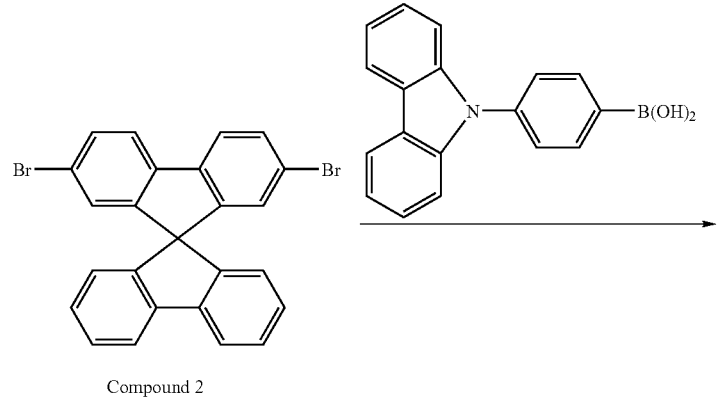

Compound 2

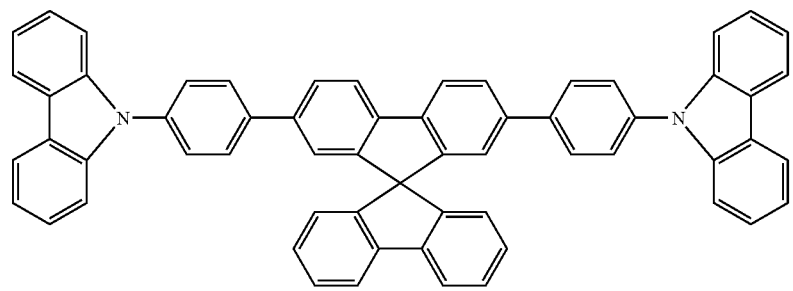

H-5

A 100 ml three neck flask was charged with 2.37 g (5 mmol) of the compound 2, 3.16 g (11 mmol) of 4-(N-carbazolyl)phenylboronic acid and 0.254 g (0.22 mmol, 2 mol %) of tetrakis(tiphenylphosphine)-palladium (0), and the inside of the flask was replaced with argon. Further, 20 ml of 1,2-dimethoxyethane and 16.5 ml (3 eq) of a 2M-sodium carbonate aqueous solution were added thereto, and the mixture was heated and refluxed on an oil bath of 90° C. for 8 hours. After one night, the deposit was filtered and washed with 1,2-dimethoxyethane, ion-exchanged water and methanol. The resulting grey solid matter was further refined by refluxing in ethyl acetate for one hour and then filtered. The synthesized amount was 3.16 g (yield: 79%). The Compound (H-5) thus obtained was measured for FD-MS, and the result thereof is shown below.

FD-MS: calculated for $C_{61}H_{46}N_2$=803, found m/z=803 ($M^+$, 100)

(2) Fabrication of Organic EL Device

A glass substrate of 25 mm×75 mm×0.7 mm thickness equipped with an ITO transparent electrode was subjected to ultrasonic wave washing in isopropyl alcohol for 5 minutes and then to UV ozone washes for 30 minutes. The glass substrate equipped with the ITO transparent electrode after washing was mounted on a substrate holder of a vacuum depositing apparatus, and a film of copper phthalocyanine shown below (hereinafter referred to as "CuPc film") having a film thickness of 10 nm was formed on a surface at a side on which the transparent electrode was formed so that the transparent electrode described above was covered. This CuPc film functions as a hole injecting layer. A film of 4,4'-bis[N-(1-naphthyl)-N-phenylamino]biphenyl (hereinafter referred to as "α-NPD film") having a film thickness of 30 nm was formed on the above CuPc film. This α-NPD film functions as a hole transporting layer. Further, the Compound (H-1) was deposited as a host material on the above α-NPD film to form a light emitting layer having a film thickness of 30 nm. Tris (2-phenylpyridine)iridium (hereinafter abbreviated as "Ir (ppy)3") was added thereto as a phosphorescent Ir metal complex dopant. A concentration of Ir(ppy)3 in the light emitting layer was set to 5% by weight. This film functions as a light emitting layer. A film of (1,1'-bisphenyl)-4-oleate)bis (2-methyl-8-quinolinolate)aluminum shown below (hereinafter referred to as "BAlq film") having a film thickness of 10 nm was formed on the above film. This BAlq film functions as a hole barriering layer. Further, an Alq film having a film thickness of 40 nm was formed on the above film. This Alq film functions as an electron injecting layer. Thereafter, LiF which is alkaline metal halide was deposited in a thickness of 0.2 nm, and then aluminum was deposited in a thickness of 150 nm. This Al/LiF functions as a cathode. Thus, an organic EL device was produced.

The device thus obtained was subjected to a test passing electric current and as a result, blue light emission of 8500 cd/m² at a voltage of 8 V was obtained.

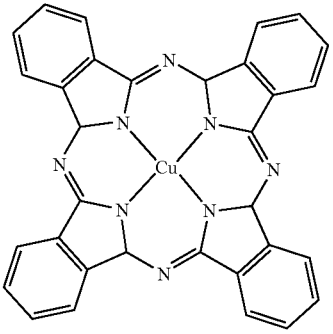

CuPc

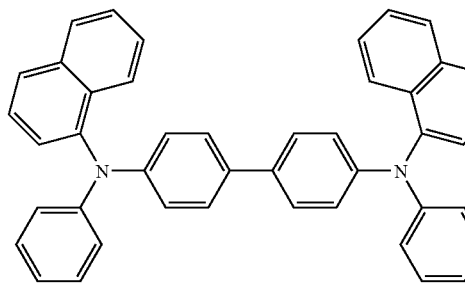

α-NPD

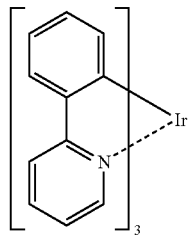

Ir(ppy)3

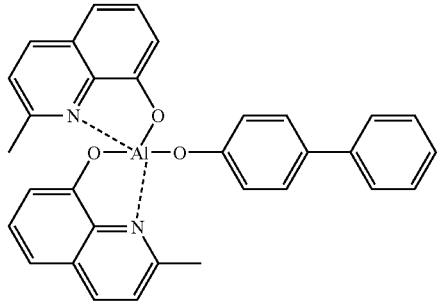

BAlq

Example 10

Fabrication of Organic EL Device

An organic EL device was fabricated in the same manner as term (2) of Example 9, except that bis(2-phenylisoquinoline) iridium acetylacetonate (hereinafter abbreviated as "Ir(piq)2 (acac)") was used instead of adding 5% by weight of Ir(ppy)3 to the light emitting layer and except that a concentration of Ir(piq)2(acac) in the light emitting layer was set to 15% by weight.

The device thus obtained was subjected to a to a test passing electric current and as a result, red light emission of 10000 cd/m² at a voltage of 8 V was obtained.

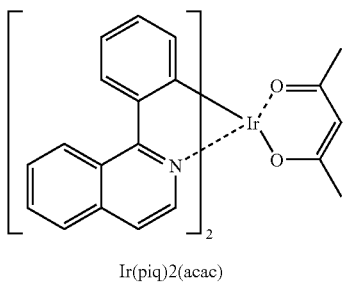

Ir(piq)2(acac)

As described above, a light emitting layer was formed from the fluorene-based derivative represented by Formula (1) and the fluorescent dopant in the organic EL device of the present invention, whereby blue light emission having an enhanced current efficiency was obtained. Further, the fluorene-based derivative represented by Formula (1) and the phosphorescent heavy metal complex were used in combination to form a light emitting layer, whereby phosphorescent luminance was obtained.

INDUSTRIAL APPLICABILITY

As explained above in details, the organic EL device of the present invention fabricated by using the fluorene-based derivative represented by Formula (1) has an enhanced current efficiency and is useful as an organic EL device having a high practicality.

What is claimed is:

1. A fluorene-based derivative expressed by the following Formula (1):

wherein k and n each are an integer of 0 to 10 and satisfy k+n>1;

m is an integer of 1 to 10;

X and Y each independently represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms; and X and Y may be the same with or different from each other;

A and C each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group or alkylene group having 1 to 50 carbon atoms or a substituted or unsubstituted alkenyl or alkenylene group having 1 to 50 carbon atoms; A and C may be the same with or different from each other; however, (a) when X or Y is a single bond, A or C represents a substituted or unsubstituted condensed polycyclic aromatic group having two rings or a substituted or unsubstituted condensed polycyclic heterocyclic group having two rings, and (b) when X and Y are single bonds, both A and C cannot represent an anthrylene group;

B represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms;

FL represents a fluorene-based derivative group represented by any of the following Formulas (2) to (5) or a group comprising the combination of these fluorene-based derivative groups, and when m is 2 or more, a plurality of (FL—B) may be the same with or different from each other;

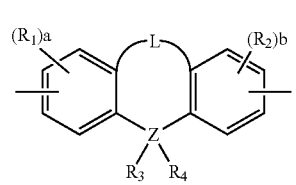

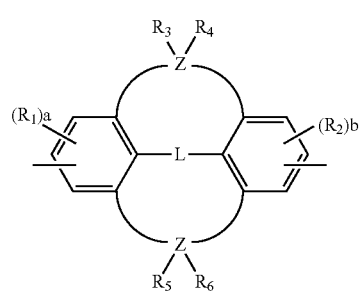

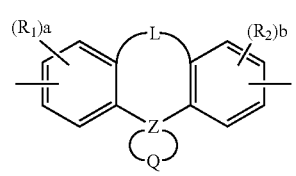

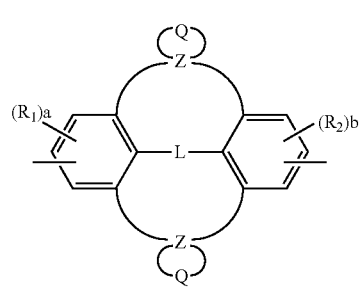

in Formulas (2) to (5), L represents a single bond;

Z is a carbon atom;

Q is a cyclic structure-forming group, and a cyclic structure formed by Z—Q may further be condensed with a substituted or unsubstituted cycloalkyl group having 1 to 50 carbon atoms, a substituted or unsubstituted aromatic group having 6 to 50 nuclear carbon atoms or a substituted or unsubstituted aromatic heterocyclic group having 5 to 50 nuclear atoms;

$R_1$ to $R_6$ each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 2 to 50 carbon atoms, a carboxyl group, a halogen atom, a cyano group, a nitro group or a hydroxyl group; when plural $R_1$ to $R_6$ are present, they may be the same with or different from each other, and adjacent groups out of $R_1$ to $R_6$ may bond each other to form a ring structure; and a and b each are an integer of 0 to 4, wherein in at least one of (A—X) or (Y—C) in said Formula (1) has a structure represented by the following Formula:

—$Ar_1$—CH=CH—$Ar_2$ (7)

wherein $Ar_1$ is a substituted or unsubstituted alkylene group having 1 to 50 carbon atoms, a substituted or unsubstituted aromatic group having 6 to 50 nuclear carbon atoms or a substituted or unsubstituted aromatic heterocyclic group having 5 to 50 nuclear atoms; $Ar_2$ is a substituted or unsubstituted aromatic group having 6 to 50 nuclear carbon atoms or a substituted or unsubstituted aromatic heterocyclic group having 5 to 50 nuclear atom.

2. The fluorene-based derivative as described in claim 1 which is a light emitting material for an organic electroluminescence device.

3. The fluorene-based derivative as described in claim 1 which is a host material for an organic electroluminescence device.

4. An organic electroluminescence device in which an organic thin film layer comprising a single layer or plural layers including at least a light emitting layer is sandwiched between a cathode and an anode, wherein at least one layer of the organic thin film layers described above comprises the fluorene-based derivative represented by Formula (1) as described in claim 1 in the form of a single component or a mixed component.

5. The organic electroluminescence device as described in claim 4, wherein said light emitting layer comprises the fluorene-based derivative represented by Formula (1) as a host material.

6. The organic electroluminescence device as described in claim 5, wherein said light emitting layer further comprises an arylamine compound.

7. The organic electroluminescence device as described in claim 5, wherein said light emitting layer further comprises a styrylamine compound.

8. The organic electroluminescence device as described in claim 5, wherein said light emitting layer further comprises a metal complex compound.

9. A fluorene-based derivative expressed by the following Formula (1):

(A—X)$_k$—(FL—B)$_m$(Y—C)$_n$ (1)

wherein k and n each are an integer of 0 to 10 and satisfy k+n>1;
m is an integer of 1 to 10;
X and Y each independently represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms; and X and Y may be the same with or different from each other;
A and C each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group or alkylene group having 1 to 50 carbon atoms or a substituted or unsubstituted alkenyl or alkenylene group having 1 to 50 carbon atoms; A and C may be the same with or different from each other; however, (a) when X or Y is a single bond, A or C represents a substituted or unsubstituted condensed polycyclic aromatic group having two rings or a substituted or unsubstituted condensed polycyclic heterocyclic group having two rings, (b) when X and Y are unsubstituted alkenylene groups, both A and C cannot represent a substituted aromatic group having 6 carbon atoms, and (c) when X and Y are single bonds, both A and C cannot represent an anthrylene group;

B represents a single bond, a substituted or unsubstituted aromatic group having 6 to 50 nuclear carbon atoms, a substituted or unsubstituted alkylene group having 1 to 50 carbon atoms or a substituted or unsubstituted alkenylene group having 1 to 50 carbon atoms;

FL represents a fluorene-based derivative group represented by any of the following Formulas (2) to (5) or a group comprising the combination of these fluorene-based derivative groups, and when m is 2 or more, a plurality of (FL—B) may be the same with or different from each other;

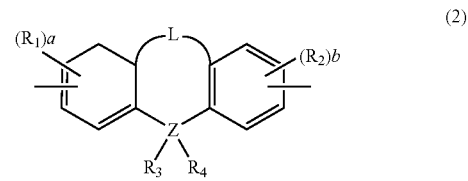

(2)

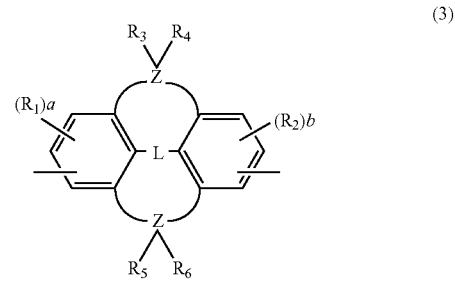

(3)

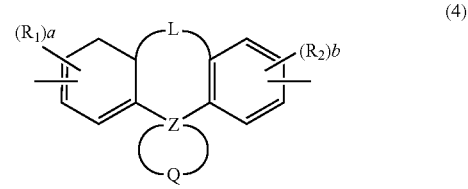

(4)

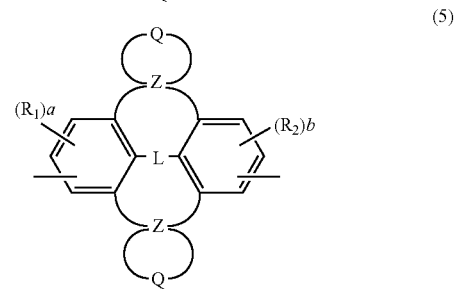

(5)

in Formulas (2) to (5), L represents a single bond;
Z is a carbon atom;
Q is a cyclic structure-forming group, and a cyclic structure formed by Z—Q may further be condensed with a substituted or unsubstituted cycloalkyl group having 1 to 50 carbon atoms, a substituted or unsubstituted aromatic group having 6 to 50 nuclear carbon atoms or a substituted or unsubstituted aromatic heterocyclic group having 5 to 50 nuclear atoms;

$R_1$ to $R_6$ each independently represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 2 to 50 carbon atoms, a carboxyl group, a halogen atom, a cyano group, a nitro group or a hydroxyl group; when plural $R_1$ to $R_6$ are present, they may be the same with or different from each other, and adjacent groups out of $R_1$ to $R_6$ may bond each other to form a ring structure; and a and b each are an integer of 0 to 4, wherein in at least one of (A—X) or (Y—C) in said Formula (1) has a structure represented by the following Formula:

$$-R_3-Ar_3 \qquad (8)$$

wherein $R_3$ is a substituted or unsubstituted alkylene group having 1 to 50 carbon atoms, and $Ar_3$ is a substituted or unsubstituted aromatic group having 6 to 50 nuclear carbon atoms or a substituted or unsubstituted aromatic heterocyclic group having 5 to 50 nuclear atoms.

10. The fluorene-based derivative as described in claim 9, which is a light emitting material for an organic electroluminescence device.

11. The fluorene-based derivative as described in claim 9, which is a host material for an organic electroluminescence device.

12. An organic electroluminescence device in which an organic thin film layer comprising a single layer or plural layers including at least a light emitting layer is sandwiched between a cathode and an anode, wherein at least one layer of the organic thin film layers described above comprises the fluorene-based derivative represented by Formula (1) as described in claim 9 in the form of a single component or a mixed component.

13. The organic electroluminescence device as described in claim 12, wherein said light emitting layer comprises the fluorene-based derivative represented by Formula (1) as a host material.

14. The organic electroluminescence device as described in claim 13, wherein said light emitting layer further comprises an arylamine compound.

15. The organic electroluminescence device as described in claim 13, wherein said light emitting layer further comprises a styrylamine compound.

16. The organic electroluminescence device as described in claim 13, wherein said light emitting layer further comprises a metal complex compound.

* * * * *

UNITED STATES PATENT AND TRADEMARK OFFICE
CERTIFICATE OF CORRECTION

PATENT NO. : 7,683,225 B2  Page 1 of 1
APPLICATION NO. : 11/282640
DATED : March 23, 2010
INVENTOR(S) : Ito et al.

It is certified that error appears in the above-identified patent and that said Letters Patent is hereby corrected as shown below:

On the title page, the Terminal Disclaimer information has been omitted. Item (45) and the Notice information should read as follows:

Title Page, Item (45)

-- (45) **Date of Patent: *Mar. 23, 2010**

(*) Notice: Subject to any disclaimer, the term of this patent is extended or adjusted under 35 U.S.C. 154(b) by 0 days.

This patent is subject to a terminal disclaimer. --

Signed and Sealed this

First Day of June, 2010

David J. Kappos
*Director of the United States Patent and Trademark Office*